US007838247B2

(12) United States Patent
St. George-Hyslop et al.

(10) Patent No.: US 7,838,247 B2
(45) Date of Patent: Nov. 23, 2010

(54) ANTIBODY SPECIFIC FOR MUTANT PRESENILIN 2 AND METHOD OF USE THEREOF

(75) Inventors: Peter H. St. George-Hyslop, Toronto (CA); Johanna M. Rommens, Toronto (CA); Paul E. Fraser, Toronto (CA)

(73) Assignees: HSC Research and Development Limited Partnership, Toronto, Ontario (CA); The Governing Council of the University of Toronto, Toronto, Ontario (CA)

( * ) Notice: Subject to any disclaimer, the term of this patent is extended or adjusted under 35 U.S.C. 154(b) by 32 days.

(21) Appl. No.: 11/894,723

(22) Filed: Aug. 20, 2007

(65) Prior Publication Data

US 2008/0286813 A1    Nov. 20, 2008

Related U.S. Application Data

(60) Continuation of application No. 11/070,405, filed on Feb. 24, 2005, now Pat. No. 7,507,798, which is a continuation of application No. 09/689,159, filed on Oct. 12, 2000, now Pat. No. 6,998,467, which is a division of application No. 08/509,359, filed on Jul. 31, 1995, now abandoned, which is a continuation-in-part of application No. 08/496,841, filed on Jun. 28, 1995, now Pat. No. 6,210,919, which is a continuation-in-part of application No. 08/431,048, filed on Apr. 28, 1995, now Pat. No. 6,531,586.

(51) Int. Cl.
*G01N 33/53* (2006.01)
*C07K 16/18* (2006.01)
*C12P 21/08* (2006.01)
*C12N 5/20* (2006.01)

(52) U.S. Cl. .................. 435/7.1; 530/387.9; 530/388.1; 435/70.21; 435/331; 435/346

(58) Field of Classification Search ........................ None
See application file for complete search history.

(56) References Cited

U.S. PATENT DOCUMENTS

| | | | |
|---|---|---|---|
| 5,262,332 A | 11/1993 | Selkoe | |
| 5,297,562 A | 3/1994 | Potter | |
| 5,449,604 A | 9/1995 | Schellenberg et al. | |
| 5,530,101 A * | 6/1996 | Queen et al. ............. | 530/387.3 |
| 5,545,808 A | 8/1996 | Hew et al. | |
| 5,668,006 A | 9/1997 | Hadcock et al. | |
| 6,210,919 B1 | 4/2001 | St. George-Hyslop et al. | |
| 6,468,791 B1 | 10/2002 | Tanzi et al. | |
| 6,531,586 B1 | 3/2003 | St. George-Hyslop et al. | |

FOREIGN PATENT DOCUMENTS

| | | |
|---|---|---|
| CA | 2054302 | 4/1992 |
| CA | 2071105 | 12/1992 |
| CA | 2096911 | 11/1993 |
| EP | 0274826 * | 7/1988 |
| WO | WO 91/19810 | 12/1991 |
| WO | WO 94/00569 | 1/1994 |
| WO | WO 94/23049 | 10/1994 |
| WO | WO 97/03086 | 1/1997 |
| WO | WO 97/03192 | 1/1997 |
| WO | WO 97/03999 | 2/1997 |

OTHER PUBLICATIONS

Diehlmann A. et al. Analysis of Presenilin 1 and Presenilin 2 expression and processing by newly developed monoclonal antibodies. J. Neurosci Res. 1999; 56:405-419.*
Morton ME. et al. Monoclonal antibody to the alpha1-subunit of the dihydropyridine-binding complex inhibits calcium currents in BC3H1 myocytes. J. Biol Chem. 1988; 263(2):613-616.*
Nayer WG & Dillon JS. Calcium antagonists and their mode of action: an historical overview. Br J Clin Pharmac. 1986; 21:97S-107S.*
Auffray et al., EMBL Sequence Data Library, Feb. 17, 1995, Accession No. F08730.
Barinaga, "New Alzheimer's gene found," *Science*, 268:1845-1846 (1995).
Cameron et al., "Transgenic Science," *British Veterinary Journal*, 150:9-24 (1994).
Chambon et al., EMBL Sequence Data Library, Feb. 7, 1992, Accession No. M84820.
Chartier-Harlin et al., "Early onset Alzheimer's disease caused by mutations at codon 717 of the β-amyloid precursor protein gene;" *Nature*, 353:844-846 (1991).
Citron et al., "Mutant Presenilins of Alzheimer's Disease Increase Production of 42-residue Amyloid β-protein in Both Transfected Cells and Transgenic Mice," *Nat. Med.*, 3:67-72 (1997).
Drivas et al., EMBL Sequence Data Library, Feb. 19, 1991, Accession No. X53143.
Felsenstein et al., "Transgenic Rat and In-Vitro Studies of β-Amyloid Precursor Protein Processing," *Alzheimer's and Parkinson's Diseases*, pp. 401-409 (Hanin, et al., Plenum Press, NY) (1995).
Fleischhauer et al., EMBL Sequence Data Library, Mar. 31, 1992, Accession No. X63522.
Foncin , "Alzheimer's Presenile dementia transmitted in an extended kindred," *Rev. Neurol (Paris)*, 141:194-202 (1985).
Fujiwara et al., EMBL Sequence Data Library, Aug. 25, 1995, Accession No. D55326.

(Continued)

*Primary Examiner*—Daniel E Kolker
*Assistant Examiner*—Kimberly A. Ballard
(74) *Attorney, Agent, or Firm*—Ropes & Gray LLP; James F. Haley, Jr.; Raymond M. Doss

(57) ABSTRACT

The present invention describes the identification, isolation, cloning, and determination of the Alzheimer Related Membrane Protein (ARMP) gene on chromosome 14 and a related gene, E5-1, on chromosome 1. Normal and mutant copies of both genes are presented. Transcripts and products of these genes are useful in detecting and diagnosing Alzheimer's disease, developing therapeutics for treatment of Alzheimer's disease, as well as the isolation and manufacture of the protein and the construction of transgenic animals expressing the mutant genes.

5 Claims, 11 Drawing Sheets

OTHER PUBLICATIONS

Goate et al., "Segregation of a missense mutation in the amyloid precursor protein gene with familial Alzheimer's disease," *Nature*, 349:704-706 (1991).
Goudsmit et al., "Familial Alzheimer's Disease in two kindreds of the same geographic and ethnic origin: a clinical and genetic study," *J. Neurol. Sci.*, 49:79-89 (1981).
Gyapay et al., "The 1993-1994 Genethon human genetic linkage map," *Nature Genetics*, 7:246-311 (1994).
Hillier et al., EMBL Sequence Data Library, Apr. 22, 1995, Accession No. R12984.
Hillier et al., EMBL Sequence Data Library, Mar. 6, 1995, Accession No. T64843.
Houdebine et al., "Production of pharmaceutical proteins from transgenic animals," *Journal of Biotechnology*, 34(3):269-287 (1994).
Johansson et al., "Molecular cloning and expression of a pituitary gland protein modulating intestinal fluid secretion," *The Journal of Biological Chemistry*, 270(35):20615-20620 (1995).
Kappell et al., "Regulating gene expression in transgenic animals," *Current Opinion in Biotechnology*, 3:548-553 (1992).
Karlinsky et al., "Molecular and prospective phenotypic characterization of a pedigree with familial Alzheimer's disease and a missense mutation in codon 717 of the β-amyloid precursor protein (APP) gene," *Neurology*, 42:1445-1453 (1992).
Katzman, "Alzheimer's Disease," *N. Eng. J. Med.*, 314:964-973 (1986).
Lannfelt, "Alzheimer's disease: molecular genetics and transgenic animal models," *Behav. Brain Res.*, 57:207-213 (1993).
Ledley, "Clinical Considerations in the Design of Protocols for Somatic Gene Therapy," *Human Gene Therapy*, 2:77-83 (1991).
L'Hernault et al., "Mutation of a Putative Sperm Membrane Protein in *Caenorhabditis elegans* Prevents Sperm Differentiation but Not Its Associated Meiotic Divisions," *J. Cell Biol.*, 119(1):55-68 (1992).
Li et al., "Identification and expression analysis of a potential familial Alzheimer disease gene on chromosome 1 related to AD3," *PNAS*, 92:12180-12184 (1995).
Mullan et al., "A locus for familial early-onset Alzheimer's disease on the long arm of chromosome 14, proximal to the α1-antichymotrypsin gene," *Nature Genetics*, 2:340-342 (1992).
Mullan et al., "A pathogenic mutation for probable Alzheimer's disease in the APP gene at the N-terminus of β-amyloid," *Nature Genetics*, 1:345-347 (1992).
Mullins et al., *Journal of Clinical Investigation*, 98:S37-S40 (1996).
Mullins et al., "Transgenesis in Nonmurine Species," *Hypertension*, 22(4):630-633 (1993).
Murrell et al., "A mutation in the amyloid precursor protein associated with hereditary Alzheimer's disease," *Science*, 254:97-99 (1995).
Nee et al., "A family with histologically confirmed Alzheimer's Disease," *Arch Neurol.*, 40:203-208 (1983).
Oster-Granite, "Age-dependent neuronal and synaptic degeneration in mice transgenic for the C terminus of the amyloid precursor protein," *J Neuroscience*, 16:6732-6741 (1996).
Pawlak et al., EMBL Sequence Data Library, Dec. 20, 1994, Accession No. T18858.
Pericak-Vance et al., "Genetic linkage studies in Alzheimer's Disease families," *Exp. Neurol.*, 102:271-279 (1988).
Porteous, "How relevant are mouse models for human diseases to somatic gene therapy?" *Tibtech*, II:173-181 (1993).
Pursel et al., "Genetic Engineering of Livestock," *Science*, 244:1281-1288 (1989).
St. George-Hyslop, et al., "Alzheimer's Disease and Possible Gene Interaction," *Science*, 263:537 (1994).
St. George-Hyslop, et al., "Genetic evidence for a novel familial Alzheimer's disease locus on chromosome 14," *Nature Genetics*, 2:330-334 (1992).
St. George-Hyslop, et al., "Genetic linkage studies suggest that Alzheimer's disease is not a single homogeneous disorder," *Nature*, 347:194-197 (1990).
Strittmatter, et al., "Apolipoprotein E: High-Avidity Binding to β-Amyloid and Increased Frequency of Type 4 Allele in Late-Onset Familial Alzheimer Disease," *PNAS*, 90:1977-1981 (1993).
Strojek et al., "The use of transgenic animal techniques for livestock improvement," *Genetic Engineering: Principles and Methods*, 10:221-246 (1988).
Taniguchi et al., "Cloning of the cDNA encoding rat Presenilin-1," *Gene*, 186(1):73-75 (1997).
Van Broeckhoven et al., "Mapping of a gene predisposing to early-onset Alzheimer's disease to chromosome 14q24.3," *Nature Genetics*, 2:335-339 (1992).
Walkley et al., EMBL Sequence Data Library, Jan. 1, 1994, Accession No. X74801.
Wall, "Transgenic livestock: Progress and prospects for the future," *Theriogenology*, 45:57-68 (1996).
Rogaev, et al., "Analysis of the c-FOS gene on chromosome 14 and the promoter of the amyloid precursor protein gene in familial Alzheimer's disease," *Neurology*, 43:2275-2279 (1993).
Rommens, et al., "A transcription map of the region containing the Huntington disease gene," *Hum. Molec. Genet.*, 2:901-907 (1993).
Salter et al., "Transgenic Chickens: Insertion of Retroviral Genes into the Chicken Germ Line," *Virology*, 157:236-240 (1987).
Saunders et al., "Association of apolipoprotein E allele e4 with the late-onset familial and sporadic Alzheimer's disease," *Neurology*, 43:1467-1472 (1993).
Schellenberg et al., "Chromosome 14 and Late-Onset Familial Alzheimer Disease (FAD)," *Am. J. Hum. Genet.*, 53:619-628 (1993).
Schellenberg et al., "Genetic Linkage Evidence for a Familial Alzheimer's Disease Locus on Chromosome 14," *Science*, 258:668-670 (1992).
Seamark et al., "Progress and emerging problems in livestock transgenesis: a summary perspective," *Reproductive Fertility and Development*, 6:653-657 (1994).
Selkoe, "Alzheimer's disease. In the beginning . . . ," *Nature*, 354:532-433 (1991).
Sevigny, et al., EMBL Sequence Data Library, Jan. 7, 1995, Accession No. U17104.
Sherrington et al., "Cloning of a gene bearing missense mutations in early-onset familial Alzheimer's disease," *Nature*, 375:754-760 (1995).
Wong et al., "Mutation of the gene for the human lysosomal serine protease Cathespin G is not the cause of aberrant APP processing in familial Alzheimer disease," *Neurosci. Lett.*, 152:96-98 (1993).
Yamada et al., "Complementary DNA for the Mouse Homolog of the Human Amyloid Beta Protein Precursor," *Biochem. Biophys. Res. Comm,*. 149(2):665-71 (1987).
Yu et al., EMBL Sequence Data Library, Dec. 10, 1991, Accession No. M81766.
Zahraoui et al., EMBL Sequence Data Library, Jul. 22, 1994, Accession No. X56740.
Levy-Lahad et al., "Candidate gene for the chromosome 1 familial Alzheimer's disease locus," *Science*, 269:973-977 (1995).
Rogaev et al., "Familial Alzheimer's disease in kindreds with missense mutations in a gene on chromosome 1 related to the Alzheimer's disease type 3 gene," *Nature*, 376:775-778 (1995).
Sahara et al., "Identification and characterization of presenilin I-467, I-463 and I-374," *FEBS Letters*, 381:7-11 (1996).

* cited by examiner

Figure 1d

```
cFOS ——
  DLST ——
    z112 ——
      z2 ——
      S20i15 ——
        S153 ——         S164 ——
          LTBP2 ——       S171 ——
          S31iii125 ——     S182 ——
            S22171 ——      c1138 ——
              Z128 ——       c189 ——
                Z3 ——       c462 ——
                Z113 ——              S198
                                     c265/295
```

Met 146 Leu

Leu 286 Val

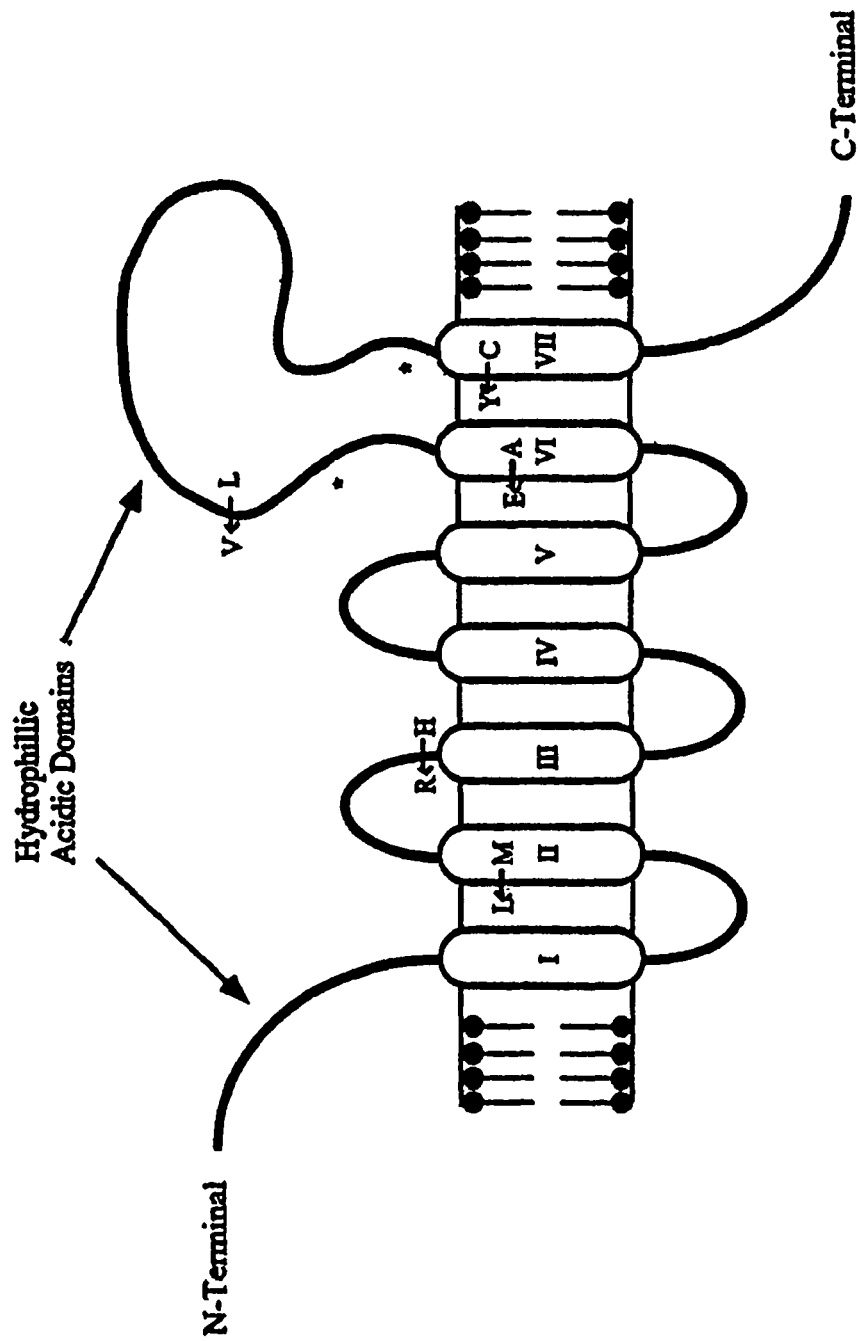

ANTIBODY SPECIFIC FOR MUTANT PRESENILIN 2 AND METHOD OF USE THEREOF

RELATED APPLICATIONS

The application is a continuation of U.S. application Ser. No. 11/070,405, filed Feb. 24, 2005, which is a continuation of U.S. application Ser. No. 09/689,159, filed Oct. 12, 2000, now U.S. Pat. No. 6,998,467, which is a divisional of U.S. application Ser. No. 08/509,359, filed Jul. 31, 1995, now abandoned, which is a continuation-in-part of U.S. patent application Ser. No. 08/496,841, filed Jun. 28, 1995, now U.S. Pat. No. 6,210,919, which is a continuation-in-part of U.S. patent application Ser. No. 08/431,048, filed Apr. 28, 1995, now U.S. Pat. No. 6,531,586.

FIELD OF THE INVENTION

The present invention relates generally to the field of neurological and physiological dysfunctions associated with Alzheimer's Disease. More particularly, the invention is concerned with the identification, isolation and cloning of the gene which when mutated is associated with Alzheimer's Disease as well as its transcript, gene products and associated sequence information and neighbouring genes. The present invention also relates to methods of diagnosing for and detection of carriers of the gene, Alzheimer's Disease diagnosis, gene therapy using recombinant technologies and therapy using the information derived from the DNA, protein, and the metabolic function of the protein.

BACKGROUND OF THE INVENTION

In order to facilitate reference to various journal articles, a listing of the articles is provided at the end of this specification.

Alzheimer's Disease (AD) is a degenerative disorder of the human central nervous system characterized by progressive memory impairment and cognitive and intellectual decline during mid to late adult life (Katzman, 1986). The disease is accompanied by a constellation of neuropathologic features principal amongst which are the presence of extracellular amlyoid or senile plaques and the neurofibrillary degeneration of neurons. The etiology of this disease is complex, although in some families it appears to be inherited as an autosomal dominant trait. However, even among these inherited forms of AD, there are at least three different genes which confer inherited susceptibility to this disease (St. George-Hyslop et al., 1990). The $_e4$ (Cys112Arg) allelic polymorphism of the Apolipoprotein E (AopE) gene has been associated with AD in a significant proportion of cases with onset late in life (Saunders et al., 1993; Strittmatter et al., 1993). Similarly, a very small proportion of familial cases with onset before age 65 years have been associated with mutations in the β-amyloid precursor protein (APP) gene (Chartier-Harlin et al., 1991; Goate et al., 1991; Murrell et al., 1991; Karlinsky et al., 1992; Mullan et al., 1992). A third locus (AD3) associated with a larger proportion of cases with early onset AD has recently been mapped to chromosome 14q24.3 (Schellenberg et al., 1992; St. George-Hyslop et al., 1992; Van Broeckhoven et al., 1992).

Although chromosome 14q carries several genes which could be regarded as candidate genes for the site of mutations associated with AD3 (e.g. cFOS, alpha-1-antichymotrypsin, and cathepsin G), most of these candidate genes have been excluded on the basis of their physical location outside the AD3 region and/or the absence of mutations in their respective open reading frames (Schellenberg, G D et al., 1992; Van Broeckhoven, C et al., 1992; Rogaev et al., 1993; Wong et al., 1993).

There have been several developments and commercial directions in respect of treatment of Alzheimer's disease and diagnosis thereof. Published PCT application WO 94 23049 describes transfection of high molecular weight YAC DNA into specific mouse cells. This method is used to analyze large gene complexes, for example the transgenic mice may have increased amyloid precursor protein gene dosage, which mimics the trisomic condition that prevails in Downs Syndrome and the generation of animal models with β-amyloidosis prevalent in individuals with Alzheimer's Disease. Published international application WO 94 00569 describes transgenic non-human animals harbouring large trans genes such as the trans gene comprising a human amyloid precursor protein gene. Such animal models can provide useful models of human genetic diseases such as Alzheimer's Disease.

Canadian Patent application 2096911 describes a nucleic acid coding for amyloid precursor protein-cleaving protease, which is associated with Alzheimer's Disease and Down's syndrome. The genetic information may be used to diagnose Alzheimer's disease. The genetic information was isolated from chromosome 19. Canadian patent application 2071105, describes detection and treatment of inherited or acquired Alzheimer's disease by the use of YAC nucleotide sequences. The YACs are identified by the numbers 23CB10, 28CA12 and 26FF3.

U.S. Pat. No. 5,297,562, describes detection of Alzheimer's Disease having two or more copies of chromosome 21. Treatment involves methods for reducing the proliferation of chromosome 21 trisomy. Canadian Patent Application 2054302, describes monoclonal antibodies which recognize human brain cell nucleus protein encoded by chromosome 21 and are used to detect changes or expression due to Alzheimer's Disease or Down's Syndrome. The monoclonal antibody is specific to a protein encoded by human chromosome 21 and is linked to large pyramidal cells of human brain tissue.

By extensive effort and a unique approach to investigating the AD3 region of chromosome 14q, the Alzheimer's related membrane protein (ARMP) gene has been isolated, cloned and sequenced from within the AD3 region on chromosome 14q24.3. In addition, direct sequencing of RT-PCR products spanning this 3.0 kb cDNA transcript isolated from affected members of at least eight large pedigrees linked to chromosome 14, has led to the discovery of missense mutations in each of these different pedigrees. These mutations are absent in normal chromosomes. It has not been established that the ARMP gene is causative of familial Alzheimer's Disease type AD3. In realizing this link, it is understood that mutations in this gene can be associated with other cognitive, intellectual, or psychological disease such as cerebral hemorrhage, schizophrenia, depression, mental retardation and epilepsy. These phenotypes are present in these AD families and these phenotypes have been seen in mutations of the APP protein gene. The Amyloid Precursor Protein (APP) gene is also associated with inherited Alzheimer's Disease. The identification of both normal and mutant forms of the ARMP gene and gene products has allowed for the development of screening and diagnostic tests for ARMP utilizing nucleic acid probes and antibodies to the gene product. Through interaction with the defective gene product and the pathway in which this gene product is involved, gene therapy, manipulation and delivery are now made possible.

SUMMARY OF THE INVENTION

Various aspects of the invention are summarized as follows. In accordance with a first aspect of the invention, a purified mammalian polynucleotide is provided which codes for Alzheimer's related membrane protein (ARMP). The polynucleotide has a sequence which is the functional equivalent of the DNA sequence of ATCC deposit 97124, deposited Apr. 28, 1995. The mammalian polynucleotide may be in the form of DNA, genomic DNA, cDNA, mRNA and various fragments and portions of the gene sequence encoding ARMP. The mammalian DNA is conserved in many species, including human and rodents, example, mice. The mouse sequence encoding ARMP has greater than 95% homology with the human sequence encoding the same protein.

Purified human nucleotide sequences which encode mutant ARMP have mutations at nucleotide position i) 685, A→C ii) 737, A→G iii) 986, C→A, iv) 1105, C→G, v) 1478, G→A, vi) 1027, C→T, vii) 1102, C→T and viii) 1422, C→G of Sequence ID No: 1 as well as in the cDNA sequence of a further human clone of a sequence identified by ID NO:133.

The nucleotide sequences encoding ARMP have an alternative splice form in the genes open reading frame. The human cDNA sequence which codes for ARMP has sequence ID No. 1 as well as sequence SEQ ID NO:133 as sequenced in another human clone. The mouse sequence which encodes ARMP has SEQ ID NO:3, as well as SEQ ID NO:135 derived from a further clone containing the entire coding region. Various DNA and RNA probes and primers may be made from appropriate polynucleotide lengths selected from the sequences. Portions of the sequence also encode antigenic determinants of the ARMP.

Suitable expression vectors comprising the nucleotide sequences are provided along with suitable host cells transfected with such expression vectors.

In accordance with another aspect of the invention, purified mammalian Alzheimer's related membrane protein is provided. The purified protein has an amino acid sequence encoded by polynucleotide sequence as identified above which for the human is SEQ ID NO:2 and SEQ ID NO:134 (derived from another clone). The mouse amino acid sequence is defined by SEQ ID NO:4 and SEQ ID NO. 136, the latter being translated from another clone containing the entire coding region. The purified protein may have substitution mutations selected from the group consisting of positions identified in SEQ ID NO:2 and Sequence ID NO:134.

| | |
|---|---|
| i) | M 146L |
| ii) | H 163R |
| iii) | A 246E |
| iv) | L 286V |
| v) | C 410 Y |
| vi) | A 260 V |
| vii) | A 285 V |
| viii) | L 392 V |

In accordance with another aspect of the invention, are polyclonal antibodies raised to specific predicted sequences of the ARMP protein. Polypeptides of at least six amino acid residues are provided. The polypeptides of six or greater amino acid residues may define antigenic epitopes of the ARMP. Monoclonal antibodies having suitably specific binding affinity for the antigenic regions of the ARMP are prepared by use of corresponding hybridoma cell lines. In addition, other polyclonal antibodies may be prepared by inoculation of animals with suitable peptides or holoprotein which add suitable specific binding affinities for antigenic regions of the ARMP.

In accordance with another aspect of the invention, an isolated DNA molecule is provided which codes for E5-1 protein. A plasmid including this nucleic acid was deposited with the ATCC under the terms of the Budapest Treaty on Jun. 28, 1995 and has been assigned ATCC accession number 97214.

In accordance with another aspect of the invention, purified E5-1 protein is provided, having amino acid SEQ ID NO:138.

In accordance with another aspect of the invention a bioassay is provided for determining if a subject has a normal or mutant ARMP, where the bioassay comprises
    providing a biological sample from the subject
    conducting a biological assay on the sample to detect a normal or mutant gene sequence coding form ARMP, a normal or mutant ARMP amino acid sequence, or a normal or defective protein function.

In accordance with another aspect of the invention, a process is provided for producing ARMP comprising culturing one of the above described transfected host cells under suitable conditions, to produce the ARMP by expressing the DNA sequence. Alternatively, ARMP may be isolated from mammalian cells in which the ARMP is normally expressed.

In accordance with another aspect of the invention, is a therapeutic composition comprising ARMP and a pharmaceutically acceptable carrier.

In accordance with another aspect of the invention, a recombinant vector for transforming a mammalian tissue cell to express therapeutically effective amounts of ARMP in the cells is provided. The vector is normally delivered to the cells by a suitable vehicle. Suitable vehicles include vaccinia virus, adenovirus, adeno associated virus, retrovirus, liposome transport, neuraltripic viruses, Herpes simplex virus and other vector systems.

In accordance with another aspect of the invention, a method of treating a patient deficient in normal ARMP comprising administering to the patient a therapeutically effective amount of the protein targeted at a variety of patient cells which normally express ARMP. The extent of administration of normal ARMP being sufficient to override any effect the presence of the mutant ARMP may have on the patient. As an alternative to protein, suitable ligands and therapeutic agents such as small molecules and other drug agents may be suitable for drug therapy designed to replace the protein and defective ARMP, displace mutant ARMP, or to suppress its formation.

In accordance with another aspect of the invention an immuno therapy for treating a patient having Alzheimer's Disease comprises treating the patient with antibodies specific to the mutant ARMP to reduce biological levels or activity of the mutant ARMP in the patient. To facilitate such amino acid therapy, a vaccine composition may be provided for evoking an immune response in a patient of Alzheimer's disease where the composition comprises a mutant ARMP and a pharmaceutically acceptable carrier with or without a suitable excipient. The antibodies developed specific to the mutant ARMP could be used to target appropriately encapsulated drugs/molecules, specific cellular/tissue sites. Therapies utilizing specific ligands which bind to normal or wild type ARMP of either mutant or wild type and which augments normal function of ARMP in membranes and/or cells or inhibits the deleterious effect of the mutant protein are also made possible.

In accordance with another aspect of the invention, a transgenic animal model for Alzheimer's Disease which has the mammalian polynucleotide sequence with at least one mutation which when expressed results in mutant ARMP in animal cells and thereby manifests a phenotype. For example, the human Prion gene when overexpressed in rodent peripheral nervous system and muscle cells causes a quite different response in the animal than the human. The animal may be a rodent and is preferably a mouse, but may also be other animals including rat, pig, *Irosophila melanogaster, C. elegans* (nematode), all of which are used for transgenic models. Yeast cells can also be used in which the ARMP Sequence is expressed from an artificial vector.

In accordance with another aspect of the invention, a transgenic mouse model for Alzheimer's Disease has the mouse gene encoding ARMP human or murine homologues mutated to manifest the symptoms. The transgenic mouse may exhibit symptoms of cognitive memory or behavioral disturbances. In addition or alternatively, the symptoms may appear as another cellular tissue disorder such as in mouse liver, kidney, spleen or bone marrow or other organs in which the ARMP gene is normally expressed.

In accordance with another aspect of the invention, the protein can be used as a starting point for rationale drug design to provide ligands, therapeutic drugs or other types of small chemical molecules.

BRIEF DESCRIPTION OF THE DRAWINGS

Various aspects of the invention are described hereinafter with respect to the drawings wherein:

FIG. 1*d*. Transcriptional map illustrating physical locations of the 19 independent longer cDNA clones.

FIG. 3*b*. A model for the structural organization of the putative ARMP protein. Roman numerals depict the transmembrane domains. Putative glycosylation sites are indicated as asterisks and most of the phosphorylation sites are located on the same membrane face as the two acidic hydrophillic loops. The MAP kinase site is present at residue 115 and the PKC site at residue 114. FAD mutation sites are indicated by horizontal arrows.

DETAILED DESCRIPTION OF PREFERRED EMBODIMENTS

Figure 1A:
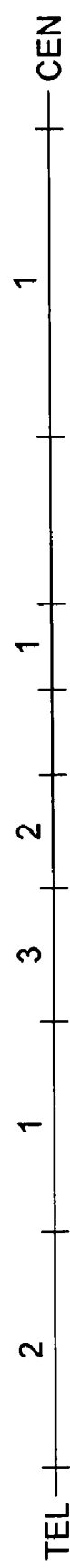
FIG. 1*a*. Genomic physical and transcriptional map of the AD3 region of chromosome 14. Genetic map inter-marker genetic distances averaged for male and female meiosis are indicated in centiMorgans.

In order to facilitate review of the various embodiments of the invention and an understanding of various elements and constituents used in making the invention and using same, the following definition of terms used in the invention description is as follows:

Alzheimer Related Membrane Protein gene (ARMP gene)—the chromosome 14 gene which when mutated is associated with familial Alzheimer's Disease and/or other inheritable disease phenotypes (e.g., cerebral hemorrhage, mental retardation, schizophrenia, psychosis, and depression). This definition is understood to include the various sequence polymorphisms that exist, wherein nucleotide substitutions in the gene sequence do not affect the essential function of the gene product, as well as functional equivalents of the nucleotide sequences of SEQ ID NO:1, SEQ ID NO:133, SEQ ID NO:3 and SEQ ID NO:135. This term primarily relates to an isolated coding sequence, but can include some or all of the flanking regulatory elements and/or introns. The term ARMP gene includes the gene in other species analogous to the human gene which when mutated is associated with Alzheimer's Disease.

Alzheimer Related Membrane Protein (ARMP)—the protein encoded by the ARMP gene. The preferred source of protein is the mammalian protein as isolated from humans or animals. Alternatively, functionally equivalent proteins may exist in plants, insects and invertebrates (such as *C. elegans*). The protein may be produced by recombinant organisms, or chemically or enzymatically synthesized. This definition is understood to include functional variants such as the various polymorphic forms of the protein wherein amino acid substitutions or deletions within the amino acid sequence do not affect the essential functioning of the protein, or its structure. It also includes functional fragments of ARMP.

Mutant ARMP gene—The ARMP gene containing one or more mutations which lead to Alzheimer's Disease and/or other inheritable disease phenotypes (e.g., cerebral hemorrhage, mental retardation, schizophrenia, psychosis, and depression). This definition is understood to include the various mutations that exist, wherein nucleotide substitutions in the gene sequence affect the essential function of the gene product, as well as mutations of functional equivalents of the nucleotide sequences of SEQ ID NO:1, SEQ ID NO:133, SEQ ID NO:3 and SEQ ID NO:135 (the corresponding amino acid sequences). This term primarily relates to an isolated coding sequence, but also can include some or all of the flanking regulatory elements and/or introns.

Mutant ARMP—a mammalian protein that is highly analogous to ARMP in terms of primary structure, but wherein one or more amino acid deletions and/or substitutions result in impairment of its essential function, so that mammals, especially humans, whose ARMP producing cells express mutant ARMP rather than the normal ARMP, demonstrate the symptoms of Alzheimer's Disease and/or other relevant inheritable phenotypes (e.g. cerebral hemorrhage, mental retardation, schizophrenia, psychosis, and depression).

mARMP gene—mouse gene analogous to the human ARMP gene. Functional equivalent as used in describing gene sequences and amino acid sequences means that a recited sequence need not be identical to the definitive sequence of the Sequence ID Nos but need only provide a sequence which functions biologically and/or chemically the equivalent of the definitive sequence. Hence sequences which correspond to a definitive sequence may also be considered as functionally equivalent sequence.

mARMP—mouse Alzheimer related membrane protein, analogous to the human ARMP, encoded by the mARMP gene. This definition is understood to include the various polymorphic forms of the protein wherein amino acid substitutions or deletions of the sequence does not affect the essential functioning of the protein, or its structure.

Mutant mARMP—a mouse protein which is highly analogous to mARMP in terms of primary structure, but wherein one or more amino acid deletions and/or substitutions result in impairment of its essential function, so that mice, whose mARMP producing cells express mutant mARMP rather than the normal mARMP demonstrate the symptoms of Alzheimer's Disease and/or other relevant inheritable phenotypes, or other phenotypes and behaviours as manifested in mice.

ARMP carrier—a mammal in apparent good health whose chromosomes contain a mutant ARMP gene that may be transmitted to the offspring and who will develop Alzheimer's Disease in mid to late adult life.

Missense mutation—A mutation of nucleic acid sequence which alters a codon to that of another amino acid, causing an altered translation product to be made.

Pedigree—In human genetics, a diagram showing the ancestral relationships and transmission of genetic traits over several generations in a family.

E5-1 gene—the chromosome 1 gene which shows homology to the ARMP gene and which when mutated is associated with familial Alzheimer's Disease and/or other inheritable disease phenotypes. This definition is understood to include the various sequence polymorphisms that exist, wherein nucleotide substitutions in the gene sequence do not affect the essential function of the gene product, as well as functional equivalents of the nucleotide SEQ ID NO:137. This term also includes the gene in other species analogous to the human gene described herein.

E5-1 protein—the protein encoded by the E5-1 gene. This term includes the protein of SEQ ID NO:138 and also functional variants such as the various polymorphic and splice variant forms of the protein wherein amino acid substitutions or deletions within the amino acid sequence do not affect the essential functioning of the protein. The term also includes functional fragments of the protein.

Mutant E5-1 gene—the E5-1 gene containing one or more mutations which lead to Alzheimer's Disease. This term is understood to include the various mutations that exist, wherein nucleotide substitutions in the gene sequence affect the essential function of the gene product.

Mutant E5-1, protein—a protein analogous to E5-1 protein but wherein one or more amino acid deletions and/or substitutions result in impairment of its essential function such that mammals, especially humans, whose E5-1 producing cells express mutant E5-1 protein demonstrate the symptoms of Alzheimer's disease.

Linkage analysis—Analysis of co-segregation of a disease trait or disease gene with polymorphic genetic markers of defined chromosomal location.

hARMP gene - Human ARMP gene.

ORF - Open reading frame.

PCR - Polymerase chain reaction.

contig - continuous cloned regions.

YAC - yeast artificial chromosome.

RT-PCR - reverse transcription polymerase chain reaction.

SSR - Simple sequence repeat polymorphism.

The present invention is concerned with the identification and sequencing of the mammalian ARMP gene in order to gain insight into the cause and etiology of familial Alzheimer's Disease. From this information, screening methods and therapies for the diagnosis and treatment of the disease can be developed. The gene has been identified, cDNA isolated and cloned, its transcripts and gene products identified and sequenced. During such identification of the gene, considerable sequence information has also been developed on intron information in the ARMP gene, flanking untranslated information and signal information and information involving neighbouring genes in the AD3 chromosome region. Direct sequencing of overlapping RT-PCR products spanning the human gene isolated from affected members of large pedigrees linked to chromosome 14 has led to the discovery of missense mutation which co-segregate with the disease.

Although it is generally understood that Alzheimer's Disease is a neurological disorder, most likely in the brain, expression of ARMP has been found in varieties of human tissue such as heart, brain, placenta, lung, liver, skeletal muscle, kidney and pancreas. Although this gene is expressed widely, the clinically apparent phenotype exists in brain although it is conceivable that biochemical phenotypes may exist in these other tissues. As with other genetic diseases such as Huntington's Disease and APP—Alzheimer's, the clinical disease manifestation may reflect different biochemistries of different cell types and tissues (which stem from genetics and the protein). Such findings suggest that AD may not be solely a neurological disorder but may also be a systemic disorder, hence requiring alternative therapeutic strategies which may be targeted to other tissues or organs or generally in addition or separately from neuronal or brain tissues.

The ARMP mutations identified have been related to Alzheimer's Disease pathology. With the identification of sequencing of the gene and the gene product, probes and antibodies raised to the gene product can be used in a variety of hybridization and immunological assays to screen for and detect the presence of either a normal or mutated gene or gene product.

Patient therapy through removal or blocking of the mutant gene product, as well as supplementation with the normal. gene product by amplification, by genetic and recombinant techniques or by immunotherapy can now be achieved. Correction or modification of the defective gene product by protein treatment immunotherapy (using antibodies to the defective protein) or knock-out of the mutated gene is now also possible. Familial Alzheimer's Disease could also be controlled by gene therapy in which the gene defect is corrected in situ or by the use of recombinant or other vehicles to deliver a DNA sequence capable of expressing the normal gene product, or a deliberately mutated version of the gene product whose effect counter balances the deleterious consequences of the disease mutation to the affected cells of the patient.

The present invention is also concerned with the identification and sequencing of a second gene, the E5-1 gene on chromosome 1, which is associated with familial Alzheimer's Disease.

Disease mechanism insights and therapies analogous to those described above in relation to the ARMP gene will be available as a result of the identification and isolation of the E5-1 gene.

Isolating the Human ARMP Gene

Genetic Mapping of the AD3 Locus.

After the initial regional mapping of the AD3 gene locus to 14q24.3 near the anonymous microsatellite markers D14S43 and D14S53 (Schellenberg, G D et al., 1992; St. George-Hyslop, P et al., 1992; Van Broeckhoven, C et al., 1992), twenty one pedigrees were used to segregate AD as a putative autosomal dominant trait (St. George-Hyslop P et al., 1992) and to investigate the segregation of 18 additional genetic markers from the 14q24.3 region which had been organized into a high density genetic linkage map (FIG. 1b) (Weissenbach et al., 1992; Gyapay et al., 1994). Pairwise maximum likelihood analyses previously published confirmed substantial cumulative evidence for linkage between FAD and all of these markers (Table 1). However, much of the genetic data supporting linkage to these markers were derived from six large early onset pedigrees FAD1 (Nee et al., 1983) FAD2 (Frommelt et al., 1991), FAD3 (Goudsmit et al., 1981; Pollen, 1993), FAD4 (Foncin et al., 1985) TOR1.1 (Bergamini, 1991) and 603 (Pericak-Vance et al., 1988) each of which provide at least one anonymous genetic marker from 14q24.3 (St. George-Hyslop, P. et al., 1992).

In order to more precisely define the location of the AD3 gene relative to the known locations of the genetic markers from 14q24.3, recombinational landmarks were sought by direct inspection of the raw haplotype data only from genotyped affected members of the six pedigrees showing definitive linkage to chromosome 14. This selective strategy in this particular instance necessarily discards data from the reconstructed genotypes of deceased affected members as well as from elderly asymptomatic members of large pedigrees, and takes no account of the smaller pedigrees of uncertain linkage status. However, this strategy is very sound because it also avoids the acquisition of potentially misleading genotype data acquired either through errors in the reconstructed genotypes of deceased affected members arising from non-paternity or sampling errors or from the inclusion of unlinked pedigrees.

Upon inspection of the haplotype data for affected subjects, members of the six large pedigrees whose genotypes were directly determined revealed obligate recombinants at D14S48 and D14S53, and at D14S258 and D14S63. The single recombinant at D14S53, which depicts a telomeric boundary for the FAD region, occurred in the same AD affected subject of the FAD1 pedigree who had previously been found to be recombinant at several other markers located telomeric to D14S53 including D14S48 (St. George-Hyslop, P et al., 1992). Conversely, the single recombinant at D14S258, which marks a centromeric boundary of the FAD region, occurred in an affected member of the FAD3 pedigree who was also recombinant at several other markers centromeric to D14S258 including D14S63. Both recombinant subjects had unequivocal evidence of Alzheimer's Disease confirmed though standard clinical tests for the illness in other affected members of their families, and the genotypes of both recombinant subjects was informative and co-segregating at multiple loci within the interval centromeric to D14S53 and telomeric to D14S258.

When the haplotype analyses were enlarged to include the reconstructed genotypes of deceased affected members of the six large pedigrees as well as data from the remaining fifteen pedigrees with probabilities for linkage of less than 0.95, several additional recombinants were detected at one or more marker loci within the interval between D14S53 and D14S258. Thus, one additional recombinant was detected in the reconstructed genotype of a deceased affected member of each of three of the larger FAD pedigrees (FAD1, FAD2 and other related families), and eight additional recombinants were detected in affected members of five smaller FAD pedigrees. However, while some of these recombinants might have correctly placed the AD3 gene within a more defined target region, we were forced to regarded these potentially closer "internal recombinants" as unreliable not only of the reasons discussed earlier, but also because they provided mutually inconsistent locations for the AD3 gene within the D14S53-D14S258 interval.

Construction of a Physical Contig Spanning the AD3 Region.

Figures 1B, 1C:
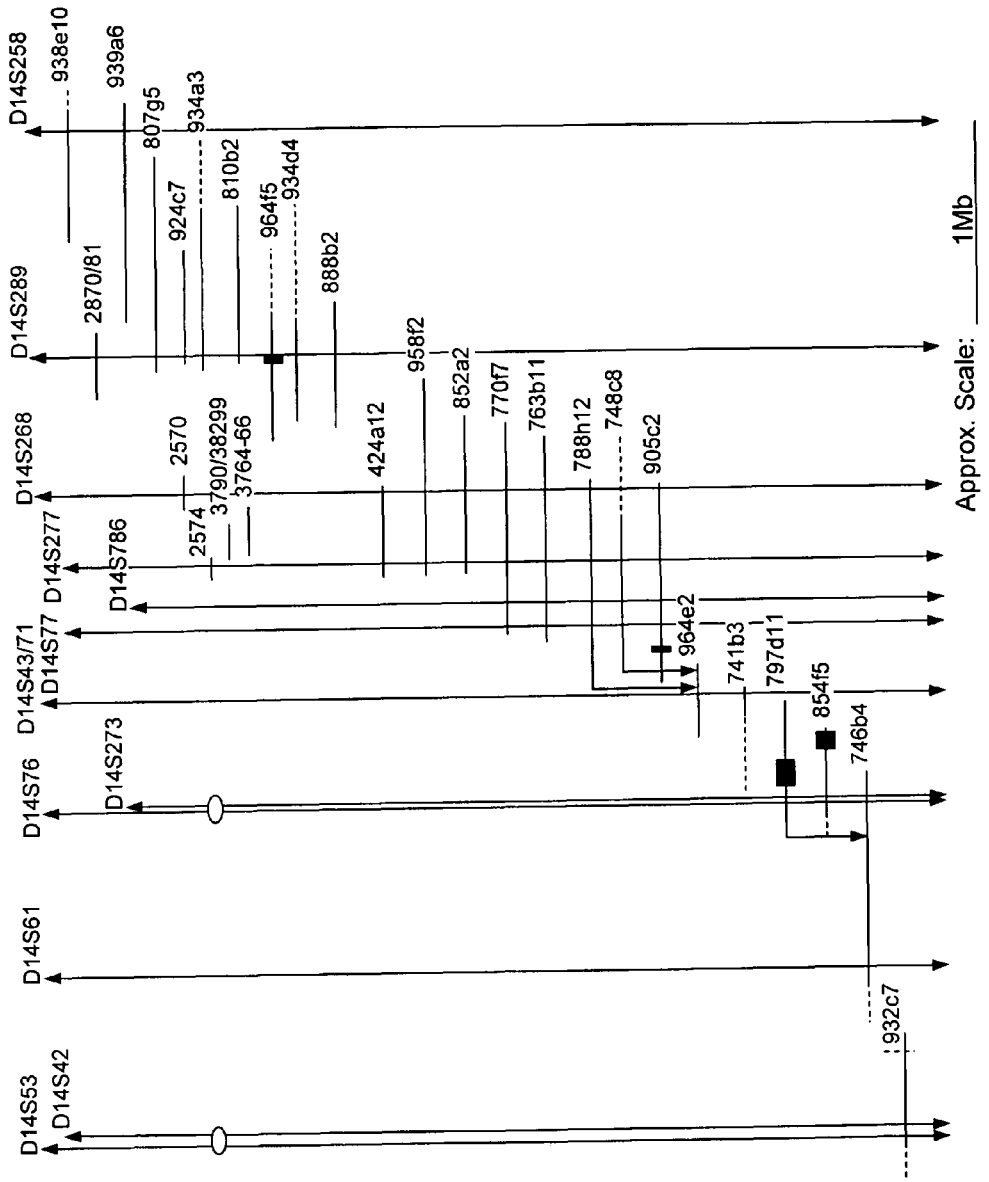
FIG. 1*b*. Is the constructed physical contig map of overlapping genomic DNA fragments cloned into YACs spanning a FAD locus on chromosome 14q.
FIG. 1*c*. Regions of interest within the constructed physical contig map.
Figure 2A:
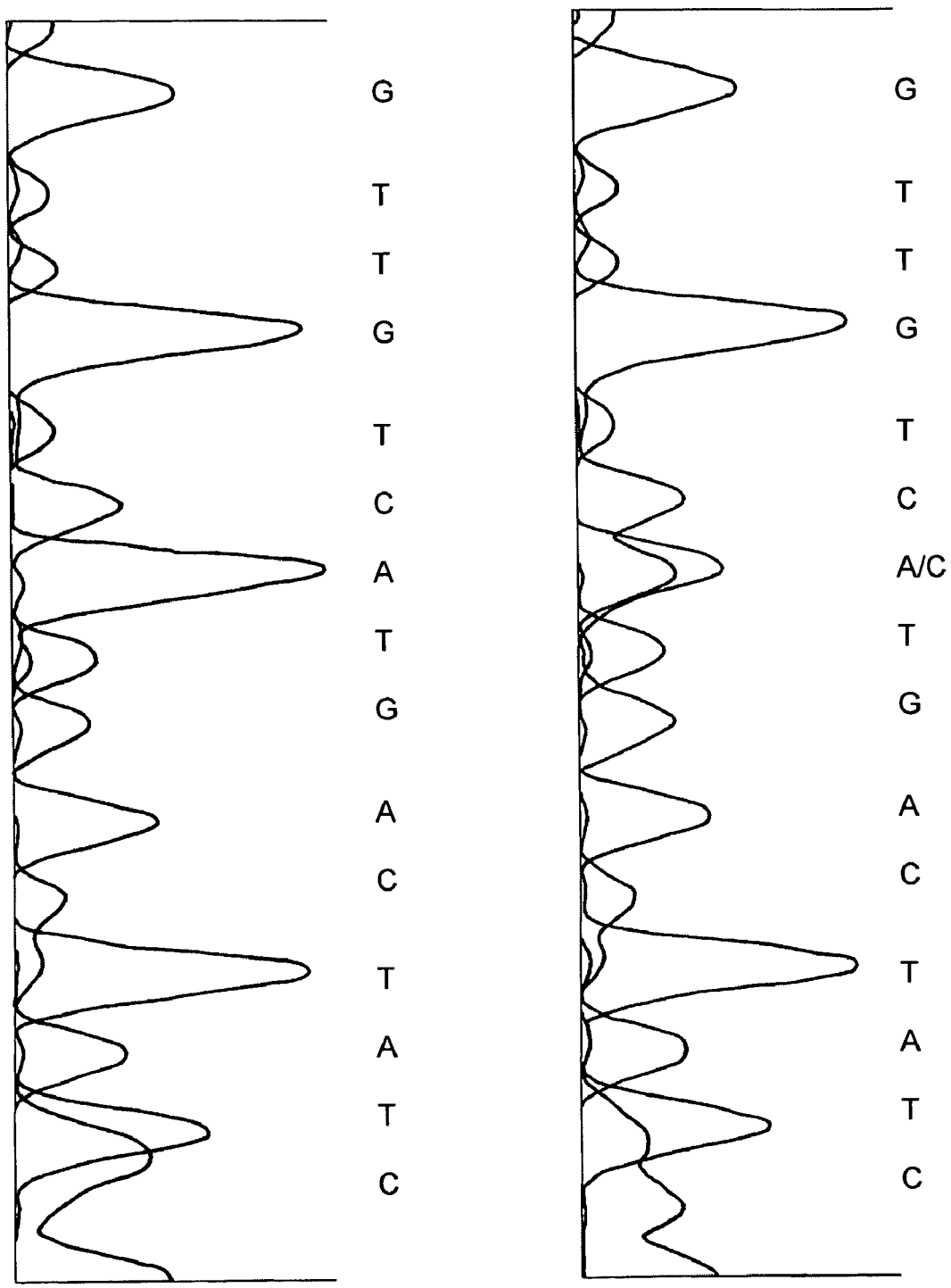
FIG. 2*a*. Automated florescent chromatograms representing the change in nucleic acids which direct (by the codon) the amino acid sequence of the gene; Met 146 Leu.
Figure 2B:
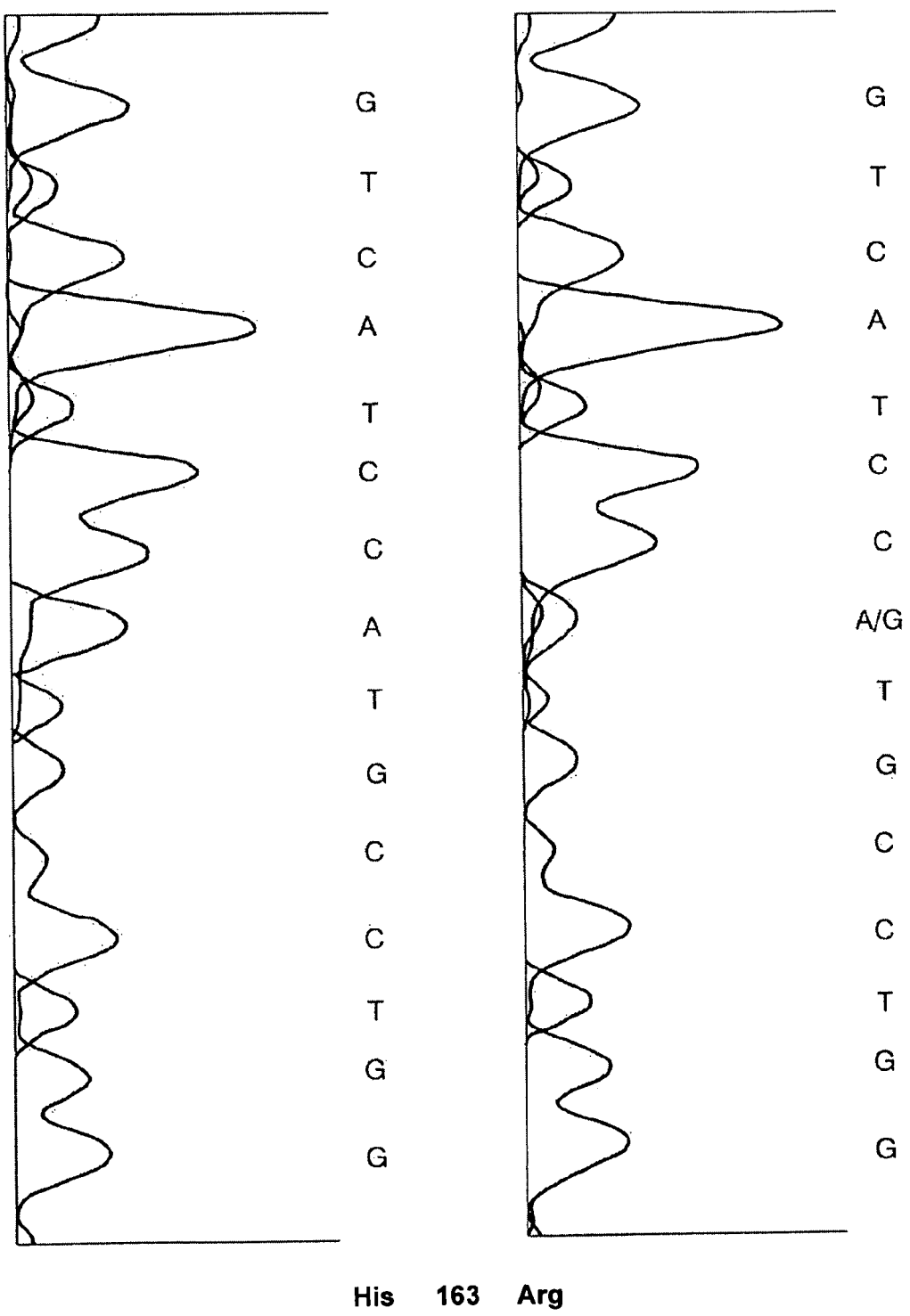
FIG. 2*b*. Automated florescent chromatograms representing the change in nucleic acids which direct (by the codon) the amino acid sequence of the gene; His 163 Arg.
Figure 2C:
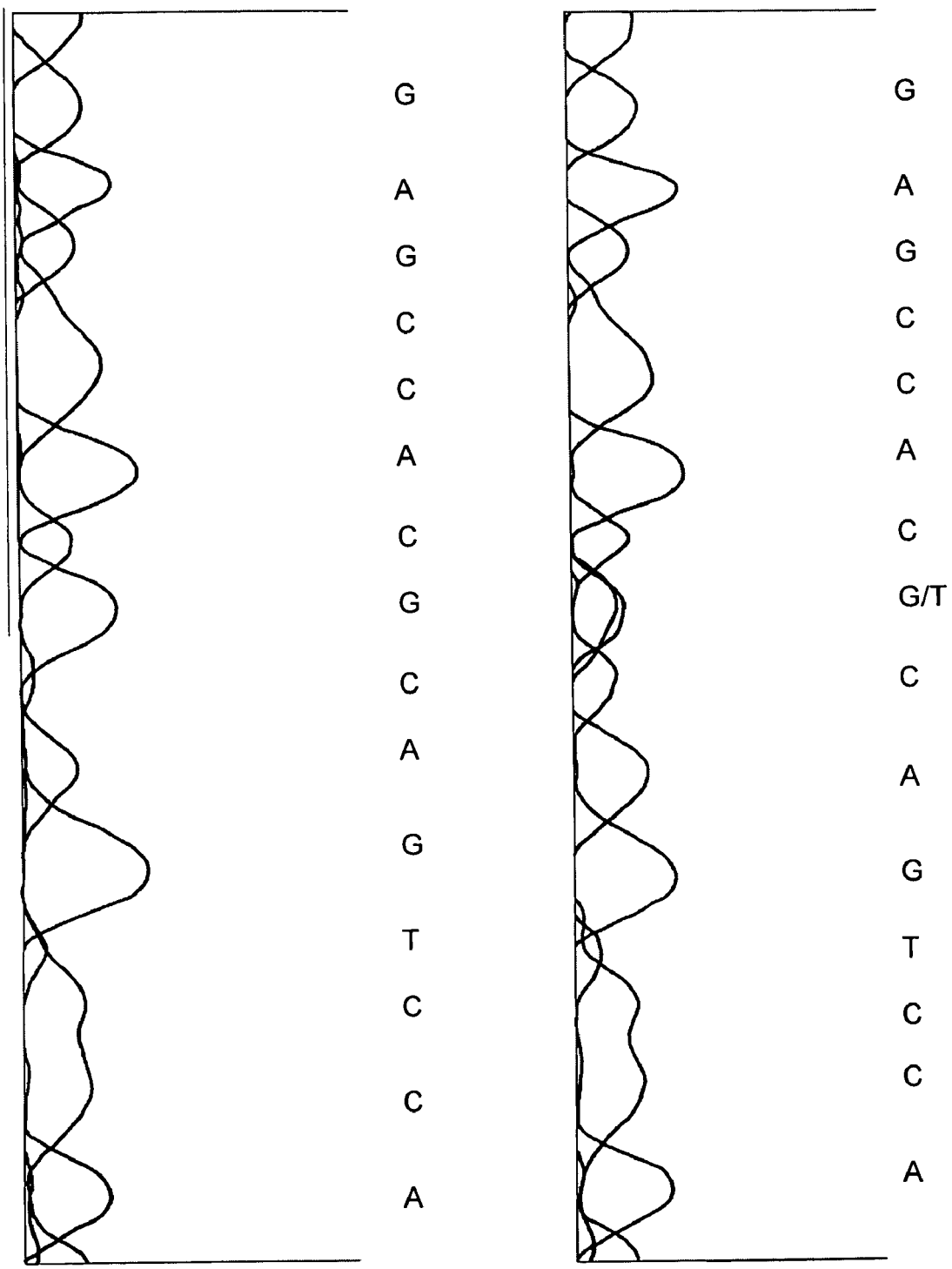
FIG. 2*c*. Automated florescent chromatograms representing the change in nucleic acids which direct (by the codon) the amino acid sequence of the gene; Ala 246 Glu.
Figure 2D:
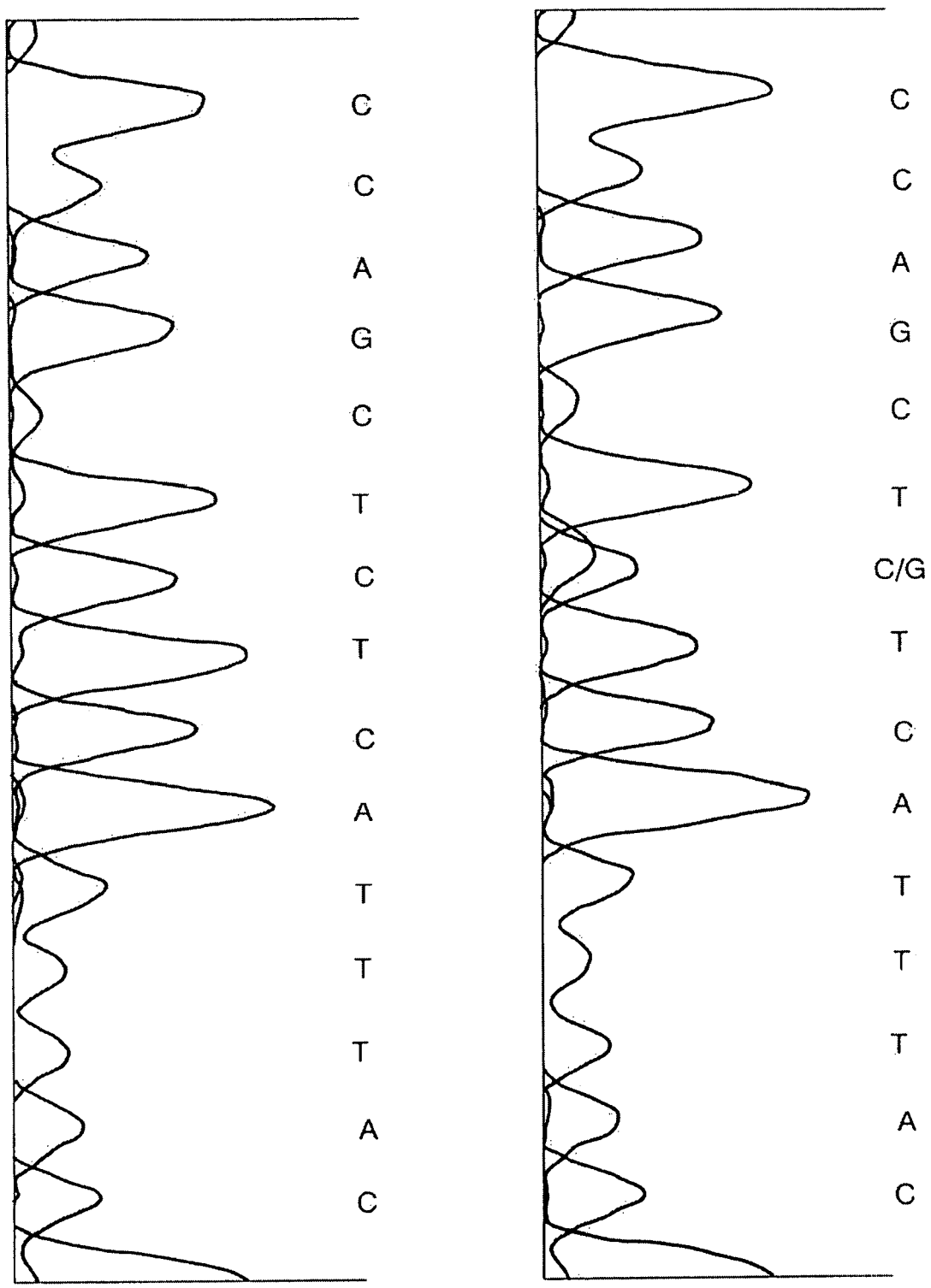
FIG. 2*d*. Automated florescent chromatograms representing the change in nucleic acids which direct (by the codon) the amino acid sequence of the gene; Leu 286 Val.
Figure 2E:
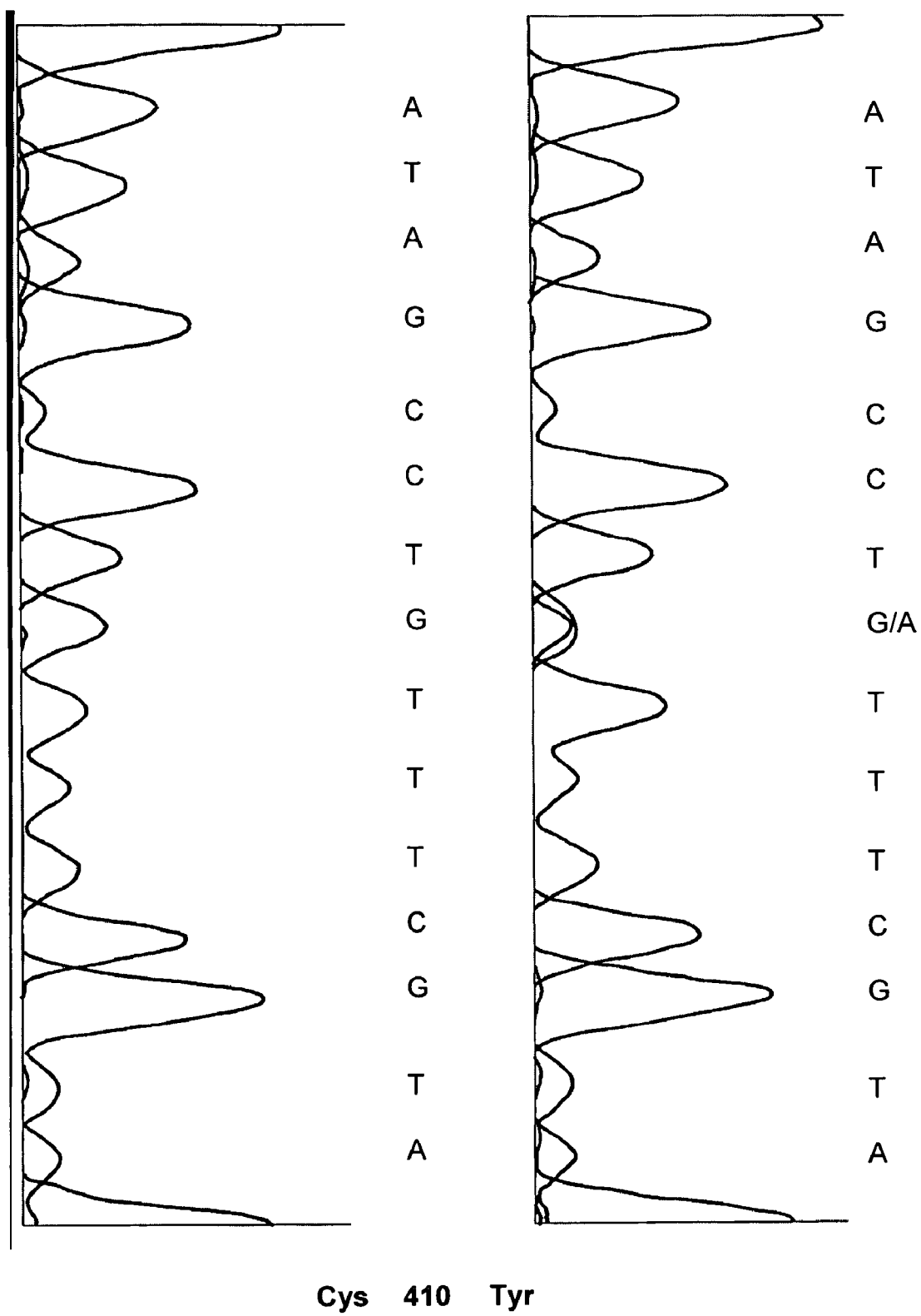
FIG. 2*e*. Automated florescent chromatograms representing the change in nucleic acids which direct (by the codon) the amino acid sequence of the gene; Cys 410 Tyr.

As an initial step toward cloning the AD3 gene a contig of overlapping genomic DNA fragments cloned into yeast artificial chromosome vectors, phage artificial chromosome vectors and cosmid vectors was constructed (FIG. 1b). FISH mapping studies using cosmids derived from the YAC clones 932c7 and 964f5 suggested that the interval most likely to carry the AD3 gene was at least five megabases in size. Because the large size of this minimal co-segregating region would make positional cloning strategies intactable, additional genetic pointers were sought which focused the search for the AD3 gene to one or more subregions within the interval flanked by D14S53 and D14S258. Haplotype analyses at the markers between D14S53 and D14S258 failed to detect statistically significant evidence for linkage disequilibrium and/or allelic association between the FAD trait and alleles at any of these markers, irrespective of whether the analyses were restricted to those pedigrees with early onset forms of FAD, or were generalized to include all pedigrees. This result was not unexpected given the diverse ethnic origins of our pedigrees. However, when pedigrees of similar ethnic descent were collated, direct inspection of the haplotypes observed on the disease bearing chromosomes segregating in different pedigrees of similar ethnic origin revealed two clusters of marker loci (Table 2). The first of these clusters located centromeric to D14S77 (D14S786, D14S277 and D14S268) and spanned the 0.95 Mb physical interval contained in YAC 78842 (depicted as region B in FIG. 1c). The second cluster was located telomeric to D14S77 (D14S43, D14S273, and D14S76) and spanned the ~1 Mb physical interval included within the overlapping YAC clones 964c2, 74163, 797d11 and part of 854f5 (depicted as region A in FIG. 1c). Identical alleles were observed in at least two pedigrees from the same ethnic origin (Table 2). As part of the strategy, it was reasoned that the presence of shared alleles at one of these groups of physically clustered marker loci might reflect the co-inheritance of a small physical region surrounding the ARMP gene on the original founder chromosome in each ethnic population. Significantly, each of the shared extended haplotypes were rare in normal Caucasian populations and allele sharing was not observed at other groups of markers spanning similar genetic intervals elsewhere on chromosome 14q24.3.

Transcription Mapping and Preliminary Analysis of Candidate Genes

To isolate expressed sequences encoded within both critical intervals, a direct selection strategy was used in involving immobilized, cloned, human genomic DNA as the hybridization target to recover transcribed sequences from primary complementary DNA pools derived from human brain mRNA (Rommens et al., 1993). Approximately 900 putative cDNA fragments of size 100 to 600 base pairs were recovered from regions A and B in FIG. 1c. These fragments were hybridized to Southern blots containing genomic DNAs from each of the overlapping YAC clones and genomic DNAs from humans and other mammals. This identified a subset of 151 clones which showed evidence for evolutionary conservation and/or for a complex structure which suggested that they were derived from spliced mRNA. The clones within this subset were collated on the basis of physical map location, cross-hybridization and nucleotide sequence, and were used to screen conventional human brain cDNA libraries for longer cDNAs. At least 19 independent cDNA clones over 1 kb in length were isolated and then aligned into a partial transcription map of the AD3 region (FIG. 1d). Only three of these transcripts corresponded to known characterized genes (cFOS, dihydrolipoamide succinyl transferase and latent transforming growth factor binding protein 2).

Recovery of Potential Candidate Genes

Each of the open reading frame portions of the candidate genes were recovered by RT-PCR from mRNA isolated from post-mortem brain tissue of normal control subjects and from either post-mortem brain tissue or cultured fibroblast cell lines of affected members of six pedigrees definitively linked to chromosome 14. The RT-PCR products were then screened for mutations using chemical cleavage and restriction endonuclease fingerprinting single-strand sequence conformational polymorphism methods (Saleeba and Cotton, 1993; Liu and Sommer, 1995), and by direct nucleotide sequencing. With one exception, all of the genes examined, although of interest, were not unique to affected subjects, and did not co-segregate with the disease. The single exception was the candidate gene represented by clone S182 which contained a series of nucleotide changes not observed in normal subjects, but which altered the predicted amino acid sequence in affected subjects. Although nucleotide sequence differences were also observed in some of the other genes, most were in the 3' untranslated regions and none were unique to Ad-affected subjects.

The remaining sequences, a subset of which are mapped in FIG. 1b together with additional putative transcriptional sequences not identified in FIG. 1c, are identified in the sequence listings as 14 through 43. The SEQ ID NOS:14 to 43 represent neighbouring genes or fragments of neighbouring genes adjacent the hARMP gene or possibly additional coding fragments arising from alternative splicing of the hARMP. SEQ ID NOS:44-126 and SEQ ID NOS:150-160 represent neighboring genomic fragments containing both exon and intron information. Such sequences are useful for creating primers, for creating diagnostic tests, creating altered regulatory sequences and use of adjacent genomic sequences to create better animal models.

Characterization of the hARMP Gene

Hybridization of the S182 clone to northern blots identified a transcript expressed widely in many areas of brain and peripheral tissues as a major 3.0 kb transcript and a minor transcript of 7.0 kb. Although the identity of the ~7.0 kb transcript is unclear, two observations suggest that the ~3.0 kb transcript represents an active product of the gene. Hybridization of the S182 clone to northern blots containing mRNA from a variety of murine tissues, including brain, identifies only a single transcript identical in size to the ~3.0 kb human transcript. All of the longer cDNA clones recovered to date (2.6-2.8 kb), which include both 5' and 3' UTRs and which account for the ~3.0 kb band on the northern blot, have mapped exclusively to the same physical region of chromosome 14. From these experiments the ~7.0 kb transcript could represent either a rare alternatively spliced or polyadenylated isoform of the ~3.0 transcript or could represent another gene with homology to S182.

The nucleotide sequence of the major transcript was determined from the consensus of eleven independent longer cDNA clones and from 3 independent clones recovered by standard 5' rapid amplification of cDNA ends and bears no significant homology to other human genes. The cDNA of the sequenced transcript is provided in SEQ ID NO:1 and the predicted amino acid sequence is provided in SEQ ID NO:2. The cDNA sequence of another sequenced human clone is also provided as SEQ ID NO:133 and its predicted amino acid sequence is provided in SEQ ID NO:134.

Analysis of the 5' end of multiple cDNA clones and RT-PCR products as well as corresponding genomic clones indicates that the 5' UTR is contained within at least two exons and that transcription either begins from two different start sites and/or that one of the early 5' untranslated exons is alternatively spliced (Table 6). The longest predicted open reading frame contains 467 amino acids with a small alternatively spliced exon of 4 amino acids at 25 codons from the putative start codon (Table 3). This putative start codon is the first in phase ATG located 63 bp downstream of a TGA stop codon and lacks a classical Kozak consensus sequences around the first two in-phase ATG sequences (Rogaer et al., in preparation). Like other genes lacking classical 'strong' start codons, the putative 5' UTR of the human transcripts are rich in GC.

Comparison of the nucleic acid and predicted amino acid sequences with available databases using the BLAST alignment paradigms revealed modest amino acid similarity with the *C. elegans* sperm integral membrane protein SPE-4 ($p=1.5e^{25}$, 24-37% identity over three groups of at least fifty residues) and weaker similarity to portions of several other membrane spanning proteins including mammalian chromogranin A and alpha subunit of mammalian voltage dependent calcium channels (Altschul et al., 1990). This clearly established that they are not the same gene. The amino-acid sequence similarities across putative transmembrane domains may occasionally yield alignment that simply arises from the limited number of hydrophobic amino acids, but there is also extended sequence alignment between S182 protein and SPE-4 at several hydrophillic domains. Both the putative S182 protein and SPE-4 are predicted to be of comparable size (467 and 465 residues, respectively) and to contain at least seven transmembrane domains with a large acidic domain preceding the final predicted transmembrane domains with a large acidic domain preceding the final predicted transmembrane domain. The S182 protein does have a longer predicted hydrophillic region at the N terminus.

Further investigation of the hARMP has revealed a host of sequence fragments which form the hARMP gene and include intron sequence information, 5' end untranslated sequence information and 3' end untranslated sequence information (Table 6). Such sequence fragments are identified in Sequence ID Nos. 6 to 13.

Mutations in the S182 Transcript

Direct sequencing of overlapping RT-PCR products spanning the 3.0 kb S182 transcript isolated from affected members of the six large pedigrees linked to chromosome 14 led to the discovery of eight missense mutations in each of the six pedigrees (Table 7, FIG. 2). Each of these mutations co-segregated with the disease in the respective pedigrees [FIGS. 3 (a) (b) (c) (d) (e)], and were absent from 142 unrelated neurologically normal subjects drawn from the same ethnic origins as the FAD pedigrees (284 unrelated chromosomes).

The location of the gene within the physical interval segregating with AD3 trait, the presence of eight different missense mutations which co-segregate with the disease train in six pedigrees definitively linked to chromosome 14, and the absence of these mutations in 284 independent normal chromosomes cumulatively confirms that the hARMP gene is the AD3 locus. Further biologic support for this hypothesis arises from the fact that the residues mutated in FAD kindreds are conserved in evolution (Table 3) and occur in domains of the protein which are also highly conserved, and from the fact that the S182 gene product is expressed at high levels in most regions of the brain including the most severely affected with AD.

The DNA sequence for the hARMP gene as cloned has been incorporated into a plasmid Bluescript. This stable vector has been deposited at ATCC under accession number 97124 on Apr. 28, 1995.

Several mutations in the hARMP gene have been identified which cause a severe type of familial Alzheimer's Disease. One, or a combination of these mutations may be responsible for this form of Alzheimer's Disease as well as several other neurological disorders. The mutations may be any form of nucleotide sequence alteration or substitution. Specific disease causing mutations in the form of nucleotide and/or amino acid substitutions have been located, although we anticipate additional mutations will be found in other families. Each of these nucleotide substitutions occurred within the putative ORF of the S182 transcript, and would be predicted to change the encoded amino acid at the following positions, numbering from the first putative initiation codon. The mutations are listed in respect of their nucleotide locations in SEQ ID NO:1 and SEQ ID NO:133 (an additional human clone) and amino acid locations in SEQ ID NO:2 and SEQ ID NO:134 (the additional human clone).

| | | | | |
|---|---|---|---|---|
| i) | 685, | A→C | Met 146 Leu |
| ii) | 737, | A→G | His 163 Arg |
| iii) | 986, | C→A | Ala 246 Glu |
| iv) | 1105, | C→G | Leu 286 Val |
| v) | 1478, | G→A | Cys 410 Tyr |
| vi) | 1027, | C→T | Ala 260 Val |
| vii) | 1102, | C→T | Ala 285 Val |
| viii) | 1422, | C→G | Leu 392 Val |

The Met146Leu, Ala246Glu and Cys410Tyr mutations have not been detected in the genomic DNA of affected members of the eight remaining small early onset autosomal dominant FAD pedigrees or six additional families in our collection which express late FAD onset. We predict that such mutations would not commonly occur in late onset FAD which has been excluded by genetic linkage studies from the more aggressive form of AD linked to chromosome 14q24.3 (St. George-Hyslop, P et al., 1992; Schellenberg et al., 1993). The His163Arg mutation has been found in the genomic DNA of affected members of one additional FAD pedigree for which positive but significant statistical evidence for linkage to 14 becomes established. Age of onset of affected members was consistent with affected individuals from families linked to chromosome 14.

Figure 3A:
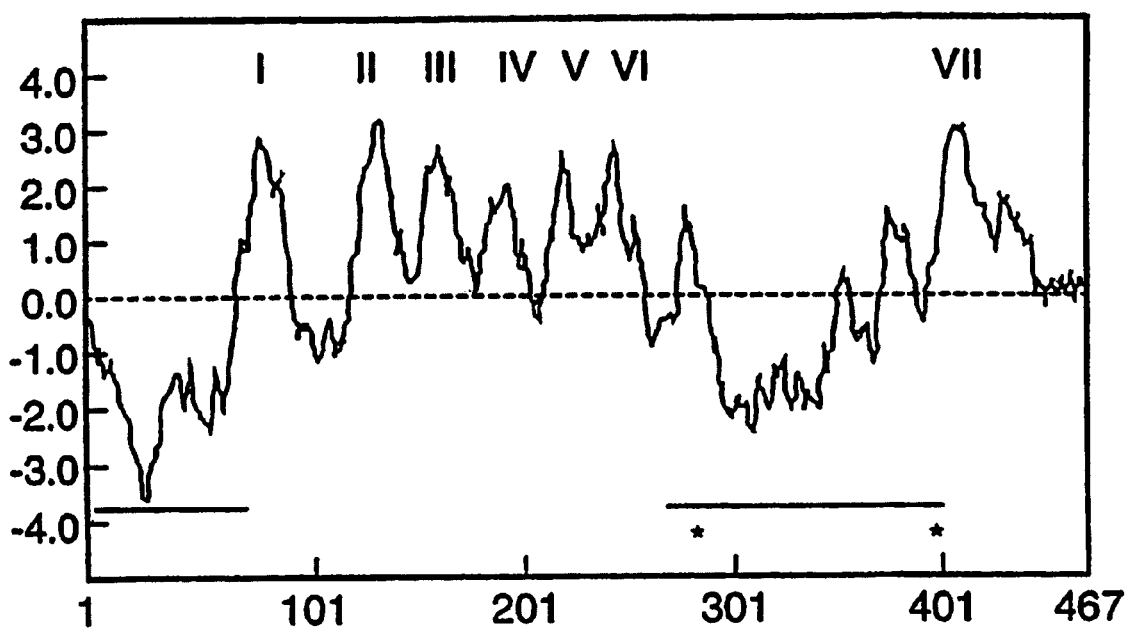
FIG. 3*a*. Hydropathy plot of the putative ARMP protein.

Mutations Ala260Val, Ala285Val, and Leu392Val all occur within the acidic hydrophilic loop between putative transmembrane 6 (TM6) and transmembrane (TM7) (FIG. 3A). Two of the mutations (A260V; A285V) and the L286V mutation are also located in the alternative spliced domain.

All eight of the mutations can be assayed by a variety of strategies (direct nucleotide sequencing, allele specific oligos, ligation polymerase chain reaction, SSCP, RFLPs etc.) using RT-PCR products representing the mature mRNA/cDNA sequence or genomic DNA. Allele specific oligos were chosen for assaying the mutations. For the A260V and the A285V mutations, genomic DNA carrying the exon was amplified using the same PCR primers and methods as for the L286V mutation. PCR products were then denatured and slot blotted to duplicate nylon membranes using the slot blot protocol described for the C410T mutation.

Of all of the nucleotide substitutions co-segregated with the disease in their respective pedigrees, none were seen in asymptomatic family members aged more than two standard deviations beyond the mean age of onset, and none were present on 284 chromosomes from unrelated neurologically normal subjects drawn from comparable ethnic origins.

Identification of an Alternative Splice Form of the ARMP Gene Product

During sequencing studies of RT-PCR products for the ARMP gene recovered from a variety of tissues, it was discovered that some peripheral tissues (principally white blood cells) demonstrated two alternative splice forms of the ARMP gene. One form is identical to the (putatively 467 amino acid) isoform constitutatively expressed in all brain regions. The alternative splice form results from the exclusion of the segment of the cDNA between base pairs 1018 and 1116 inclusive, and results in a truncated isoform of the ARMP protein wherein the hydrophobic part of the hydrophilic acidically-charged loop immediately C-terminal to TM6 is removed. This alternatively spliced isoform therefore is characterized by preservation of the sequence N-terminal to and including the tyrosine at position 256, changing of the aspartate at 257 to alanine, and splicing on to the C-terminal part of the protein from and including tyrosine 291. Such splicing differences are often associated with important functional domains of the proteins. This argues that this hydrophilic loop (and consequently the N-terminal hydrophilic loop with similar amino acid charge) is/are active functional domains of the ARMP product and thus sites for therapeutic targeting.

ARMP Protein

With respect to DNA SEQ ID NO. 1 and DNA SEQ ID NO:133, analysis of the sequence of overlapping cDNA clones predicted an ORF protein of 467 amino acids when read from the first in phase ATG start codon and a molecular mass of approximately 52.6 kDa as later described, due to either polymorphisms in the protein or alternate splicing of the transcript, the molecular weight of the protein can vary due to possible substitutions or deletions of amino acids.

The analysis of predicted amino acid sequence using the Hopp and Woods algorithm suggested that the protein product is a multispanning integral membrane protein such as a receptor, a channel protein, or a structural membrane protein. The absence of recognizable signal peptide and the paucity of glycoslyation sites are noteworthy, and the hydropathy profile suggests that the protein is less likely to be a soluble protein with a highly compact three-dimensional structure.

The protein may be a cellular protein with a highly compact three dimensional structure in which respect is may be similar to APOE which is also related to Alzheimer's Disease. In light of this putative functional role, it is proposed that this protein be labeled as the Alzheimer Related Membrane Protein (ARMP). The protein also contains a number of potential phosphorylation sites, one of which is the consensus site for MAPkinase which is also involved in the hyperphosphorlyation of tau during the normal conversion of normal tau to neurofibrillary tangles. This consensus sequence may provide a common putative pathway linking this protein and other known biochemical aspects of Alzheimer's Disease and would represent a likely therapeutic target. Review of the protein structure reveals two sequence YTPF (residues 115-119) SEQ ID NO:161 and STPE (residues 353-356) SEQ ID NO:162 which represent the 5/T-P motif which is the MAP kinase consensus sequence. Several other phosphorylation sites exist with consensus sequences for Protein Kinase C activity. Because protein kinase C activity is associated with differences in the metabolism of APP which are relevant to Alzheimer's Disease, these sites on the ARMP protein and homologues are sites for therapeutic targeting.

The N-terminal is characterized by a highly hydrophilic acid charged domain with several potential phosphorylation domains, followed sequentially by a hydrophobic membrane spanning domain of 19 residues; a charged hydrophilic loop, then five additional hydrophobic membrane spanning domains interspersed with short (5-20 residue) hydrophilic domains; an additional larger acidic hydrophilic charged loop, and then at least one and possibly two other hydrophobic potentially membrane spanning domains culminating in a polar domain at the C-terminus (Table 4 and FIG. 3B). The presence of seven membrane spanning domains is characteristic of several classes of G-coupled receptor proteins but is also observed with other proteins including channel proteins.

Comparison of the nucleic acid and predicted amino acid sequences with available databases using the BLAST alignment paradigms revealed amino acid similarity with the *C. elegans* sperm integral membrane protein spe-4 and a similarity to several other membrane spanning proteins including mammalian chromogranin A and the α-subunit of mammalian voltage dependent calcium channels.

The similarity between the putative products of the spe-4 and ARMP genes implies that they may have similar activities. The SPE-4 protein of *C. elegans* appears to be involved in the formation and stabilization of the fibrous body-membrane organelle (FBMO) complex during spermatogenesis. The FBMO is a specialized Golgi-derived organelle, consisting of a membrane bound vesicle attached to and partly surrounding a complex of parallel protein fibers and may be involved in the transport and storage of soluble and membrane-bound polypeptides. Mutations in spe-4 disrupt the FBMO complexes and arrest spermatogenesis. Therefore the physiologic function of spe-4 may be either to stabilize interactions between integral membrane budding and fusion events, or to stabilize interactions between the membrane and fibrillary proteins during the intracellular transport of the FBMO complex during spermatogenesis. Comparable functions could be envisaged for the ARMP. The ARMP could be involved either in the docking of other membrane-bound proteins such as βAPP, or the axonal transport and fusion budding of membrane-bound vesicles during protein transport such as in the golgi apparatus or endosome-lysosome system. If correct, then mutations might be expected to result in aberrant transport and processing of βAPP and/or abnormal interactions with cytoskeletal proteins such as the microtubule-associated protein Tau. Abnormalities in the intracellular and in the extracellular disposition of both βAPP and Tau are in fact an integral part of the neuropathologic features of Alzheimer's Disease. Although the location of the ARMP mutations in highly conserved residues within conserved domains of the putative proteins suggests that they are pathogenic, at least three of these mutations are conservative which is commensurate with the onset of disease in adult life. Because none of the mutations observed so far are deletions or nonsense mutations that would be expected to cause a loss of function, we cannot predict whether these mutations will have a dominant gain-of-function effect and promote aberrant processing of βAPP or a dominant loss-of-function effect causing arrest of normal βAPP processing.

An alternative possibility is that the ARMP gene product may represent a receptor or channel protein. Mutations of such proteins have been causally related to several other dominant neurologic disorders in both vertebrate (e.g., Malignant hyperthermia, hyperkalemic periodic paralysis in humans) and in invertebrate organisms (deg-1(d) mutants in *C. elegans*). Although the pathology of these other disorders does not resemble that of Alzheimer's Disease there is evidence for functional abnormalities in ion channels in Alzheimer's Disease. For example, anomalies have been reported in the tetra-ethylammonium-sensitive 113pS potassium channel and in calcium homeostasis. Perturbations in transmembrane calcium fluxes might be especially relevant in view of the weak homology between S182 and the α-ID subunit of voltage-dependent calcium channels and the observations that increases in intracellular calcium in cultured cells can replicate some of the biochemical features of Alzheimer's Disease such as alteration in the phosphorylation of Tau-microtubule-associated protein and increased production of Aβ peptides.

As mentioned purified normal ARMP protein is characterized by a molecular weight of 52.6 kDa. The normal ARMP protein, substantially free of other proteins, is encoded by the aforementioned SEQ ID NO:1 and SEQ ID NO:133. As will be later discussed, the ARMP protein and fragments thereof may be made by a variety of methods. Purified mutant ARMP protein is characterized by FAD-associated phenotype (necrotic death, apoptic death, granulovascular degeneration, neurofibrillary degeneration, abnormalities or changes in the metabolism of APP, and $Ca^{2+}$, $K^+$, and glucose, and mitochondrial function and energy metabolism neurotransmitter metabolism, all of which have been found to be abnormal in human brain, and/or peripheral tissue cells in subjects with Alzheimer's Disease) in a variety of cells. The mutant ARMP, free of other proteins, is encoded by the mutant DNA sequence.

Description of the E5-1 Gene, a Homologue of the ARMP Gene

A gene, E5-1, with substantial nucleotide and amino acid homology to the ARMP gene was identified by using the nucleotide sequence of the cDNA for ARMP to search data bases using the BLASTN paradigm of Atschul et al., 1990. Three expressed sequence tagged sites (ESTs) identified by accession numbers T03796, R14600, and R05907 were located which had substantial homology ($p<1.0\,e^{-100}$, greater than 97% identity over at least 100 contiguous base pairs).

Oligonucleotide primers were produced from these sequences and used to generate PCR products by reverse transcriptase PCR(RT-PCR). These short RT-PCR products were partially sequenced to confirm their identity with the sequences within the data base and were then used as hybridization probes to screen full-length cDNA libraries. Several different cDNA's ranging in size from 1 Kb to 2.3 Kb were recovered from a cancer cell cDNA library (CaCo-2) and from a human brain cDNA library (E5-1, G1-1, cc54, cc32).

The nucleotide sequence of these clones confirmed that all were derivatives of the same transcript (designated E5-1). A plasmid including this nucleic acid was deposited with the ATCC under the terms of the Budapest Treaty on Jun. 28, 1995 and has been assigned ATCC accession number 97214.

The gene encoding the E5-1 transcript mapped to human chromosome 1 using hybrid mapping panels and to two clusters of CEPH MegaYAC clones which have been placed upon a physical contig map (YAC clones 750g7, 921d12 mapped by FISH to 1q41; and YAC clone 787g12 which also contains an EST of the leukemia associated phosphoproteins (LAP18) gene which has been mapped to 1p36.1-p35) (data not shown).

Hybridization of the E5-1 cDNA clones to Northern Blots detected an ~2.3 kilobase mRNA band in many tissues including regions of the brain, as well as a ~2.6 K.b mRNA band in muscle, cardiac muscle and pancreas (FIG. 7).

In skeletal muscle, cardiac muscle and pancreas, the E5-1 gene is expressed at relatively higher levels than in brain and as two different transcripts of ~2.3 Kb and ~2.6 Kb. Both of the E5-1 transcripts have sizes clearly distinguishable from that of the 2.7 Kb ARMP transcript, and did not cross-hybridize with ARMP probes at high stringency. The cDNA sequence of the E5-1 gene is identified as SEQ ID NO:137.

The longest ORF within the E5-1 cDNA consensus nucleotide sequence predicts a polypeptide containing 448 amino acids (numbering from the first in-phase ATG codon which was surrounded by a GCC-agg-GCt-ATG-c Kozak consensus sequence) (SEQ ID NO:138).

A comparison of the amino acid sequences of hARMP and E5-1 homologue protein are shown in Table 8. Identical residues are indicated by vertical lines. The locations of mutations in the E5-1 gene are indicated by downward pointing arrows. The locations of the mutations in the hARMP gene are indicated by upward pointing arrows. Putative TM domains are in open ended boxes. The alternatively spliced exons are denoted by superscripted (E5-1) or subscripted (hARMP) "*".

BLASTP alignment analyses also detected significant homology with SPE-4 of *C. elegans* (P=3.5e−26; identity=20-63% over five domains of at least 22 residues), and weak homologies to brain sodium channels (alpha III subunit) and to the alpha subunit of voltage dependent calcium channels from a variety of species (P=0.02; identities 20-28% over two or more domains each of at least 35 residues) (Atschul, 1990). These alignments are similar to those described above for the ARMP gene. However, the most striking homology to the E5-1 protein was found with the amino acid sequence predicted for ARMP. ARMP and E-51 proteins share 63% overall amino acid sequence identity, and several domains display virtually complete identity (Table 8). Furthermore, all eight residues mutated in ARMP in subjects with AD3 are conserved in the E5-1 protein (Table 8). As would be expected, hydrophobicity analyses suggest that both proteins also share a similar structural organization.

The similarity was greatest in several domains of the protein corresponding to the intervals between transmembrane domain 1 (TM1) and TM6, and from TM7 to the C-terminus of the ARMP gene. The main difference from ARMP is a difference in the size and amino acid sequence of the acidically-charged hydrophilic loop in the position equivalent to the hydrophilic loop between transmembrane domains TM6 and TM7 in the ARMP protein and in the sequence of the N-terminal hydrophilic domains.

Figure 4:
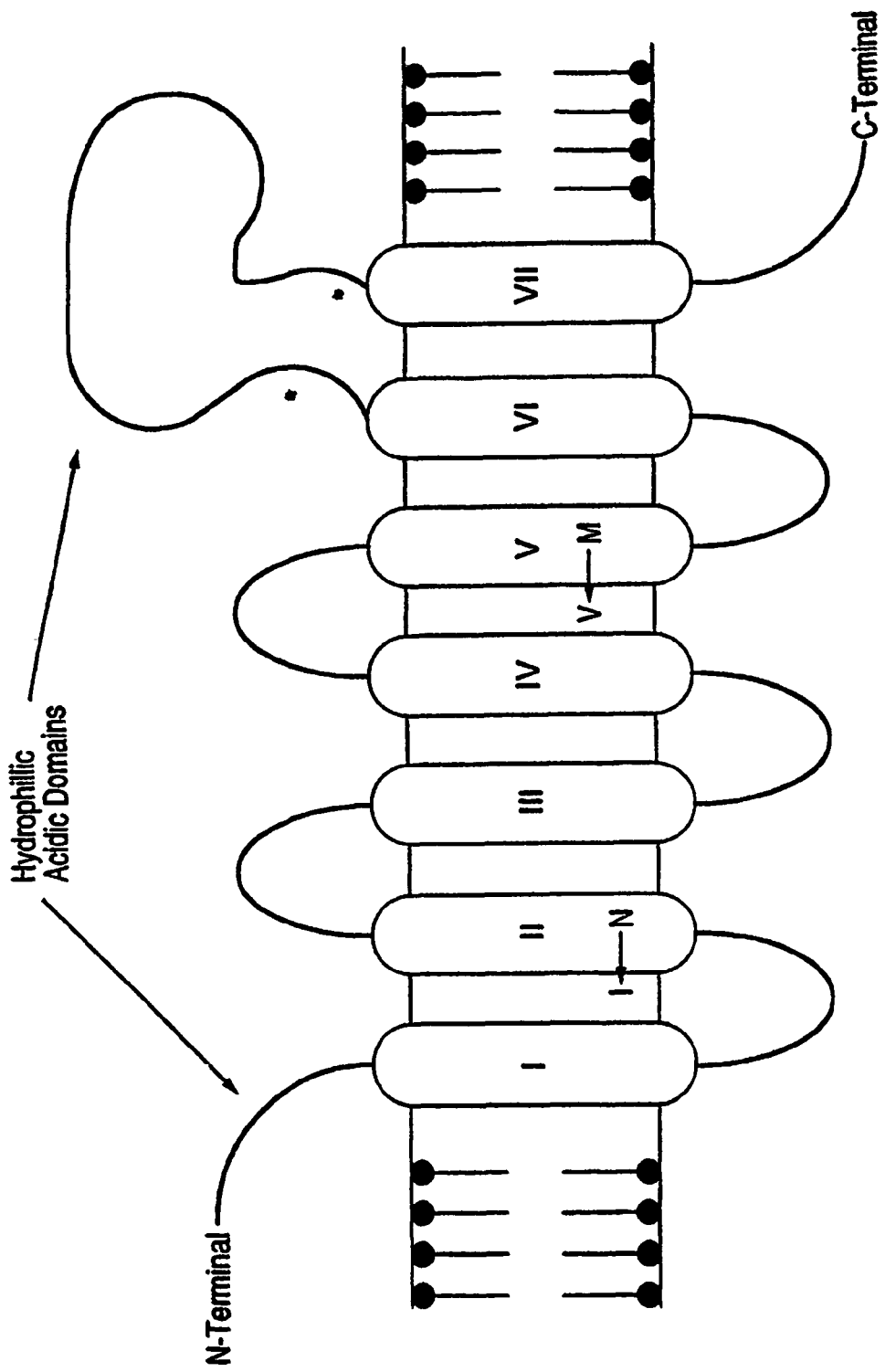
FIG. 4 shows the predicted structure of the E5-1 protein.

Thus, both proteins are predicted to possess seven hydrophobic putative transmembrane domains, and both proteins bear large acidic hydrophilic domains at the N-terminus and between TM6 and TM7 (FIGS. 3A and 4). A further similarity arose from analysis of RT-PCR products from brain and muscle RNA, which revealed that nucleotides 1153-1250 of the E5-1 transcript are alternatively spliced. These nucleotides encode amino acids 263-296, which are located within the TM6-TM7 loop domain of the putative E5-1 protein, and which share 94% sequence identity with the alternatively spliced residues 257-290 in ARMP.

The most noticeable differences between the two predicted amino acid sequences occur in the amino acid sequence in the central portion of the TM6-TM7 hydrophilic loop (residues 304-374 of ARMP; 301-355 of E5-1), and in the N-terminal hydrophilic domain (Table 8). By analogy, this domain is also less highly conserved between the murine and human ARMP genes (identity=47/60 residues), and shows no similarity with the equivalent region of SPE-4.

A splice variant of the E5-1 cDNA sequence identified as SEQ ID NO:137 has also been found in all tissues examined. This splice variant lacks the triplet GAA at nucleotide positions 1338-1340.

A further variant has been found in one normal individual whose E5-1 cDNA had C replacing T at nucleotide position 626, which does not change the amino acid sequence.

Mutations of the E5-1 Gene Associated with Alzheimer's Disease

The strong similarity between ARMP and the E5-1 gene product raised the possibility that the E5-1 gene might be the site of disease-causing mutations in some of a small number of early onset AD pedigrees in which genetic linkage studies have excluded chromosomes 14, 19 and 21. RT-PCR was used to isolate cDNAs corresponding to the E5-1 transcript from lymphoblasts, fibroblasts or post-mortem brain tissue of affected members of eight pedigrees with early onset familial AD (FAD) in which mutations in the β APP and ARMP gene had previously been excluded by direct sequencing studies.

Examination of these RT-PCR products detected a heterozygous A→G substitution at nucleotide 1080 in all four affected members of an extended pedigree of Italian origin (Flo10) with early onset, pathologically confirmed FAD (onset=50-70 yrs.) This mutation would be predicted to cause a Met→Val missense mutation at codon 239 (Table 8).

A second mutation (A→T at nucleotide 787) causing a Asn→Ile substitution at codon 141 was found in affected members of a group of related pedigrees of Volga German ancestry (represented by cell lines AG09369, AG09907, AG09952, and AG09905, Coriell Institute, Camden, N.J.). Significantly, one subject (AG09907) was homozygous for this mutation, an observation compatible with the in-bred nature of these pedigrees. Significantly, this subject did not have a significantly different clinical picture from those subjects heterozygous for the Arg14Ile mutation. Neither of the E5-1 gene mutations were found in 284 normal Caucasian controls nor were they present in affected members of pedigrees with the AD3 type of AD.

Both of these mutations would be predicted to cause substitutions of residues which are highly conserved within the ARMP/E5-1 gene family.

The finding of a gene whose product is predicted to share substantial amino acid and structural similarities with the ARMP gene product suggest that these proteins may be functionally related either as independent proteins with overlapping functions but perhaps with slightly different specific activities, as physically associated subunits of a multimeric polypeptide or as independent proteins performing consecutive functions in the same pathway.

The observation of two different missense mutations in conserved domains of the E5-1 protein in subjects with a familial form of AD argues that these mutations are, like those in the ARMP gene, causal to AD. This conclusion is significant because, while the disease phenotypes associated with mutations in the ARMP gene (onset 30-50 yrs., duration 10 years) are subtly different from that associated with mutations in the E5-1 gene (onset 40-70 years; duration up to 20 years), the general similarities clearly argue that the biochemical pathway subsumed by members of this gene family is central to the genesis of at least early onset AD. The subtle differences in disease phenotype may reflect a lower level of expression of the E5-1 transcript in the CNS, or may reflect a different role for the E5-1 gene product.

By analogy to the effects of ARMP mutations, E5-1 when mutated may cause aberrant processing of APP (Amyloid Precursor Protein) into Aβ peptide, hyperphosphorylation of Tau microtubule associated protein and abnormalities of intracellular calcium homeostasis. Interference with these anomalous interactions provides a potential therapy for AD.

Functional Domains of the ARMP Protein are Defined by Splicing Sites and Similarities within Other Members of a Gene Family The ARMP protein is a member of a novel class of transmembrane proteins which share substantial amino acid homology. The homology is sufficient that certain nucleotides probes and antibodies raised against one can identify other members of this gene family. The major difference between members of this family reside in the amino acid and nucleotide sequence homologous to the hydrophillic acid loop domain between putative transmembrane 6 and transmembrane 7 domains of the ARMP gene and gene product. This region is alternatively spliced in some non-neural tissues, and is also the site of several pathogenic disease-causing mutations in the ARMP gene. The variable splicing of this hydrophilic loop, the presence of a high-density of pathogenic mutations within this loop, and the fact that the amino acid sequences of the loop differs between members of the gene family suggest that this loop is an important functional domain of the protein and may confer some specificity to the physiologic and pathogenic interactions which the ARMP gene product undergoes because the N-terminal hydrophilic domain shares the same acidic charge and same orientation with respect to the membrane, it is very likely that these two domains share functionality either in a coordinated (together) or independent fashion (e.g., different ligands or functional properties). As a result everything said about the hydrophilic loop shall apply also to the N-terminal hydrophilic domain.

Knowledge of the specificity of the loop can be used to identify ligands and functional properties of the ARMP gene product (e.g. sites of interactions with APP, cytosolic proteins such as kinases, Tau, and MAP, etc.). Soluble recombinant fusion proteins can be made or the nucleotide sequence coding for amino acids within the loop or parts of the loop can be expressed in suitable vectors (yeast-2-hybrid, baculovirus, and phage-display systems for instance), and used to identify other proteins which interact with ARMP in the pathogenesis of Alzheimer's Disease and other neurological and psychiatric diseases. Therapies can be designated to modulate these interactions and thus to modulate Alzheimer's Disease and the other conditions associated with acquired or inherited abnormalities of the ARMP gene or its gene products. The potential efficacy of these therapies can be tested by analyzing the affinity and function of these interactions after exposure to the therapeutic agent by standard pharmacokinetic measurements of affinity (Kd and Vmax etc.) using synthetic peptides or recombinant proteins corresponding to functional domains of the ARMP gene (or its homologues). An alternate method for assaying the effect of any interactions involving functional domains such as the hydrophilic loop is to monitor changes in the intracellular trafficking and post-translational modification of the ARMP gene by in-situ hybridization, immunohistochemistry, Western blotting and metabolic pulse-chase labeling studies in the presence of and in the absence of the therapeutic agents. A third way is to monitor the effects of "downstream" events including (i) changes in the intracellular metabolism, trafficking and targeting of APP and its products; (ii) changes in second messenger event e.g., cAMP, intracellular $Ca^{++}$ protein kinase activities, etc.

Isolation and Purification of the ARMP Protein

The ARMP protein may be isolated and purified by methods selected on the basis of properties revealed by its sequence. Since the protein possesses properties of a membrane-spanning protein, a membrane fraction of cells in which the protein is highly expressed (e.g., central nervous system cells or cells from other tissues) would be isolated and the proteins removed by extraction and the proteins solubilized using a detergent.

Purification can be achieved using protein purification procedures such as chromatography methods (gel-filtration, ion-exchange and immunoaffinity), by high-performance liquid chromatography (RP-HPLC, ion-exchange HPLC, size-exclusion HPLC, high-performance chromatofocusing and hydrophobic interaction chromatography) or by precipitation (immunoprecipitation). Polyacrylamide gel electrophoresis can also be used to isolate the ARMP protein based on its molecular weight, charge properties and hydrophobicity.

Similar procedures to those just mentioned could be used to purify the protein from cells transfected with vectors containing the ARMP gene (e.g., baculovirus system, yeast expression systems, eukaryotic expression systems).

Purified protein can be used in further biochemical analyses to establish secondary and tertiary structure which may aid in the design of pharmaceuticals to interact with the protein, alter protein charge configuration or charge interaction with other proteins, lipid or saccharide moieties, alter its function in membranes as a transporter channel or receptor and/or in cells as an enzyme or structural protein and treat the disease.

The protein can also be purified by creating a fusion protein by legating the ARMP cDNA sequence to a vector which contains sequence for another peptide (e.g., GST-glutathionine succinyl transferase). The fusion protein is expressed and recovered from prokaryotic (e.g., bacterial or baculovirus) or eukaryotic cells. The fusion protein can then be purified by affinity chromatography based upon the fusion vector sequence. The ARMP protein can then be further purified from the fusion protein by enzymatic cleavage of the fusion protein.

Isolating Mouse ARMP Gene

In order to characterize the physiological significance of the normal and mutant hARMP gene and gene products in a transgenic mouse model it was necessary to recover a mouse homologue of the hARMP gene. We recovered a murine homologue for the hARMP gene by screening a mouse cDNA library with a labelled human DNA probe and in this manner recovered a 2 kb partial transcript (representing the 3' end of the gene) and several RT-PCR products representing the 5' end. Sequencing of the consensus cDNA transcript of the murine homologue revealed substantial amino acid identity. The sequence cDNA is identified in SEQ ID NO:3 and the predicted amino acid sequence is provided in SEQ ID NO:4. Further sequencing of the mouse cDNA transcript has provided the sequence of the complete coding sequence identified as SEQ ID NO:135 and the predicted amino acid sequence from this sequence is provided in SEQ ID NO:136. More importantly, all of the amino acids that were mutated in the FAD pedigrees were conserved between the murine homologue and the normal human variant (Table 3). This conservation of the ARMP gene as is shown in Table 3, indicates that an orthologous gene exists in the mouse (mARMP), and it is now possible to clone mouse genomic libraries using human ARMP probes. This will also make it possible to identify and characterize the ARMP gene in other species. This also provides evidence of animals with various disease states or disorders currently known or yet to be elucidated.

Transgenic Mouse Model

The creation of a mouse model for Alzheimer's Disease is important to the understanding of the disease and for the testing of possible therapies. Currently no unambiguous viable animal model for Alzheimer's Disease exists.

There are several ways in which to create an animal model for Alzheimer's Disease. Generation of a specific mutation in the mouse gene such as the identified hARMP gene mutations is one strategy. Secondly, we could insert a wild type human gene and/or humanize the murine gene by homologous recombination. Thirdly, it is also possible to insert a mutant (single or multiple) human gene as genomic or minigene cDNA constructs using wild type or mutant or artificial promoter elements. Fourthly, knock-out of the endogenous murine genes may be accomplished by the insertion of artificially modified fragments of the endogenous gene by homologous recombination. The modifications include insertion of mutant stop codons, the deletion of DNA sequences, or the inclusion of recombination elements (lcx p sites) recognized by enzymes such as Cre recombinase.

To inactivate the mARMP gene chemical or x-ray mutagenesis of mouse gametes, followed by fertilization, can be applied. Heterozygous offspring can then be identified by Southern blotting to demonstrate loss of one allele by dosage, or failure to inherit one parental allele using RFLP markers.

To create a transgenic mouse a mutant version of hRMP or mARMP can be inserted into a mouse germ line using standard techniques of oocyte microinjection or transfection or microinjection into stem cells. Alternatively, if it is desired to inactivate or replace the endogenous mARMP gene, homologous recombination using embryonic stem cells may be applied.

For oocyte injection, one or more copies of the mutant or wild type ARMP gene can be inserted into the pronucleus of a just-fertilized mouse oocyte. This oocyte is then reimplanted into a pseudo-pregnant foster mother. The liveborn mice can then be screened for integrants using analysis of tail DNA for the presence of human ARMP gene sequences. The transgene can be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the mutant or wild type hARMP. In this method, the mutant or wild type hARMP is inserted into a retroviral vector which is used to directly infect mouse embryos during the early stages of development to generate a chimera, some of which will lead to germline transmission. Similar experiments can be conducted in the cause of mutant proteins, using mutant murine or other animal ARMP gene sequences.

Homologous recombination using stem cells allows for screening of gene transfer cells to identify the rare homologous recombination events. Once identified, these can be used to generate chimeras by injection of mouse blastocysts, and a proportion of the resulting mice will show germline transmission from the recombinant line. This methodology is especially useful if inactivation of the mARMP gene is desired. For example, inactivation of the mARMP gene can be done by designing a DNA fragment which contains sequences from a mARMP exon flanking a selectable marker. Homologous recombination leads to the insertion of the marker sequences in the middle of an exon, inactivating the mARMP gene. DNA analysis of individual clones can then be used to recognize the homologous recombination events.

It is also possible to create mutations in the mouse germline by injecting oligonucleotides containing the mutation of interest and screening the resulting cells by PCR.

This embodiment of the invention has the most significant commercial value as a mouse model for Alzheimer's Disease. Because of the high percentage of sequence conservation between human and mouse it is contemplated that an orthologous gene will exist also in many other species. It is thus contemplated that it will be possible to generate other animal models using similar technology.

Screening and Diagnosis for Alzheimer's Disease General Diagnostic Uses of the ARMP Gene and Gene Product The ARMP gene and gene products will be useful for diagnosis of Alzheimer's Disease, presenile and senile dementias, psychiatric diseases such as schizophrenia, depression, etc., and neurologic diseases such as stroke and cerebral hemorrhage—all of which are seen to a greater or lesser extent in symptomatic subjects bearing mutations in the ARMP gene or in the APP gene. Diagnosis of inherited cases of these diseases can be accomplished by analysis of the nucleotide sequence (including genomic and cDNA sequences included in this patent). Diagnosis can also be achieved by monitoring alterations in the electrophoretic mobility and by the reaction with specific antibodies to mutant or wild-type ARMP gene products, and by functional assays demonstrating altered function of the ARMP gene product. In addition, the ARMP gene and ARMP gene products can be used to search for inherited anomalies in the gene and/or its products (as well as those of the homologous gene) and can also be used for diagnosis in the same way as they can be used for diagnosis of non-genetic cases.

Diagnosis of non-inherited cases can be made by observation of alterations in the ARMP transcription, translation, and post-translational modification and processing as well as alterations in the intracellular and extracellular trafficking of ARMP gene products in the brain and peripheral cells. Such changes will include alterations in the amount of ARMP messenger RNA and/or protein, alteration in phosphorylation state, abnormal intracellular location/distribution, abnormal extracellular distribution, etc. Such assays will include: Northern Blots (with ARMP-specific and ARMP non-specific nucleotide probes which also cross-react with other members of the gene family), and Western blots and enzyme-linked immunosorbent assays (ELISA) (with antibodies raised specifically to: ARMP; to various functional domains of ARMP; to other members of the homologous gene family; and to various post-translational modification states including glycosylated and phosphorylated isoforms). These assays can be performed on peripheral tissues (e.g., blood cells, plasma, cultured or other fibroblast tissues, etc.) as well as on biopsies of CNS tissues obtained antimortem or postmortem, and upon cerebrospinal fluid. Such assays might also include in-situ hybridization and immunohistochemistry (to localized messenger RNA and protein to specific subcellular compartments and/or within neuropathological structures associated with these diseases such as neurofibrillary tangles and amyloid plaques).

Screening for Alzheimer's Disease

Screening for Alzheimer's Disease as linked to chromosome 14 may now be readily carried out because of the knowledge of the mutations in the gene.

People with a high risk for Alzheimer's Disease (present in family pedigree) or, individuals not previously known to be at risk, or people in general may be screened routinely using probes to detect the present of a mutant ARMP gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to mutant sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of these mutant sequences are then visualized using methods such as autoradiography, fluorometry, or calorimetric reaction. Examples of suitable PCR primers which are useful for example in amplifying portions of the subject sequence containing the aforementioned mutations are set out in Table 5. This table also sets out the change in enzyme site to provide a useful diagnostic tool as defined herein.

Direct DNA sequencing reveals sequence differences between normal and mutant ARMP DNA. Cloned DNA segments may be used as probes to detect specific DNA segments. PCR can be used to enhance the sensitivity of this method. PCR is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as ligation-mediated PCR, anchored PCR and enzymatic amplification as would be understood by those skilled in the art.

Sequence alterations may also generate fortuitous restriction enzyme recognition sites which are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized under UV light in the presence of ethidium bromide after gel electrophoresis.

Genetic testing based on DNA sequence differences may be achieved by detection of alteration in electrophoretic mobility of DNA fragments in gels. Small sequence deletions and insertions can be visualized by high resolution gel electrophoresis. Small deletions may also be detected as changes in the migration pattern of DNA heteroduplexes in non-denaturing gel electrophoresis. Alternatively, a single base substitution mutation may be detected based on differential PCR product length in PCR. The PCR products of the normal and mutant gene could be differentially detected in acrylamide gels.

Nuclease protection assays (S1 or ligase-mediated) also reveal sequence changes at specific location.

Alternatively, to confirm or detect a polymorphism restriction mapping changes ligated PCR, ASO, REF-SSCP chemical cleavage, endonuclease cleavage at mismatch sites and SSCP may be used. Both REF-SSCP and SSCP are mobility shift assays which are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive decay, spectrophotometry, and fluorometry may also be used to identify specific individual genotypes. Finally, mutations can be detected by direct nucleotide sequencing.

According to an embodiment of the invention, the portion of the cDNA or genomic DNA segment that is informative for a mutation, can be amplified using PCR. For example, the DNA segment immediately surrounding the C410Y mutation acquired from peripheral blood samples from an individual can be screened using the oligonucleotide primers 885 (tg-gagactggaacacaac) SEQ ID NO:127 and 893 (gtgtggccaggg-tagagaact) SEQ ID NO:128. This region would then be amplified by PCR, the products separated by electrophoresis, and transferred to membrane. Labelled oligonucleotide probes are then hybridized to the DNA fragments and autoradiography performed.

ARMP Expression

As an embodiment of the present invention, ARMP protein may be expressed using eukaryotic and prokaryotic expression systems. Eukaryotic expression systems can be used for many studies of the ARMP gene and gene product including determination of proper expression and post-translational modifications for full biological activity, identifying regulatory elements located in the 5' region of the ARMP gene and their role in tissue regulation of protein expression, production of large amounts of the normal and mutant protein for isolation and purification, to use cells expressing the ARMP protein as a functional assay system for antibodies generated against the protein or to test effectiveness of pharmacological agents, or as a component of a signal transduction system, to study the function of the normal complete protein, specific portions of the protein, or of naturally occurring and artificially produced mutant proteins.

Eukaryotic and prokaryotic expression systems were generated using two different classes of ARMP nucleotide cDNA sequence inserts. In the first class, termed full-length constructs, the entire ARMP cDNA sequence is inserted into the expression plasmid in the correct orientation, and includes both the natural 5' UTR and 3' UTR sequences as well as the entire open reading frame. The open reading frames bear a nucleotide sequence cassette which allows either the wild type open reading frame to be included in the expression system or alternatively, a single or a combination of double mutations can be inserted into the open reading frame. This was accomplished by removing a restriction fragment from the wild type open reading frame using the enzymes NarI and PflmI and replacing it with a similar fragment generated by reverse transcriptase PCR which bears the nucleotide sequence encoding either the Met146Leu mutation or the Hys163Arg mutation. A second restriction fragment was removed from the wild type normal nucleotide sequence for the open reading frame by cleavage with the enzymes PflmI and NcoI and replaced with restriction fragments bearing either nucleotide sequence encoding the Ala246Glu mutation, or the Ala260Val mutation or the Ala285Val mutation or the Leu286Val mutation, or the Leu392Val mutation, or the Cys410Tyr mutation. Finally, a third variant bearing combinations of either the Met146Leu or His 163Arg mutations in tandem with the remaining mutations, was made by linking the NarI-PflmI fragment bearing these mutations and the PflmI-NcoI fragments bearing the remaining mutations.

A second variant of cDNA inserts bearing wild type or mutant cDNA sequences was constructed by removing from the full-length cDNA the 5' UTR and part of the 3' UTR sequences. The 5' UTR sequence was replaced with a synthetic oligonucleotide containing a KpnI restriction site and a Kozak initiation site (oligonucleotide 969: ggtaccgccaccatgacagaggtacctgcac, SEQ ID NO:139). The 3' UTR was replaced with an oligonucleotide corresponding to position 2566 of the cDNA and bears an artificial EcoRI site (oligonucleotide 970: gaattcactggctgtagaaaaagac, SEQ ID NO:140). Mutant variants of this construct were then made by inserting the same mutant sequences described above at the NarI-PflmI fragment, and at the PsImI-NcoI sites described above.

For eukaryotic expressions, these various cDNA constructs bearing wild type and mutant sequences described above were cloned into the expression vector pZeoSV (invitrogen). For prokaryotic expression, two constructs have been made using the glutathione S-transferase fusion vector pGEX-kg. The inserts which have been attached to the GST fusion nucleotide sequence are the same nucleotide sequence described above (generated with the oligonucleotide primers 969, SEQ ID NO:139 and 970, SEQ ID NO:140) bearing either the normal open reading frame nucleotide sequence, or bearing a combination of single and double mutations as described above. This construct allows expression of the full-length protein in mutant and wild type variants in prokaryotic cell systems as a GST fusion protein which allows purification of the full length protein followed by removal of the GST fusion product by thrombin digestion. The second prokaryotic cDNA construct was generated to create a fusion protein with the same vector, and allows the production of the amino acid sequence corresponding to the hydrophilic acidic loop domain between TM6 and TM7 of the full-length protein, as either a wild type nucleotide sequence (thus a wild type amino acid sequence for fusion proteins) or as a mutant sequence bearing either the Ala285Val mutation, or the Leu286Val mutation, or the Leu392Val mutation. This was accomplished by recovering wild type or mutant sequence from appropriate sources of RNA using the oligonucleotide primers 989: ggatccggtccacttcgtatgctg, SEQ ID NO:141, and 990: tttttgaattcttaggctatggttgtgttcca, SEQ ID NO:142. This allows cloning of the appropriate mutant or wild type nucleotide sequence corresponding to the hydrophilic acid loop domain at the BamHI and the EcoRI sites within the pGEX-KG vector.

These prokaryotic expression systems allow the holo-protein or various important functional domains of the protein to be recovered as fusion proteins and then used for binding studies, structural studies, functional studies, and for the generation of appropriate antibodies.

Expression of the ARMP gene in heterologous cell systems can be used to demonstrate structure-function relationships. Ligating the ARMP DNA sequence into a plasmid expression vector to transfect cells is a useful method to test the proteins influence on various cellular biochemical parameters. Plasmid expression vectors containing either the entire, normal or mutant human or mouse ARMP sequence or portions thereof, can be used in vitro mutagenesis experiments which will identify portions of the protein crucial for regulatory function.

The DNA sequence can be manipulated in studies to understand the expression of the gene and its product, to achieve production of large quantities of the protein for functional analysis, for antibody production, and for patient therapy. The changes in the sequence may or may not alter the expression pattern in terms of relative quantities, tissue-specificity and functional properties. Partial or full-length DNA sequences which encode for the ARMP protein, modified or unmodified, may be ligated to bacterial expression vectors. E. coli can be used using a variety of expression vector systems, e.g., the T7 RNA polymerase/promoter system using two plasmids or by labeling of plasmid-encoded proteins, or by expression by infection with M13 Phage mGPI-2. E. coli vectors can also be used with Phage lamba regulatory sequences, by fusion protein vectors (e.g. lacZ and trpE), by maltose-binding protein fusions, and by glutathione-S-transferase fusion proteins, etc., all of which together with many other prokaryotic expression systems are widely available commercially.

Alternatively, the ARMP protein can be expressed in insect cells using baculoviral vectors, or in mammalian cells using vaccinia virus or specialized eukaryotic expression vectors. For expression in mammalian cells, the cDNA sequence may be ligated to heterlogous promoters, such as the simian varus (SV40) promoter in the pSV2 vector and other similar vectors and introduced into cultured eukaryotic cells, such as COS cells to achieve transient or long-term expression. The stable integration of the chimeric gene construct may be maintained in mammalian cells by biochemical selection, such as neomycin and mycophoenolic acid.

The ARMP DNA sequence can be altered using procedures such as restriction enzyme digestion, fill-in with DNA polymerase, deletion by exonuclease, extension by terminal deoxynucleotide transferase, ligation of synthetic or cloned DNA sequences and site-directed sequence alteration with the use of specific oligonucleotides together with PCR.

The cDNA sequence or portions thereof, or a mini gene consisting of a cDNA with an introl and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous ARMP gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

Using the techniques mentioned, the expression vectors containing the ARMP gene or portions thereof can be introduced into a variety of mammalian cells from other species or into non-mammalian cells.

The recombinant cloning vector, according to this invention, comprises the selected DNA of the DNA sequences of this invention for expression in a suitable host. The DNA is operatively linked in the vector to an expression control sequence in the recombinant DNA molecule so that normal and mutant ARMP protein can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cell which may be transfected with the vector of this invention may be selected from the group consisting of *E. coli, pseudomonas, bacillus subtillus, bacillus stearothermophilus*, or other bacili; other bacteria, yeast, fungi, insect, mouse or other animal, plant hosts, or human tissue cells.

For the mutant ARMP DNA sequence similar systems are employed to express and produce the mutant protein.

Antibodies to Detect ARMP

Antibodies to epitopes with the ARMP protein can be raised to provide information on the characteristics of the proteins. Generations of antibodies would enable the visualizations of the proteins in cells and tissues using Western blotting. In this technique, proteins are run on polyacrylamide gel and then transferred onto nitrocellulose membranes. These membranes are then incubated in the presence of the antibody (primary), then following washing are incubated to a secondary antibody which is used for detection of the protein-primary antibody complex. Following repeated washing, the entire complex is visualized using colourimetric or chemiluminescent methods.

Antibodies to the ARMP protein also allow for the use of immunocytochemistry and immunofluorescence techniques in which the proteins can be visualized directly in cells and tissues. This is most helpful in order to establish the subcellular location of the protein and the tissue specificity of the protein.

In order to prepare polyclonal antibodies, fusion proteins containing defined portions or all of the ARMP protein can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by various methods including affinity chromatography, Protein A-Sepharose, Antigen Sepharose, Anti-mouse-Ig-Sepharose. The sera can then be used to probe protein extracts run on a polyacrylamide gel to identify the ARMP protein. Alternatively, synthetic peptides can be made to the antigenic portions of the protein and used to inoculate the animals.

To produce monoclonal ARMP antibodies, cells actively expressing the protein are cultured or isolated from tissues and the cell membranes isolated. The membranes, extracts or recombinant protein extracts, containing the ARMP protein, are injected in Freund's adjuvant into mice. After being injected 9 times over a three week period, the mice spleens are removed and resuspended in a phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable line of clones is established which produce the antibody. The monoclonal antibody can then be purified by affinity chromatography using Protein A Sepharose, ion-exchange chromatography, as well as variations and combinations of these techniques.

In situ hybridization is another method used to detect the expression of ARMP protein. In situ hybridization relies upon the hybridization of a specifically labeled nucleic acid probe to the cellular RNA in individual cells or tissues. Therefore, it allows the identification of mRNA within intact tissues, such as the brain. In this method, oligonucleotides corresponding to unique portions of the ARMP gene are used to detect specific mRNA species in the brain.

In this method a rat is anesthetized and transcardially perfused with cold PBS, followed by perfusion with a formaldehyde solution. The brain or other tissues is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the primer is made by nick translation and incubated with the sectioned brain tissue. After incubation and air drying, the labeled areas are visualized by autoradiography. Dark spots on the tissue sample indicate hybridization of the probe with brain mRNA which demonstrates the expression of the protein.

Antibodies may also be used coupled to compounds for diagnostic and/or therapeutic uses such as radionuclides for imaging and therapy and liposomes for the targeting of compounds to a specific tissue location.

Isolation and Purification of E5-1 Protein

The E5-1 protein may be isolated and purified by the types of methods described above for the ARMP protein.

The protein may also be prepared by expression of the E5-1 cDNA described herein in a suitable host. The protein is a preferably expressed as a fusion protein by ligating its encoding cDNA sequence to a vector containing the coding sequence for another suitable peptide, e.g., GST. The fusion protein is expressed and recovered from prokaryotic cells such as bacterial or baculovirus cells or from eukaryotic cells. Antibodies to ARMP, by virtue of portions of amino acid sequence identity with E5-1, can be used to purify, attract and bind to E5-1 protein and vice versa.

Transgenic Mouse Model of E5-1 Related Alzheimer's Disease

An animal model of Alzheimer's Disease related to mutations of the E5-1 gene may be created by methods analogous to those described above for the ARMP gene.

Antibodies

Due to its structural similarity with the ARMP, the E5-1 protein may be used for the development of probes, peptides, or antibodies to various peptides within it which may recognize both the E5-1 and the ARMP gene and gene products, respectively. As a protein homologue for the ARMP, the E5-1 protein may be used as a replacement for a defective ARMP gene product. It may also be used to elucidate functions of the ARMP gene in tissue culture and vice versa.

Screening for Alzheimer's Disease Linked to Chromosome 1

Screening for Alzheimer's Disease linked to mutations of the E5-1 gene may now be conveniently carried out.

General screening methods are described above in relation to the described mutations in the ARMP gene. These described methods can be readily applied and adapted to detection of the described chromosome 1 mutations, as will be readily understood by those skilled in the art.

In accordance with one embodiment of the invention, the Asn141Ile mutation is screened for by PCR amplification of the surrounding DNA fragment using the primers:

```
                                           SEQ ID NO: 163
    1041: 5'-cattcactgaggacacacc (end-labelled)
    and SEQ ID NO: 164
    1042: 5'-tgtagagcaccaccaaga (unlabelled).
```

Any tissue with nucleated cell may be examined. The amplified products are separated by electrophoresis and an autoradiogram of the gel is prepared and examined for mutant bands.

In accordance with a further embodiment, the Met239Val mutation is screened for by PCR amplification of its surrounding DNA fragment using the primers:

```
    1034: 5'-gcatggtgtgcatccact       SEQ ID NO: 165
    and

1035: 5'-ggaccactctgggaggta.      SEQ ID NO: 166
```

The amplified products are separated and an autoradiogram prepared as described above to detect mutant bands.

The same primer sets may be used to detect the mutations by means of other methods such as SSCP, chemical cleavage, DGGE, nucleotide sequencing, ligation chain reaction and allele specific oligonucleotides. As will be understood by those skilled in the art, other suitable primer pairs may be devised and used.

In inherited cases, as the primary event, and in non-inherited cases as a secondary event due to the disease state, abnormal processing of E5-1, ARMP, APP or proteins reacting with E5-1, APP or ARMP, may occur. This can be detected as abnormal phosphorylation, glycoslyation, glycation amidation or proteolytic cleavage products in body tissues or fluids, e.g., CSF or blood.

Therapies

An important aspect of the biochemical studies using the genetic information of this invention is the development of therapies to circumvent or overcome the ARMP gene defect, and thus prevent, treat, control serious symptoms or cure the disease. In view of expression of the ARMP gene in a variety of tissues, one has to recognize that Alzheimer's Disease may not be restricted to the brain. Alzheimer's Disease manifests itself as a neurological disorder which in one of its forms is caused by a mutation in the ARMP gene, but such manifest may be caused by mutations in other organ tissues, such as the liver, releasing factors which affect the brain activity and ultimately cause Alzheimer's Disease. Hence, in considering various therapies, it is understood that such therapies may be targeted at tissue other than the brain, such as heart, placenta, lung, liver, skeletal muscle, kidney and pancreas, where ARMP is also expressed.

The effect of these mutations in E5-1 and ARMP is a gain of novel function which causes aberrant processing of (APP) Amyloid Precursor Protein into Aβ peptide, abnormal phosphorylation homeostasis, and abnormal apoptosis. Therapy to reverse this will be small molecules (drugs) recombinant proteins, etc. which block the aberrant function by altering the structure of the mutant proteins, etc. which block the aberrant function by altering the structure of the mutant protein, enhancing its metabolic clearance or inhibiting binding of ligands to the mutant protein, enhancing its metabolic clearance or inhibiting binding of ligands to the mutant protein, or inhibiting the channel function of the mutant protein. The same effect might be gained by inserting a second mutant protein by gene therapy similar to the correction of the "Deg 1(d)" and "Mec 4 (d)" mutations in C. elegans by insertion of mutant transgenes. Alternatively over expression of wild type E5-1 protein or wild type ARMP or both may correct the defect. This could be the administration of drugs or proteins to induce the transcription and translation or inhibit the catabolism of the native E5-1 and ARMP proteins. It could also be accomplished by infusion of recombinant proteins or by gene therapy with vectors causing expression of the normal protein at a high level.

Rationale for Therapeutic, Diagnostic, and Investigational Applications of the ARMP Gene and Gene Products as They Relate to the Amyloid Precursor Protein The Aβ peptide derivatives of APP are neurotoxic (Selkoe et al, 1994). APP is metabolized by passages through the Golgi network and then to secretory pathways via clathrin-coated vesicles with subsequent passage to the plasma membrane where the mature APP is cleaved by α-secretase to a soluble fraction (Protease Nexin II) plus a non-amyloidogenic C-terminal peptide (Selkoe et al. 1995, Gandy et al., 1993). Alternatively, mature APP can be directed to the endosome-lysosome pathway where it undergoes beta and gamma secretase cleavage to produce the Aβpeptides. The phosphorylation state of the cell determines the relative balance of α-secretase (non-amyloidogenic) or Aβ pathways (amyloidogenic pathway) (Gandy et al., 1993). The phosphorylation state of the cell can be modified pharmacologicially by phorbol esters, muscarinic agonists and other agents, and appears to be mediated by cytosolic factors (especially protein kinase C) acting upon an integral membrane protein in the Golgi network, which we propose to the ARMP, and members of the homologous family (all of which carry several phosphorylation consensus sequences for protein kinase C). Mutations in the ARMP gene will cause alterations in the structure and function of the ARMP gene product leading to defective interactions with regulatory elements (e.g., protein kinase C) or with APP, thereby promoting APP to be directed to the amyloidogenic endosome-lysosome pathway. Environmental factors (viruses, toxins, and aging, etc.) may also have similar effects on ARMP. To treat Alzheimer's Disease, the phosphorylation state of ARMP can be altered by chemical and biochemical agents (e.g. drugs, peptides and other compounds) which alter the activity of protein kinase C and other protein kinase, or which alter the activity of protein phosphatases, or which modify the availability of ARMP to be postranslationally modified. The interactions between kinases and phosphatases with the ARMP gene products (and the products of its homologues), and the interactions of the ARMP gene products with other proteins involved in the trafficking of the APP within the Golgi network can be modulated to decrease trafficking of Golgi vesicles to the endosome-lysosome pathway thereby promoting Aβ peptide production. Such compounds will include: peptide analogues of APP, ARMP, and homologues of ARMP as well as other interacting proteins, lipids, sugars, and agents which promote differential glycosylation of ARMP and its homologues; agents which alter the biologic half-life of messenger RNA or protein of ARMP and homologues including antibodies and antisense oligonucleotides; and agents which act upon ARMP transcription.

The effect of these agents in cell lines and whole animals can be monitored by monitoring: transcription; translation; post-translational modification of ARMP (e.g., phosphorylation or glycoslyation); and intracellular trafficking of ARMP and its homologues through various intracellular and extracellular compartments. Methods for these studies include Western and Northern blots; immunoprecipation after metabolic labeling (pulse-chase) with radio-labeled methionine and ATP, and immunohistochemistry. The effect of these agents can also be monitored using studies which examine the relative binding affinities and relative amounts of ARMP gene products in interactions with protein kinase C and/or APP using either standard binding affinity assays or co-precipitation and Western blots using antibodies to protein kinase C, APP or ARMP and its homologues. The effect of these agents can also be monitored by assessing the production of Aβ peptides by ELISA before and after exposure to the putative therapeutic agent (Huang et al., 1993). The effect can also be monitored by assessing the viability of cell lines after exposure to aluminum salts and to Aβ peptides which are through to be neurotoxic in Alzheimer's Disease. Finally, the effect of these agents can be monitored by assessing the cognitive function of animals bearing: their normal genotype at APP or ARMP homologues; bearing human APP transgenes (with or without mutations); or bearing human ARMP transgenes (with or without mutations); or a combination of all of these.

Rationale for Therapeutic, Diagnostic, and Investigational Applications of the ARMP Gene, the E5-1 Gene and their Products The ARMP gene product and the E5-1 gene product have amino acid sequence homology to human ion channel proteins and receptors. For instance, the E5-1 protein shows substantial homology to the human sodium channel α-subunit (E=0.18, P=0.16, identities=22-27% over two regions of at least 35 amino acid residues) using the BLASTP paradigm of Atschul et al. 1990. Other diseases (such as malignant hyperthermia and hyperkalemic periodic paralysis in humans and the neurodegenerative of mechanosensory neurons in *C. elegans*) arise through mutations in ion channels or receptor proteins. Mutation of the ARMP gene or the E5-1 gene could affect similar functions and lead to Alzheimer's Disease and other psychiatric and neurological diseases. Based upon this, a test for Alzheimer's Disease can be produced to detect an abnormal receptor or an abnormal ion channel function related to abnormalities that are acquired or inherited in the ARMP gene and its product or in one of the homologous genes such as E5-1 and their products. This test can be accomplished either in vivo or in vitro by measurements of ion channel fluxes and/or transmembrane voltage or current fluxes using patch clamp, voltage clamp and fluorescent dyes sensitive to intracellular calcium or transmembrane voltage. Defective ion channel or receptor function can also be assayed by measurements of activation of second messengers such as cyclic AMP, cGMP tyrosine kinases, phosphates, increases in intracellular $Ca^{2+}$ levels, etc. Recombinantly made proteins may also be reconstrued in artificial membrane systems to study ion channel conductance. Therapies which affect Alzheimer's Disease (due to acquired/inherited defects in the ARMP gene or E5-1 gene; due to defects in other pathways leading to this disease such as mutations in APP; and due to environmental agents) can be tested by analysis of their ability to modify an abnormal ion channel or receptor function induced by mutation in the ARMP gene or in one of its homologues. Therapies could also be tested by their ability to modify the normal function of an ion channel or receptor capacity of the ARMP gene products and its homologues. Such assays can be performed on cultured cells expressing endogenous normal or mutant ARMP genes/gene products or E5-1 genes/gene products. Such studies can be performed in addition on cells transfected with vectors capable of expressing ARMP, parts of the ARMP gene and gene product, mutant ARMP, E5-1 gene, parts of the E5-1 gene and gene product, mutant E5-1 gene or another homologue in normal or mutant form. Therapies for Alzheimer's Disease can be devised to modify an abnormal ion channel or receptor function of the ARMP gene or E5-1 gene. Such therapies can be conventional drugs, peptides, sugars, or lipids, as well as antibodies or other ligands which affect the properties of the ARMP or E5-1 gene product. Such therapies can also be performed by direct replacement of the ARMP gene and/or E5-1 gene by gene therapy. In the case of an ion channel, the gene therapy could be performed using either mini-genes (cDNA plus a promoter) or genomic constructs bearing genomic DNA sequences for parts or all of the ARMP gene. Mutant ARMP or homologous gene sequence might also be used to counter the effect of the inherited or acquired abnormalities of the ARMP gene as has recently been done for replacement of the mec 4 and deg 1 in *C. elegans* (Huang and Chalfie, 1994). The therapy might also be directed at augmenting the receptor or ion channel function of the homologous genes such as the E5-1 gene, in order that it may potentially take over the functions of the ARMP gene rendered defective by acquired or inherited defects. Therapy using antisense oligonucleotides to block the expression of the mutant ARMP gene or the mutant E5-1 gene, coordinated with gene replacement with normal ARMP or E5-1 gene can also be applied using standard techniques of either gene therapy or protein replacement therapy.

Protein Therapy

Treatment of Alzheimer's Disease can be performed by replacing the mutant protein with normal protein, or by modulating the function of the mutant protein. Once the biological pathway of the ARMP protein has been completely understood, it may also be possible to modify the pathophysiologic pathway (e.g., a signal transduction pathway) in which the protein participates in order to correct the physiological defect.

To replace the mutant protein with normal protein, or with a protein bearing a deliberate counterbalancing mutation it is necessary to obtain large amounts of pure ARMP protein or E5-1 protein from cultured cell systems which can express the protein. Delivery of the protein to the affected brain areas or other tissues can then be accomplished using appropriate packaging or administrating systems.

Gene Therapy

Gene therapy is another potential therapeutic approach in which normal copies of the ARMP gene are introduced into patients to successfully code for normal protein in several different affected cell types. The gene must be delivered to those cells in a form in which it can be taken up and code for sufficient protein to provide effective function. Alternatively, in some neurologic mutants it has been possible to prevent disease by introducing another copy of the homologous gene bearing a second mutation in that gene or to alter mutation, or use another gene to block its effect.

Retroviral vectors can be used for somatic cell gene therapy especially because of their high efficiency of infection and stable integration and expression. The targeted cells however must be able to divide and the expression of the levels of normal protein should be high because the disease is a dominant one. The full length ARMP gene can be cloned into a retroviral vector and driven from its endogenous promoter or from the retroviral long terminal repeat or from a promoter specific for the target cell type of interest (such as neurons).

Other viral vectors which can be used include adeno-associated virus, vaccinia virus, bovine papilloma virus, or a herpesvirus such as Epstein-Barr virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Antisense based strategies can be employed to explore ARMP gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target ARMP mRNA. Hybridization is required for the antisense effect to occur, however the efficiency of intracellular hybridization is low and therefore the consequences of such an event may not be very successful. Antisense strategies may use a variety of approaches including the use of antisense oligonucleotides, injection of antisense RNA and transfection of antisense RNA expression vectors. Antisense effects can be induced by control (sense) sequences, however, the extent of phenotypic changes are highly variable. Phenotypic effects induced by antisense effects are based on changes in criteria such as protein levels, protein activity measurement, and target mRNA levels. Multidrug resistance is a useful model to study molecular events associated with phenotypic changes due to antisense effects, since the multidrug resistance phenotype can be established by expression of a single gene mdrl (MDR gene) encoding for P-glycoprotein.

Transplantation of normal genes into the affected area of the patient can also be useful therapy for Alzheimer's Disease. In this procedure, a normal hARMP protein is transferred into a cultivable cell type such as glial cells, either exogenously or endogenously to the patient. These cells are then injected serotologicially into the disease affected tissue(s). This is a known treatment for Parkinson's disease.

Immunotherapy is also possible for Alzheimer's Disease. Antibodies can be raised to a mutant ARMP protein (or portion thereof) and then administered to bind or block the mutant protein and its deleterious effects. Simultaneously, expression of the normal protein product could be encouraged. Administration could be in the form of a one time immunogenic preparation or vaccine immunization. An immunogenic composition may be prepared as injectables, as liquid solutions or emulsions. The ARMP protein may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcutaneously or intramuscularly.

The immunogenic preparations and vaccines are administered in such amount as will be therapeutically effective, protective and immunogenic. Dosage depends on the route of administration and will vary according to the size of the host.

Similar gene therapy techniques may be employed with respect to the E5-1 gene.

The above disclosure generally describes the present invention. A more complete understanding can be obtained by reference to the following specific examples. These examples are described solely for purposes of illustration and are not intended to limit the scope of the invention. Changes in the form and substitution of equivalents are contemplated as circumstances may suggest or render expedient. Although specific terms have been employed herein, such terms are intended in a descriptive sense and not for purposes of limitations.

EXAMPLE 1

Development of the Genetic, Physical "Contig" and Transcriptional Map of the Minimal Co-Segregating Region The CEPH Mega YAC and the RPCI PAC human total genomic DNA libraries were searched for clones containing genomic DNA fragments from the AD3 region of chromosome 14q24.3 using oligonucleotide probes for each of the ## SSR marker loci used in the genetic linkage studies as well as ## additional markers depicted in FIG. 1a (Albertsen et al., 1990; Chumakov et al., 1992; Ioannu et al., 1994). The genetic map distances between each marker are depicted above the contig, and are derived from published data (NIH/CEPH Collaborative Mapping Group, 1992; Wang, 1992; Weissenbach, J. et al., 1992 Gyapay, G et al., 1994). Clones recovered for each of the initial marker loci were arranged into an ordered series of partially overlapping clones ("contig") using four independent methods. First, sequences representing the ends of the YAC insert were isolated by inverse PCR (Riley et al., 1990), and hybridized to Southern blot panels containing restriction digests of DNA from all of the YAC clones bearing overlapping sequences. Second, inter-Alu PCR was performed on each YAC, and the resultant band patterns were compared across the pool of recovered YAC clones in order to identify other clones bearing overlapping sequences (Bellamne-Chartelot et al., 1992; Chumakov et al; 1992). Third, to improve the specificity of the Alu-PCR fingerprinting, we restricted the YAC DNA with HaeIII or RsaI, amplified the restriction products with both Alu and L1H consensus primers, and resolved the products by polyacrylamide gel electrophoresis. Finally, as additional STSs were generated during the search for transcribed sequences, these STSs were also used to identify overlaps. The resultant contig was complete except for a single discontinuity between YAC932C7 bearing D14S53 and YAC746B4 containing D14S61. The physical map order of the STSs within the contig was largely in accordance with the genetic linkage map for this region (NIH/CEPH Collaborative Mapping Group, 1992; Wang, Z., Webber, J. L., 1992; Weissenbach, J. et al., 1992; Gyapay, G. et al., 1994). However, as with the genetic maps, we were unable to unambiguously resolve the relative order of the loci within the D14S43/D14S71 cluster and the D14S76/D14S273 cluster. PAC1 clones suggest that D14S277 is telomeric to D14S268, whereas genetic maps have suggested the reverse order. Furthermore, a few STS probes failed to detect hybridization patterns in at least one YAC clone which, on the basis of the most parsimonious consensus physical map and from the genetic map, would have been predicted to contain that STS. For instance, the D14S268 (AFM265) and RSCAT7 STSs are absent from YAC788H12. Because these results are reproducible, and occurred with several different STS markers, these results most likely reflect the presence of small interstitial deletions with one of the YAC clones.

EXAMPLE 2

Cumulative Two-Point Lod Scores for Chromosome 14q24.3 Markers

Genotypes of each polymorphic microsatellite marker locus were determined by PCR from 1000 ng of genomic DNA of all available affected and unaffected pedigree members as previously described (St. George-Hyslop, P et al, 1992) using primer sequences specific for each microsatellite locus (Weissenbach, J et al., 1992; Gyapay, G et al., 1994). The normal population frequency of each allele was determined using spouses and other neurologically normal subjects from the same ethnic groups, but did not differ significantly from those established for mixed Caucasian populations (Weissenbach, J. et al., 1992; Gyapay, G. et al., 1994). The maximum likelihood calculations assumed an age of onset correction, marker allele frequencies derived from published series of mixed Caucasian subjects, an estimated allele frequence for the AD3 mutation of 1:1000 as previously described (St. George-Hyslop, P. et al., 1992). The analyses were repeated using equal marker allele frequencies, and using phenotype information only from affected pedigree members as previously described to ensure that inaccuracies in the estimated parameters used in the maximum likelihood calculations did not misdirect the analyses (St. George-Hyslop, P. et al., 1992). These supplemental analyses did not significantly alter either the evidence supporting linkage, or the discovery of recombination events.

EXAMPLE 3

Haplotypes Between Flanking Markers Segregated with AD3 in FAD Pedigrees

Extended haplotypes between the centromeric and telomeric flanking markers on the parental copy of chromosome 14 segregating with AD3 in fourteen early onset FAD pedigrees (pedigrees NIH2, MGH1, Tor1.1, FAD4, FAD1, MEX1, and FAD2 show pedigree specific lod scores≧+3.00 with at least one marker between D14S258 and D14S53). Identical partial haplotypes (boxed) are observed in two regions of the disease bearing chromosome segregating in several pedigrees of similar ethnic origin. In region A, shared alleles are seen at D14S268 ("B": allele size=126 bp, allele frequence in normal Caucasians=0.04; "C": size=124 bp, frequency=0.38); D14S277 ("B": size=156 bp, frequency=0.19; "C": size—154 bp, frequency=0.33); and RSCAT6 ("D": size=111 bp, frequency 0.25; "E" size=109 bp, frequency=0.20; "F" size=107 bp, frequency=0.47). In region B, alleles of identical size are observed at D14S43 ("A": size=193 bp, frequency=0.01; "D": size 187 bp, frequency=0.12; "E" size=185 bp, frequency=0.26; "I" size=160 bp, frequency=0.38); D14S273 ("3": size=193 bp, frequency=0.38; "4" size=191 bp, frequency=0.16; "5": size=189 bp, frequency=0.34; "6": size=187 bp, frequency=0.02) and D14S76 ("1": size=bp, frequency=0.01; "5": size=bp, frequency=0.38; "6": size=bp, frequency=0.07, "9": size=bp, frequency=0.38). The ethnic origins of each pedigree are abbreviated as: Ashk=Askenazi Jewish; Ital=Southern Italian; Angl=Anglo-Saxon-Celt; FrCan=French Canadian; Jpn=Japanese; Mex=Mexican Caucasian; Ger=German; Am=American Caucasian. The type of mutation detected is depicted by the amino acid substitution and putative condon number or by ND where no mutation has been detected because a comprehensive survey has not been undertaken due to the absence of a source of mRNA for RT-PCR studies.

EXAMPLE 4

Recovery of Transcribed Sequences from the AD3 Interval

Putative transcribed sequences encoded in the AD3 interval were recovered using either a direct hybridization method in which short cDNA fragments generated from human brain mRNA were hypridized to immobilized cloned genomic DNA fragments (Rommens, J M et al., 1993). The resultant short putatively transcribed sequences were used as probes to recover longer transcripts from human brain cDNA libraries (Stratagene, La Jolla). The physical locations of the original short clone and of the subsequently acquired longer cDNA clones were established by analysis of the hybridization pattern generated by hybridizing the probe to Southern blots containing a panel of EcoRI digested total DNA samples isolated from individual YAC clones within the contig. The nucleotide sequence of each of the longer cDNA clones was determined by automated cycle sequencing (Applied Biosystems Inc., Calif.), and compared to other sequences in nucleotide and protein databases using the blast algorithm (Atschul, S F et al., 1990). Accession numbers for the transcribed sequences in this report are L40391, L40392, L40393, L40394, L40395, L40396, L40397, L40398, L40399, L40400, L40401, L40402, and L40403.

EXAMPLE 5

Locating Mutations in the ARMP Gene Using Restriction Enzymes

The presence of Ala 246 Glu mutation which creates a DdeI restriction site was assayed in genomic DNA by PCR using the end labelled primer 849 (5'-atctccggcaggcatatct-3') SEQ ID NO:129 and the unlabelled primer 892 (5'-tgaaatcacagccaagatgag-3') SEQ ID NO:130 to amplify an 84 bp genomic exon fragment using 100 ng of genomic DNA template, 2 mM $MgCl_2$, 10 pMoles of each primer, 0.5 U Taq polymerase, 250 uM dNTPs for 30 cycles of 95° C.×20 seconds, 60° C.×20 seconds, 72° C.×5 seconds. The products were incubated with an excess of DdeI for 2 hours according to the manufacturers protocol, and the resulting restriction fragments were resolved on a 6% nondenaturing polyacrylamide gel and visualized by autoradiography. The presence of the mutation was inferred from the cleavage of the 84 bp fragment due to the presence of a DdeI restriction site. All affected members of the FAD1 pedigree (filled symbols) and several at-risk members ("R") carried the DdeI site. None of the obligate escapees (those individuals who do not get the disease, age>70 years), and none of the normal controls carried the DdeI mutation.

EXAMPLE 6

Location Mutation in the ARMP Gene Using Allele Specific Oligonucleotides

The presence of the Cys 410 Tyr mutation was assayed using allele specific oligonucleotides. 100 ng of genomic DNA was amplified with the exonic sequence primer 885 (5'-tggagactggaacacaac-3') SEQ ID NO:127 and the opposing intronic sequence primer 893 (5'-gtgtggccagggtagagaact-3') SEQ ID NO:128 using the above reaction conditions except 2.5 mM $MgCl_2$, and cycle conditions of 94° C.×20 seconds, 58° C.×20 seconds, and 72° C. for 10 seconds). The resultant 216 bp genomic fragment was denatured by 10-fold dilution in 0.4M NaOH, 25 mM EDTA, and was vacuum slot-blotted to duplicate nylon membranes. The end-labelled "wild-type" primer 890 (5'-ccatagcctgtttcgtagc-3') SEQ ID NO:131 and the end-labelled "mutant" primer 891 (5'-ccatagcctgtttcgtagc-3') SEQ ID NO:132 were hybridized to separate copies of the slot-blot filters in 5×SSC, 5×Denhardt's, 0.5% SDS for 1 hour at 48° C., and then washed successively in 2×SSC at 23° C. and 2×SSC, 0.1% SDS at 50° C. and then exposed to X-ray film. All testable affected members as well as some at-risk members of the AD3 (shown) and NIH2 pedigrees (not shown) possessed the Cys 410 Tyr mutation. Attempts to detect the Cys 410 Try mutation by SSCP revealed that a common intronic sequence polymorphism migrated with the same SSCP pattern.

EXAMPLE 7

Northern Hybridization Demonstrating the Expression of ARMP Protein mRNA in a Variety of Tissues Total cytoplasmic RNA was isolated from various tissue samples (including heart, brain, and different regions of placenta, lung, liver, skeletal muscle, kidney and pancreas) obtained from surgical pathology using standard procedures such as CsCl purification. The RNA was then electrophoresed on a formaldehyde gel to permit size fractionation. The nitrocellulose membrane was prepared and the RNA was then transferred onto the membrane. $^{32}$P-labelled cDNA probes were prepared and added to the membrane in order for hybridization between the probe the RNA to occur. After washing, the membrane was wrapped in plastic film and placed into imaging cassettes containing X-ray film. The autoradiographs were then allowed to develop for one to several days. The positions of the 28S and 18S rRNA bands are indicated. Sizing was established by comparison to standard RNA markers. Analysis of the autoradiographs revealed a prominent band at 3.0 kb in size. These northern blots demonstrated the ARMP gene is expressed in all of the tissues examined.

EXAMPLE 8

Eukaryotic and Prokaryotic Expression Vector Systems

Eukaryotic and prokaryotic expression systems have been generated using two different classes of ARMP nucleotide cDNA sequence inserts. In the first class, termed full-length constructs, the entire ARMP cDNA sequence was inserted into the expression plasmid in the correct orientation, and included both the natural 5' UTR and 3' UTR sequences as well as the entire open reading frame. The open reading frames bear a nucleotide sequence cassette which allows either the wild type open reading frame to be included in the expression system or alternatively, single or a combination of double mutations can be inserted into the open reading frame. This was accomplished by removing a restriction fragment from the wild type open reading frame using the enzymes NarI and PflmI and replacing it with a similar fragment generated by reverse transcriptase PCR and which bears the nucleotide sequence encoding either the Met146Leu mutation or the Hys163Arg mutation. A second restriction fragment was removed from the wild type normal nucleotide sequence for the open reading frame by cleavage with the enzymes PflmI and NcoI and replaced with restriction fragments bearing either the nucleotide sequence encoding the Ala246Glu mutation, or the Ala260Val mutation or the Ala285Val mutation or the Leu286Val mutation, or the Leu392Val mutation, or the Cys410 Tyr mutation. Finally, a third variant bearing combinations of either the Met146Leu or His163Arg mutations in tandem with the remaining mutations by linking the NarI-PflmI fragment bearing these mutations and the PflmI-NcoI fragment bearing the remaining mutations.

A second variant of cDNA inserts bearing wild type or mutant cDNA sequences was constructed by removing from the full-length cDNA the 5' UTR and part of the 3' UTR sequences. The 5' UTR sequence was replaced with a synthetic oligonucleotide containing a KpnI restriction site and a Kozak initiation site (oligonucleotide 969: ggtaccgccaccatgacagaggtacctgcac) SEQ ID NO:139. The 3' UTR was replaced with an oligonucleotide corresponding to position 2566 of the cDNA and bears an artificial EcoRI site (oligonucleotide 970: gaattcactggctgtagaaaaagac) SEQ ID NO:140. Mutant variants of this construct were then made by inserting the same mutant sequences described above at the NarI-PflmI fragment, and at the PsImI-NcoI sites described above.

For eukaryotic expressions, these various cDNA constructs bearing wild type and mutant sequences were cloned into the expression vector pZeoSV (invitrogen). For prokaryotic expression, two constructs were made using the gluthathione S-transferase fusion vector pGEX-kg. The inserts which have been attached to the GST fusion nucleotide sequence are the same nucleotide sequence described above generated with the oligonucleotide primers 969, SEQ ID NO:139 and 970, SEQ ID NO:140, bearing either the normal open reading frame nucleotide sequence or bearing a combination of single and double mutations as described above. This construct allows expression of the full-length protein in mutant and wild type variants in prokaryotic cell systems as a GST fusion protein which will allow purification of the full-length protein followed by removal of the GST fusion product by thrombin digestion. The second prokaryotic cDNA construct was generated to create a fusion protein with the same vector, and allows the production of the amino acid sequence corresponding to the hydrophillic acid loop domains between TM6 and TM7 of the full-length protein, as either a wild type nucleotide sequence (thus a wild type amino acid sequence for fusion proteins) or as a mutant sequence bearing either the Ala285Val mutation, or the Leu286Val mutation, or the Leu392Val mutation. This was accomplished by recovering wild type or mutant sequence from appropriate sources of RNA using the oligonucleotide primers 989: ggatccggtccacttcgtatgctg SEQ ID NO:141, and 990: tttttgaattcttaggctatggttgtgttcca SEQ ID NO:142. This allows cloning of the appropriate mutant or wild type nucleotide sequence corresponding to the hydrophillic acid loop domain at the BamHI and the EcoRI sites within the pGEX-KG vector.

These prokaryotic expression systems allow the holo-protein or various important functional domains of the protein to be recovered as fusion proteins and then used for binding studies, structural studies, functional studies, and for the generation of appropriate antibodies.

EXAMPLE 9

Identification of Three New Mutations in the ARMP Gene

Three novel mutations have been identified in subjects affected with early onset Alzheimer's Disease. All of these mutations co-segregate with the disease, and are absent from at least 200 normal chromosomes. The three mutations are as follows: a substitution of C by T at position 1027 which results in the substitution of alanine 260 for valine; substitution of C by T at position 1102, which results in the substitution of alanine at 285 by valine; and substitution of C by G at position 1422 which results in the substitution of leucine 392 by valine. Significantly, all of these mutations occur within the acidic hydrophillic loop between putative TM6 and TM7. Two of the mutations (A260V; A285V) and the L286V mutation are also located in the alternative spliced domain.

The three new mutations, like the other mutations, can be assayed by a variety of strategies (direct nucleotide sequencing, Allele specific oligos, ligation polymerase chain reaction, SSCP, RFLPs) using RT-PCR products representing the mature mRNA/cDNA sequence or genomic DNA. We have chosen allele specific oligos. For the A260V and the A285V mutations, genomic DNA carrying the exon can be amplified using the same PCR primers and methods for the L286V mutation. PCR products were then denatured and slot blotted to duplicate nylon membranes using the slot blot protocol described for the C410T mutation.

The Ala260Val mutation was scored by these blots by using hybridization with end-labeled allele-specific oligonucleotides corresponding to the wild type sequence (994: gattagtggttgttttgtg) SEQ ID NO:143 or the mutant sequence (995: gattagtggctgttttgtg) SEQ ID NO:144 by hybridization at 48° C. followed by a wash at 52° in 3×SSC buffer containing 0.1% SDS. The Ala285Val mutation was scored on these slot blots as described above but using instead the allele-specific oligonucleotides for the wild type sequence (1003: tttttccagctctcattta)-SEQ ID NO:145 or the mutant primer (1004: tttttccagttctcattta) SEQ ID NO:146 at 48° C. followed by washing at 52° C. as above except that the wash solution was 2×SSC.

The Leu392Val mutation was scored by amplification of the exon from genomic DNA using primers 996 (aaacttggat-tgggagat) SEQ ID NO:167 and 893 (gtgtggccagggtagagaact) SEQ ID NO:128 using standard PCR buffer conditions excepting that the magnesium concentration was 2 mM and cycle conditions were 94° C. time 10 seconds, 56° C. times 20 seconds, and 72° C. for 10 seconds. The result 200 based pair genomic fragment was denatured as described for the Cys410Tyr mutation and slot-blotted in duplicate to nylon membranes. The presence or absence of the mutation was then scored by differential hybridization to either a wild type end-labelled oligonucleotide (999: tacagtgttctggttggta) SEQ ID NO:148 or with an end-labeled mutant primer (100: tacagtgttgtggttggta) SEQ ID NO:149 by hybridization at 45° C. and then successive washing in 2×SSC at 23° and then at 68° C.

EXAMPLE 10

Polyclonal Antibody Production

Peptide antigens were synthesized by solid-phase techniques and purified by reverse phase high pressure liquid chromatography. Peptides were covalently linked to keyhole limpet hematoxylin (KLH) via disulfide linkages that were made possible by the addition of a cystein residue at the peptide C-terminus. This additional residue does not appear normally in the protein sequence and was included only to facilitate linkage to the KLH molecule. A total of three rabbits were immunized with peptide-KLH complexes for each peptide antigen and were then subsequently give booster injections at seven day intervals. Antisera were collected for each peptide and pooled and IgG precipitated with ammonium sulfate. Antibodies were then affinity purified with Sulfo-link agarose (Pierce) coupled with the appropriate peptide. This final purification is required to remove non-specific interactions of other antibodies present in either the pre- or post-immune serum.

The specific sequences to which we have raised antibodies are:

```
Polyclonal antibody 1:
NDNRERQEHNDRRSL (C)-residues 30-44    SEQ ID NO: 169

Polyclonal antibody 2:
KDGQLIYTPFTEDTE (C)-residues 109-123 SEQ ID NO: 170

Polyclonal antibody 3:
EAQRRVSKNSKYNAE (C)-residues 304-318 SEQ ID NO: 171
```

The non-native cysteine residue is indicated at the C-terminal by (C). These sequences are contained within various predicted domains of the protein. For example, antibodies 1,3, and 4 are located in potentially functional domains that are exposed to the aqueous media and may be involved in binding to other proteins critical for the development of the disease phenotype. Antibody 2 corresponds to a short linking region situated between the predicted first and second transmembrane helices.

EXAMPLE 11

Identification of Two Mutations in E5-1 Gene

RT-PCR products corresponding to the E5-1ORF were generated from RNA of lymphoblasts or frozen post-mortem brain tissue using oligonucleotide primer pairs 1021:5'-cagaggatggagagaatac SEQ ID NO:172 and 1018:5'-ggctc-cccaaaactgtcat SEQ ID NO:173 (product=888 bp); and 1071: 5'-gccctagtgttcatcaagta SEQ ID NO:174 and 1022:5'-aaagcgggagccaaagtc SEQ ID NO:175 (product=826 bp) by PCR using 250 μMol dNTPs, 2.5 mM MgC12, 10 pMol oligunucleotides in 10 μl cycled for 40 cycles of 94° C.×20 seconds, 58° C.×20 seconds, 72° C.×45 seconds. The PCR products were sequenced by automated cycle sequencing (ABI, Foster City, A) and the fluorescent chromatograms were scanned for heterozygous nucleotide substitutions by direct inspection and by the Factura (ver 1.2.0) and Sequence Navigator (ver 1.0.1b15) software packages (data not shown).

Asn141Ile: the A→T substitution at nucleotide 787 creates a BclI restriction site. The exon bearing this mutation was amplified from 100 ng of genomic DNA using 10 pMol of oligonucleotides 1041: 5'-cattcactaggacacacc SEQ ID NO:163 (end-labelled) and 1042: 5'-tgtagagcaccaccaaga SEQ ID NO:164 (unlabelled), and PCR reaction conditions similar to those described below for the Met239Val. 2 μl of the PCR product was restricted to BclI (NEBL, Beverly, Mass.) in 10 μl reaction volume according to the manufacturers' protocol, and the products were resolved by non-denaturing polyacrylamide gel electrophoresis. In subjects with wild type sequences, the 114 bp PCR product is cleaved into 68 bp and 46 bp fragments. Mutant sequences cause the product to be cleaved into 53 bp, 46 bp and 15 bp.

Met239Val: The A→G substitution at nucleotide 1080 deletes a NlaIII restriction site, allowing the presence of the Met239Val mutation to be detected by amplification from 100 ng of genomic DNA using PCR (10 pMol oligonucleotides 1034:5'-gcatggtgtgcatccact SEQ ID NO:165, 1035:5'-ggac-cactctgggaggta SEQ ID NO:166; 0.5 U Taq polymerase, 250 μM dNTPS, 1 μCi alpha $^{32}$P-dCTP, 1.5 mM MgCl$_2$, 10 μl volume; 30 cycles of 94° C.×30 seconds, 58° C.×20 seconds, 72° C.×20 seconds) to generate a 110 bp product. 2 μl of the PCR reaction were diluted to 10 μl and restricted with 3 U of NlaIII (NEBL, Beverly Mass.) for 3 hours. The restriction products were resolved by non-denaturing polyacrylamide gel electrophoresis and visualized by autoradiography. Normal subjects show cleavage products of 55, 35, 15 and 6 bp, whereas the mutant sequence gives fragments of 55, 50 and 6 bp.

Although preferred embodiments of the invention have been described herein in detail, it will be understood by those skilled in the art that variations may be made thereto without departing from the spirit of the invention or the scope of the appended claims.

TABLE 1

| | RECOMBINATION FRACTION (θ) | | | | | | |
|---|---|---|---|---|---|---|---|
| LOCUS | 0.00 | 0.05 | 0.10 | 0.15 | 0.20 | 0.30 | 0.40 |
| D 14S63 | -∞ | 1.54 | 3.90 | 4.38 | 4.13 | 2.71 | 1.08 |
| D14S258 | -∞ | 21.60 | 19.64 | 17.19 | 14.50 | 8.97 | 3.81 |
| D 14S77 | -∞ | 15.18 | 15.53 | 14.35 | 12.50 | 7.82 | 2.92 |
| D 14S71 | -∞ | 15.63 | 14.14 | 12.19 | 10.10 | 5.98 | 2.39 |
| D 14S43 | -∞ | 19.36 | 17.51 | 15.27 | 12.84 | 7.80 | 3.11 |
| D14S273 | -∞ | 12.30 | 11.52 | 10.12 | 8.48 | 5.04 | 1.91 |
| D14S61 | -∞ | 26.90 | 24.92 | 22.14 | 18.98 | 12.05 | 5.07 |
| D 14S53 | -∞ | 11.52 | 11.41 | 10.39 | 8.99 | 5.73 | 2.51 |
| D 14S48 | -∞ | 0.50 | 1.05 | 1.14 | 1.04 | 0.60 | 0.18 |

TABLE 2

| | PEDIGREE ID | | | | | | | | | | | | | |
|---|---|---|---|---|---|---|---|---|---|---|---|---|---|---|
| LOCUS | N1B2 | FaD3 | TUR1.1 | FaD4 | RB | FaD1 | BIG12 | BOW | COOK | 603 | Tor42 | QUE | MEX1 | FAD2 |
| D14S83 | 1 | 4 | 7 | 4 | | 5 | | 6 | 6 | | 7 | | 9 | -2 |
| D14S258 | 6 | 6 | 8 | 7 | 4 | 5 | 5 | 6 | 6 | | 7 | 6 | 7 | 6 |
| D14S268 | C | C | B | B | C | C | C | C | C | C | C | B | C | C |
| D14S277 | C | C | C | C | C | C | C | C | C | A | A | C | B | C |
| D14S786 | D | D | E | E | F | E | E | D/F | E | E | E | E | F | D |
| D14S77 | Y | Y | K | S | | P | P | X | H | | C | | U | A |
| D14S78 | 7 | 7 | 1 | 5 | 7 | 7 | | 6 | 7 | | 3 | 7 | 2 | 6 |
| D14S43 | A | A | I | I | I | E | D | 1 | 1 | | C | 1 | D | C |
| D14S273 | 6 | 6 | 3 | 5 | 5 | 4 | 4 | 4 | 6 | | 6 | 6 | 5 | 3 |
| D14S76 | 5 | 5 | 5 | 5 | 5 | 6 | 9 | 9 | | | 9 | 1 | 5 | 5 |
| D14S61 | E | E | G | F | | I | | | | | D | | L | F |
| D14S53 | F | F | C | F | F | J | C | F | E | | J | | D | F |
| ETHNIC ORIGIN | Ashk | Ashk | Ital | Ital | Ital | Angl | Angl | Angl | Angl | Amer | FrCan | FrCan | Mex | Ger |
| MUTATION | C410Y | C410Y | M146L | M146L | ND | A246E | ND | ND | ND | H163R | H163R | ND | ND | L286V |

TABLE 3

```
                                                          Similarities
       No.   Target File         Key   Target  Overlap  Match  Percentages
        1    marmp.con/long [Frame 1]   1      1        467    465    99.57%
             1         10        20        30        40        50        60        70
Human  N-    MTELPAPLSYFQNAQMSEDNHLSNTVRSQNDNRERQEHNDRRSLGHPEPLSNGRPQGNSRQVVEQDEEED    SEQ ID NO: 2
             **************************************************************
Mouse  N-    MTEIPAPLSYFQNAQMSEDSHSSSAIRSQNDSQERQQQHDRQRLDNPEPISNGRPQSNSRQVVEQDEEED    SEQ ID NO: 4
             1         10        20        30        40        50        60        70

71        80        90        100       110       120       130       140
             EELTLKYGAKHVIMLFVPVTLCMVVVVATIKSVSFYTRKDGQLIYTPFTEDTETVGQRALHSILNAAIMI
             **************************************************************
             EELTLKYGAKHVIMLFVPVTLCMVVVVATIKSVSFYTRKDGQLIYTPFTEDTETVGQRALHSILNAAIMI
             71        80        90        100       110       120       130       140

141       150       160       170       180       190       200       210
             SVIVVMTILLVVLYKYRCYKVIHAWLIISSLLLLFFFSFIYLGEVFKTYNVAVDYITVALLIWNLGVVGM
             **************************************************************
             SVIVIMTILLVVLYKYRCYKVIHAWLIISSLLLLFFFSFIYLGEVFKTYNVXVDYVTVALLIWNWGVVGM
             141       150       160       170       180       190       200       210

211       220       230       240       250       260       270       280
             ISIHWKGPLRLQQAYLIMISALMALVFIKYLPEWTAWLILAVISVYDLVAVLCPKGPLRMLVETAQERNE
             **************************************************************
             IAIHWKGPLRLQQAYLIMISALMALVFIKYLPEWTAWLILAVISVYDLVAVLCPKGPLRMLVETAQERNE
             211       220       230       240       250       260       270       280

281       290       300       310       320       330       340       350
             TLFPALIYSSTMVWLVNMAEGDPEAQRRVSKNSKYNAESTERESQDTVAENDDGGFSEEWEAQRDSHLGP
             **************************************************************
             TLFPALIYSSTMVWLVNMAEGDPEAQRRVPKNPKYNTQRAERETQDSGSGNDDGGFSEEWEAQRDSHLGP
             281       290       300       310       320       330       340       350

351       360       370       380       390       400       410       420
             HRSTPESRAAVQELSSSILAGEDPEERGVKLGLGDFIFYSVLVGKASATASGDWNTTIACFVAILIGLCL
             **************************************************************
```

TABLE 3-continued

```
HRSTPESRAAVQELSGSILTSEDPEERGVKLGLGDFIFYSVLVGKASATASGDWNTTIACXVAILIGLCL
351        360       370       380       390       400       410       420

421       430       440       450       460
   TLLLLAIFKKALPALPISITFGLVFYFATDYLVQPFMDQLAFHQFYI                        -C
   ***********************************************
   XLLLLAIYKKGXPAXPISITFGFVFXFATDYLVQPFMDQLAFHQFYI                        -C
421       430       440       450       460
```

TABLE 4

HUMAN ARMP FUNCTION DOMAINS

| Domains (Amino Acid Residue) | | | Functional Characteristic |
|---|---|---|---|
| 82-100 | AA | | Hydrophobic |
| 132-154 | AA | | Hydrophobic |
| 164-183 | AA | | Hydrophobic |
| 195-213 | AA | | Hydrophobic |
| 221-238 | AA | | Hydrophobic |
| 244-256 | AA | | Hydrophobic |
| 281-299 | AA | | Hydrophobic |
| 404-428 | AA | | Hydrophobic |
| 431-449 | AA | | Hydrophobic |
| 115-119 | AA | (YTPF) SEQ ID NO: 161 | Phosphorylation Site |
| 353-356 | AA | (STPC) SEQ ID NO: 162 | Phosphorylation Site |
| 300-385 | AA | | Acid Rich Domain Possible Metal Binding Domain |

ANTIGENIC SITES INCLUDING AMINO ACID RESIDUES 27-44
46-48

TABLE 4-continued

HUMAN ARMP FUNCTION DOMAINS

| Domains (Amino Acid Residue) | Functional Characteristic |
|---|---|
| 50-60 | |
| 66-67 | |
| 107-111 | |
| 120-121 | |
| 125-126 | |
| 155-160 | |
| 185-189 | |
| 214-223 | |
| 220-230 | |
| 240-245 | |
| 267-269 | |
| 273-282 | |
| 300-370 | |
| 400-420 | |

TABLE 5

| MUTATION | ENZYME (effect of mutation) | AMPLIFICATION 0440 #1 | AMPLIFICATION 0440 #2 | ALLELE-SPECIFIC 0440 |
|---|---|---|---|---|
| M 146LEU | Bsph1 (destroy) | 910 (170-S182F) TCACAGAAGATACCG AGACT (SEQ ID NO: 176) | 911 (170-S182)R CCCAACCATAAGAAG AACAG (SEQ ID NO: 177) | |
| MIS 164 Ary | Nla III (destroy) | 927 (intronic) TCTGTACTTTTTAAG GGTTGTG (SEQ ID NO: 178) | 928 ACTTCAGAGTAATTC ATCANCA (SEQ ID NO: 179) | |
| Ala 246 | Dlc I (create) | 849* GACTCCAGCAGGCAT ATCT (SEQ ID NO: 80) | 892 TGAAATCACAGCCAA GATGAG (SEQ ID NO: 130) | |
| Leu 286 Val | Pvu II (create) | 952 GATGAGACAAGTNCC NTGAA (SEQ ID NO: 181) 945 TTAGTGGCTGTTTNG TGTCC (SEQ ID NO: 182) | 951 CACCCATTTACAAGT TTAGC (SEQ ID NO: 183) | |
| Cys 410 Tys | Allele specific ligo | 823 GTGTGGCCAGGGTAG AGAACT (SEQ ID NO: 128) | 885 TGGAGACTGGAACAC AAC (SEQ ID NO: 127) | CCATAGCCTGTTTCGTAGC (SEQ ID NO: 131) 890 = WT CCATAGCCTATTTCGTAGC (SEQ ID NO: 132) 891 = MUT |

TABLE 6

POSITION OF EXONS AND INTRON-EXON BOUNDARIES OF THE ARMP GENE

| cDNA/mRNA SEQUENCE | | CORRESPONDING GENOMIC SEQUENCE | |
|---|---|---|---|
| ARMP (917 ver) | Transcript ID CC44 ver | Genomic sequence file ID & position of exon | Comments |
| 1-113 bp | N/A | 917-936.gen @ 731-834 bp | Alternate 5'UTR |
| N/A | 1-422 bp | 917-936.gen @ 1067-1475 bp | Alternate 5'UTR |
| 114-195 bp | 423-500 bp | 932-943.gen @ 589-671 bp | |
| 196-335 bp | 501-632 bp | 932-943.gen @ 759-899 bp | 12 bp Variably spliced |
| 337-586 bp | 633-883 bp | 901-912.gen @ 787-1037 bp | |
| 587-730 bp | 884-1026 bp | 910-915.gen @ 1134-1278 bp | M146L mutation |
| 731-795 bp | 1027-1092 bp | 925-913.gen @ 413-578 bp | H163R mutation |
| 796-1017 bp | 1093-1314 bp | 849-892.gen @ 336-558 bp | A246E mutation |
| 1018-1116 bp | 1315-1413 bp | 951-952.gen @ 312-412 bp | L286V mutation, variable spl |
| 1117-1204 bp | 1414-1501 bp | 983-1011.gen @ 61-149 bp | |
| 1205-1377 bp | 1502-1674 bp | 874-984.gen @ 452-625 bp | |
| 1378-1497 bp | 1674-1794 bp | 885-1012.gen @ 431-550 bp | C410Y mutation |
| 1493-2760 bp | 1795-3060 bp | 930-919.gen @ −10 bp-cnd | last AA, STOP, 3'UTR |

TABLE 7

MUTATIONS AND POLYMORPHISMS IN THE ARMP GENE

| Nucleotide # in ARMP.UPD | Amino acid # in ARMP.PRO | Comment |
|---|---|---|
| A->$C_{684}$ | Met146Leu | Pathogenic, Unique to AD affected. |
| A->$G_{736}$ | His163Arg | |
| C->$A_{985}$ | Ala246Glu | Pathogenic, Unique to AD affected. |
| C->$T_{1027}$ | Ala260Val | Pathogenic, Unique to AD affected. |
| C->$T_{1102}$ | Ala285Val | Pathogenic, Unique to AD affected. |
| C->$G_{1104}$ | Leu286Val | Pathogenic, Unique to AD affected. |
| C->$G_{1422}$ | Leu392Val | Pathogenic, Unique to AD affected. |
| G->$A_{1477}$ | Cys410Tyr | Pathogenic, Unique to AD affected. |
| G->$T_{863}$ | Phe205Leu | Polymorphism in normals |
| C->$A_{1700}$ | non-coding | 3'UTR polymorphism |
| G->$A_{2601}$ | non-coding | " |
| del$C_{2620}$ | non-coding | " |

TABLE 8

```
E5-1    1   MLTFMASDSEEEVCDERTSLMSAESPTPRSC*QEGRQGPEDGE**NTAQWRSQENEED   55
             |    |   |    |  |    | |      ||    |    |||    |
S182    1   ******************MT*ELPAPLSYFQNA*QMSEDNHLSNTV**RSQ*N**D   31

E5-1   56   G*E**EDPDRYVCS*GVP*****GRPPGL*****E******EELTLKYGAKHVIMLF   92
             |   ||    ||     |||   |||||     |  |   |||||||||||||||||
S182   51   NRERQEHNDRR**SLGHPEPLSNGRPQGNSRQVVEQDEEEDEELTLKYGAKHVIMLF   86

I
                                                             ↓
E5-1   93   VPVTLCMIVVVATIKSVRFYTEKNGQLIYTPFTEDTPSVGQRLLNSVLNTLIMISVI  149
            |||||||  |||||||| |||| | ||||||||||||| |||| ||| || ||||||
S182   87   VPVTLCMVVVVATIKSVSFYTRKDGQLIYTPFTEDTETVGQRALHSILNAAIMISVI  143

E5-1  150   VVMTIFLVVVLYKYRCYKFIHGWLIMSSLMLLFLFTYIYLGEVLKTYNVAMDYPTL*L  205
            |||||  |||||||||||| | ||| ||| ||  | |||||||| |||||| | |
S182  144   VVMTILLVVLYKYRCYKVIHAWLIISSLLLLFFFSFIYLGEVFKTYNVAVDYITVAL  200
                 ↑                ↑
                 L                R

V
                                         ↓
E5-1  206   LTVWNFGAVGMVCIHWKGPLVLQQAYLIMISALMALVFIKYLPEWSAWVILGA*ISV  261
              |||| |||  ||||||||| ||||||||||||||||||||||||   ||  |||
S182  201   LI*WNFGVVGMISIHWKGPLRLQQAYLIMISALMALVFIKYLPEWTAWLIL*AVISV  255
                                                         ↑
                                                         E
```

TABLE 8-continued

```
                 ********************************
E5-1   262  YDLVAVLCPKGPLRMLVETAQERNEPIFPALIYSSAMVWTVGMAKLDP******S**    310
            |||||||||||||||||||||||||| |||||||| ||| || || |      |
S182   256  YDLVAVLCPKGPLRMLVETAQERNETLFPALIYSSTMVWLVNMAEGDPEAQRRVSKN    312
                 *****************************↑↑****
                                              VV

E5-1   311  SQGAL*****QLPY*DP****EME*EDSYDSF*GEPSYPE**VFEPPLT    345
            |    |       |  |   ||   |||  ||  |  |    ||      |  |
S182   301  SKYNAESTERESQDTVAENDDGGFSE*EWEAQRDSHLG*PHRSTPESRAAVQE**LS    365

E5-1   346  GYP**GEELEEEEERGVKLGLGDFIFYSVLVGKAAATGSGDWNTTLACFVAILIGLC    400
            ||   ||   |||||||||||||||||||||| || |||||| ||||||||||||
S182   366  SSILAGEDP***EERGVKLGLGDFIFYSVLVGKASATASGDWNTTIACFVAILIGLC    420
                                              ↑            ↑
                                              V            Y

E5-1   401  LTLLLLAVFKKALPALPISITFGLIFYFSTDNLVRPFMDTLASHQLYI*           448
            ||||||| ||||||||||||||| | || |||| ||| || ||| |||
S182   421  LTLLLLAIFKKALPALPISITFGLVFYFATDYLVQPFMDQLAFHQFYI*           467
```

---

We claim:

1. An isolated antibody that specifically binds to a mutant mammalian Presenilin-2 protein having the amino acid sequence depicted in SEQ ID NO:138, wherein the methionine at position 239 is mutated to a valine, and wherein said antibody specifically binds to an epitope comprising said mutation in said protein.

2. The antibody according to claim 1, wherein the antibody is a monoclonal antibody.

3. A hybridoma that produces an antibody according to claim 2.

4. A method for detecting the presence of a mutant mammalian Presenilin-2 protein in a biological sample, the method comprising:

(i) contacting the biological sample with the antibody as defined in any one of claims 1-2, (ii) incubating the sample and the antibody under conditions to induce binding of the antibody to the sample to form a complex, and (iii) detecting the complex.

5. A method for assessing an increased risk of Alzheimer's Disease in a subject, comprising:

(i) determining the level of a mutant mammalian Presenilin-2 protein in a biological sample from a subject by:

(a) contacting the biological sample with the antibody as defined in any one of claims 1-2, (b) incubating the sample and the antibody under conditions to induce binding of the antibody to the sample to form a complex,
(c) detecting the complex; and
(ii) comparing the level of mutant mammalian Presenilin-2 protein in the biological sample from the subject to a normal level of mutant mammalian Presenilin-2 protein, the normal level determined from an average of the level mutant mammalian Presenilin-2 protein in a biological sample from a population consisting of subjects who do not show any symptoms of Alzheimer's Disease, wherein a higher level in the biological sample from the subject indicates an increased risk of Alzheimer's Disease.

* * * * *

SEQUENCE LISTING

```
<160> NUMBER OF SEQ ID NOS: 185

<210> SEQ ID NO 1
<211> LENGTH: 2791
<212> TYPE: DNA
<213> ORGANISM: Homo sapiens
<220> FEATURE:
<221> NAME/KEY: misc_feature
<222> LOCATION: (1)..(2791)
<223> OTHER INFORMATION: where n may be either a or g or c or t/u,
      unknown or other

<400> SEQUENCE: 1
tgggacaggc agctccgggg tccgcggttt cacatcggaa acaaaacagc ggctggtctg      60
gaaggaacct gagctacgag ccgcggcggc agcggggcgg cggggnaagc gtatacctaa     120
tctgggagcc tgcaagtgac aacagccttt gcggtcctta gacagcttgg cctggaggag     180
aacacatgaa agaagaacc  tcaagaggct ttgttttctg tgaaacagta tttctataca     240
gttgctccaa tgacagagtt acctgcaccg ttgtcctact tccagaatgc acagatgtct     300
gaggacaacc acctgagcaa tactgtacgt agccagaatg acaatagaga acggcaggag     360
cacaacgaca gacggagcct tggccaccct gagccattat ctaatggacg accccagggt     420
aactcccggc aggtggtgga gcaagatgag gaagaagatg aggagctgac attgaaatat     480
ggcgccaagc atgtgatcat gctctttgtc cctgtgactc tctgcatggt ggtggtcgtg     540
gctaccatta agtcagtcag cttttatacc cggaaggatg ggcagctaat ctataccccc     600
ttcacagaag ataccgagac tgtgggccag agagccctgc actcaattct gaatgctgcc     660
atcatgatca gtgtcattgt tgtcatgact atcctcctgg tggttctgta taaatacagg     720
tgctataagg tcatccatgc ctggcttatt atatcatctc tattgttgct gttctttttt     780
tcattcattt acttgggga  agtgtttaaa acctataacg ttgctgtgga ctacattact     840
gttgcactcc tgatctggaa tttgggtgtg gtgggaatga tttccattca ctggaaaggt     900
ccacttcgac tccagcaggc atatctcatt atgattagtg ccctcatggc cctggtgttt     960
atcaagtacc tccctgaatg gactgcgtgg ctcatcttgg ctgtgattc  agtatatgat    1020
```

| | | |
|---|---|---|
| ttagtggctg tttgtgtcc gaaaggtcca cttcgtatgc tggttgaaac agctcaggag | | 1080 |
| agaaatgaaa cgcttttcc agctctcatt tactcctcaa caatggtgtg gttggtgaat | | 1140 |
| atggcagaag gagacccgga agctcaaagg agagtatcca aaaattccaa gtataatgca | | 1200 |
| gaaagcacag aaagggagtc acaagacact gttgcagaga tgatgatgg cgggttcagt | | 1260 |
| gaggaatggg aagcccagag ggacagtcat ctagggcctc atcgctctac acctgagtca | | 1320 |
| cgagctgctg tccaggaact ttccagcagt atcctcgctg gtgaagaccc agaggaaagg | | 1380 |
| ggagtaaaac ttggattggg agatttcatt ttctacagtg ttctggttgg taaagcctca | | 1440 |
| gcaacagcca gtggagactg aacacaacc atagcctgtt cgtagccat attaattggt | | 1500 |
| ttgtgcctta cattattact ccttgccatt tcaagaaag cattgccagc tcttccaatc | | 1560 |
| tccatcacct ttgggcttgt tttctacttt gccacagatt atcttgtaca gcctttatg | | 1620 |
| gaccaattag cattccatca atttatatc tagcatattt gcggttagaa tcccatggat | | 1680 |
| gtttcttctt tgactataac caaatctggg gaggacaaaa gtgattttcc tgtgtccaca | | 1740 |
| tctaacaaag tcaagattcc cggctggact tttgcagctt ccttccaagt cttcctgacc | | 1800 |
| accttgcact attggacttt ggaaggaggt gcctatagaa aacgattttg aacatacttc | | 1860 |
| atcgcagtgg actgtgtcct cggtgcagaa actaccagat ttgagggacg aggtcaagga | | 1920 |
| gatatgatag gcccggaagt tgctgtgccc catcagcagc ttgacgcgtg gtcacaggac | | 1980 |
| gatttcactg acactgcgaa ctctcaggac taccggttac caagaggtta ggtgaagtgg | | 2040 |
| tttaaaccaa acggaactct tcatcttaaa ctacacgttg aaaatcaacc caataattct | | 2100 |
| gtattaactg aattctgaac ttttcaggag gtactgtgag gaagagcagg caccagcagc | | 2160 |
| agaatgggga atggagaggt gggcaggggt tccagcttcc ctttgatttt ttgctgcaga | | 2220 |
| ctcatccttt ttaaatgaga cttgttttcc cctctctttg agtcaagtca aatatgtaga | | 2280 |
| tgcctttggc aattcttctt ctcaagcact gacactcatt accgtctgtg attgccattt | | 2340 |
| cttcccaagg ccagtctgaa cctgaggttg ctttatccta aaagttttaa cctcaggttc | | 2400 |
| caaattcagt aaattttgga aacagtacag ctatttctca tcaattctct atcatgttga | | 2460 |
| agtcaaattt ggatttttcca ccaaattctg aatttgtaga catacttgta cgctcacttg | | 2520 |
| ccccagatgc ctcctctgtc ctcattcttc tctcccacac aagcagtctt tttctacagc | | 2580 |
| cagtaaggca gctctgtcgt ggtagcagat ggtcccactt attctagggt cttactcttt | | 2640 |
| gtatgatgaa aagaatgtgt tatgaatcgg tgctgtcagc cctgctgtca gaccttcttc | | 2700 |
| cacagcaaat gagatgtatg cccaaagcgg tagaattaaa gaagagtaaa atggctgttg | | 2760 |
| aagcaaaaaa aaaaaaaaaa aaaaaaaaa a | | 2791 |

```
<210> SEQ ID NO 2
<211> LENGTH: 467
<212> TYPE: PRT
<213> ORGANISM: Homo sapiens

<400> SEQUENCE: 2
```

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

```
Gln Asp Glu Glu Glu Asp Glu Leu Thr Leu Lys Tyr Gly Ala Lys
65                  70                  75                  80

His Val Ile Met Leu Phe Val Pro Val Thr Leu Cys Met Val Val
                85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
                115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Leu Gly Val Val
                195                 200                 205

Gly Met Ile Ser Ile His Trp Lys Gly Pro Leu Arg Leu Gln Gln Ala
                210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
                275                 280                 285

Ser Ser Thr Met Val Trp Leu Val Asn Met Ala Glu Gly Asp Pro Glu
                290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
                355                 360                 365

Leu Ala Gly Glu Asp Pro Glu Glu Arg Gly Val Lys Leu Gly Leu Gly
                370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
                420                 425                 430

Pro Ala Leu Pro Ile Ser Ile Thr Phe Gly Leu Val Phe Tyr Phe Ala
                435                 440                 445

Thr Asp Tyr Leu Val Gln Pro Phe Met Asp Gln Leu Ala Phe His Gln
450                 455                 460

Phe Tyr Ile
465
```

<210> SEQ ID NO 3
<211> LENGTH: 1929
<212> TYPE: DNA
<213> ORGANISM: Mus musculus
<220> FEATURE:
<221> NAME/KEY: misc_feature
<222> LOCATION: (1)..(1929)
<223> OTHER INFORMATION: where n may be either a or g or c or t/u, unknown or other

<400> SEQUENCE: 3

| | | | | | |
|---|---|---|---|---|---|
| accanacanc | ggcagctgag | gcggaaacct | aggctgcgag | ccggccgccc | gggcgcggag | 60 |
| agagaaggaa | ccaacacaag | acagcagccc | ttcgaggtct | ttaggcagct | ggaggagaa | 120 |
| cacatgagag | aaagaatccc | aagaggtttt | gttttctttg | agaaggtatt | tctgtccagc | 180 |
| tgctccaatg | acagagatac | ctgcaccttt | gtcctacttc | cagaatgccc | agatgtctga | 240 |
| ggacagccac | tccagcagcg | ccatccggag | ccagaatgac | agccaagaac | ggcagcagca | 300 |
| gcatgacagg | cagagacttg | acaaccctga | gccaatatct | aatgggcggc | cccagagtaa | 360 |
| ctcaagacag | gtggtggaac | aagatgagga | ggaagacgaa | gagctgacat | tgaaatatgg | 420 |
| agccaagcat | gtcatcatgc | tctttgtccc | cgtgaccctc | tgcatggtcg | tcgtcgtggc | 480 |
| caccatcaaa | tcagtcagct | tctatacccg | gaaggacggt | cagctaatct | acaccccatt | 540 |
| cacagaagac | actgagactg | taggccaaag | agccctgcac | tcgatcctga | atgcggccat | 600 |
| catgatcagt | gtcattgtca | ttatgaccat | cctcctggtg | gtcctgtata | aatacaggtg | 660 |
| ctacaaggtc | atccacgcct | ggcttattat | ttcatctctg | ttgttgctgt | tcttttttc | 720 |
| gttcatttac | ttaggggaag | tatttaagac | ctacaatgtc | kccgtggact | acgttacagt | 780 |
| agcactccta | atctggaatt | ggggtgtggt | cgggatgatt | gccatccact | ggaaaggccc | 840 |
| ccttcgactg | cagcaggcgt | atctcattat | gatcagtgcc | ctcatggccc | tggtatttat | 900 |
| caagtacctc | cccgaatgga | ccgcatggct | catcttggct | gtgatttcag | tatatgattt | 960 |
| ggtggctgtt | ttatgtccca | aaggcccact | tcgtatgctg | gttgaaacag | ctcaggaaag | 1020 |
| aaatgagact | ctctttccag | ctcttatcta | ttcctcaaca | atggtgtggt | tggtgaatat | 1080 |
| ggctgaagga | gacccagaag | cccaaaggag | ggtacccaag | aaccccaagt | ataacacaca | 1140 |
| aagagcggag | agagagacac | aggacagtgg | ttctgggaac | gatgatggtg | gcttcagtga | 1200 |
| ggagtgggag | gcccaaagag | acagtcacct | ggggcctcat | cgctccactc | ccgagtcaag | 1260 |
| agctgctgtc | caggaacttt | ctgggagcat | tctaacgagt | gaagaccgg | aggaaagagg | 1320 |
| agtaaaactt | ggactgggag | atttcatttt | ctacagtgtt | ctggttggta | aggcctcagc | 1380 |
| aaccgccagt | ggagactgga | acacaaccat | agcctgcttk | gtagccatac | tgatcggcct | 1440 |
| gtgccttana | ttactcctgc | tcgccattta | caagaaaggg | tngccagccc | ncccatctc | 1500 |
| catcaccttc | gggttcgtgt | tctncttcgc | cacggattac | cttgtgcagc | ccttcatgga | 1560 |
| ccaacttgca | ttccatcagt | tttatatcta | gcctttctgc | agttagaaca | tggatgtttc | 1620 |
| ttcttgatt | atcaaaaaca | caaaaacaga | gagcaagccc | gaggaggaga | ctggtgactt | 1680 |
| tcctgtgtcc | tcagctaaca | aaggcaggac | tccagctgga | cttctgcagc | ttccttccga | 1740 |
| gtctccctag | ccaccccgcac | tactggactg | tggaaggaag | cgtctacaga | ggaacggttt | 1800 |
| ccaacatcca | tcgctgcagc | agacggtgtc | cctcagtgac | ttgagagaca | aggacaagga | 1860 |
| aatgtgctgg | gccaaggagc | tgccgtgctc | tgctagcttt | ggmccgtggg | catggagatt | 1920 |
| tacccgcac | | | | | | 1929 |

```
<210> SEQ ID NO 4
<211> LENGTH: 467
<212> TYPE: PRT
<213> ORGANISM: Mus musculus
<220> FEATURE:
<221> NAME/KEY: MISC_FEATURE
<222> LOCATION: (1)..(467)
<223> OTHER INFORMATION: where X is unknown or other

<400> SEQUENCE: 4

Met Thr Glu Ile Pro Ala Pro Leu Ser Tyr Phe Gln Asn Ala Gln Met
1               5                   10                  15

Ser Glu Asp Ser His Ser Ser Ala Ile Arg Ser Gln Asn Asp Ser
            20                  25                  30

Gln Glu Arg Gln Gln His Asp Arg Gln Arg Leu Asp Asn Pro Glu
        35                  40                  45

Pro Ile Ser Asn Gly Arg Pro Gln Ser Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Xaa
            180                 185                 190

Val Asp Tyr Val Thr Val Ala Leu Leu Ile Trp Asn Trp Gly Val Val
        195                 200                 205

Gly Met Ile Ala Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Pro Lys Asn Pro Lys Tyr Asn Thr Gln Arg Ala
305                 310                 315                 320

Glu Arg Glu Thr Gln Asp Ser Gly Ser Gly Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Gly Ser Ile
```

-continued

```
                  355                 360                 365
Leu Thr Ser Glu Asp Pro Glu Glu Arg Gly Val Lys Leu Gly Leu Gly
            370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Xaa Val Ala Ile Leu Ile
                405                 410                 415

Gly Leu Cys Leu Xaa Leu Leu Leu Ala Ile Tyr Lys Lys Gly Xaa
            420                 425                 430

Pro Ala Xaa Pro Ile Ser Ile Thr Phe Gly Phe Val Phe Xaa Phe Ala
        435                 440                 445

Thr Asp Tyr Leu Val Gln Pro Phe Met Asp Gln Leu Ala Phe His Gln
450                 455                 460

Phe Tyr Ile
465

<210> SEQ ID NO 5
<211> LENGTH: 3087
<212> TYPE: DNA
<213> ORGANISM: Homo sapiens
<220> FEATURE:
<221> NAME/KEY: misc_feature
<222> LOCATION: (1)..(3087)
<223> OTHER INFORMATION: where n may be either a or g or c or t/u,
      unknown or other

<400> SEQUENCE: 5
gaattcggca cgagggaaat gctgtttgct cgaagacgtc tcagggcgca ggtgccttgg      60
gccgggatta gtagccgtct gaactggagt ggagtaggag aaagaggaag cgtcttgggc     120
tgggtctgct tgagcaactg gtgaaactcc gcgcctcacg ccccgggtgt gtccttgtcc     180
aggggcgacg agcattctgg gcgaagtccg cacscctctt gttcgaggcg aagacgggg      240 tctgatsctt tctccttggt cgggmctgtc tcgaggcatg catgtccagt gactcttgtg     300
tttgctgctg cttccctctc agattcttct caccgttgtg gtcagctctg ctttaggcan     360
tattaatcca tagtggaggc tgggatgggt gagagaattg aggtgacttt tccataattc     420
agacctaatc tgggagcctg caagtgacaa cagcctttgc ggtccttaga cagcttggcc     480
tggaggagaa cacatgaaag aaagaacctc aagaggcttt gttttctgtg aaacagtatt     540
tctatacagt tgctccaatg acagagttac ctgcaccgtt gtcctacttc agaatgcac      600 agatgtctga ggacaaccac ctgagcaata ctaatgacaa tagagaacgg caggagcaca     660
acgacagacg gagccttggc caccctgagc cattatctaa tggacgaccc cagggtaact     720
cccggcaggt ggtggagcaa gatgaggaag aagatgagga gctgacattg aaatatggcg     780
ccaagcatgt gatcatgctc tttgtccctg tgactctctg catggtggtg gtcgtggcta     840
ccattaagtc agtcagcttt tatacccgga aggatgggca gctaatctat acccccattca    900 cagaagatac cgagactgtg ggccagagag ccctgcactc aattctgaat gctgccatca     960
tgatcagtgt cattgttgtc atgactatcc tcctggtggt tctgtataaa tacaggtgct    1020
ataaggtcat ccatgcctgg cttattatat catctctatt gttgctgttc ttttttcat     1080 tcatttactt gggggaagtg tttaaaacct ataacgttgc tgtggactac attactgttg    1140
cactcctgat ctggaatttg gtgtggtgg gaatgatttc cattcactgg aaaggtccac    1200
ttcgactcca gcaggcatat ctcattatga ttagtgccct catggccctg gtgtttatca    1260
agtacctccc tgaatggact gcgtggctca tcttggctgt gatttcagta tatgatttag    1320
```

```
tggctgtttt gtgtccgaaa ggtccacttc gtatgctggt tgaaacagct caggagagaa   1380
atgaaacgct ttttccagct ctcatttact cctcaacaat ggtgtggttg gtgaatatgg   1440
cagaaggaga cccggaagct caaaggagag tatccaaaaa ttccaagtat aatgcagaaa   1500
gcacagaaag ggagtcacaa gacactgttg cagagaatga tgatggcggg ttcagtgagg   1560
aatgggaagc ccagagggac agtcatctag ggcctcatcg ctctacacct gagtcacgag   1620
ctgctgtcca ggaactttcc agcagtatcc tcgctggtga agacccagag gaaaggggag   1680
taaaacttgg attgggagat tcattttct acagtgttct ggttggtaaa gcctcagcaa    1740
cagccagtgg agactggaac acaaccatag cctgtttcgt agccatatta attggtttgt   1800
gccttacatt attactcctt gccattttca agaaagcatt gccagctctt ccaatctcca   1860
tcacctttgg gcttgttttc tactttgcca cagattatct tgtacagcct tttatggacc   1920
aattagcatt ccatcaattt tatatctagc atatttgcgg ttagaatccc atggatgttt   1980
cttctttgac tataaccaaa tctggggagg acaaggtga ttttcctgtg tccacatcta    2040
acaaagtcaa gattcccggc tggacttttg cagcttcctt ccaagtcttc ctgaccacct   2100
tgcactattg gactttggaa ggaggtgcct atagaaaacg attttgaaca tacttcatcg   2160
cagtggactg tgtcctcggt gcagaaacta ccagatttga gggacgaggt caaggagata   2220
tgataggccc ggaagttgct gtgccccatc agcagcttga cgcgtggtca caggacgatt   2280
tcactgacac tgcgaactct caggactacc ggttaccaag aggttaggtg aagtggttta   2340
aaccaaacgg aactcttcat cttaaactac acgttgaaaa tcaacccaat aattctgtat   2400
taactgaatt ctgaacttt caggaggtac tgtgaggaag agcaggcacc agcagcagaa    2460
tggggaatgg agaggtgggc agggttcca gcttcccttt gattttttgc tgcagactca    2520 tccttttaa atgagacttg ttttccctc tctttgagtc aagtcaaata tgtagatgcc     2580
tttggcaatt cttcttctca agcactgaca ctcattaccg tctgtgattg ccatttcttc   2640
ccaaggccag tctgaacctg aggttgcttt atcctaaaag ttttaacctc aggttccaaa   2700
ttcagtaaat tttggaaaca gtacagctat ttctcatcaa ttctctatca tgttgaagtc   2760
aaatttggat tttccaccaa attctgaatt tgtagacata cttgtacgct cacttgcccc   2820
agatgcctcc tctgtcctca ttcttctctc ccacacaagc agtctttttc tacagccagt   2880
aaggcagctc tgtcgtggta gcagatggtc ccacttattc tagggtctta ctctttgtat   2940
gatgaaaaga atgtgttatg aatcggtgct gtcagccctg ctgtcagacc ttcttccaca   3000
gcaaatgaga tgtatgccca agcggtaga attaagaag agtaaaatgg ctgttgaagc     3060
aaaaaaaaaa aaaaaaaaa aaaaaaa                                        3087
```

<210> SEQ ID NO 6
<211> LENGTH: 945
<212> TYPE: DNA
<213> ORGANISM: Homo sapiens
<220> FEATURE:
<221> NAME/KEY: misc_feature
<222> LOCATION: (1)..(945)
<223> OTHER INFORMATION: where n may be either a or g or c or t/u,
      unknown or other

<400> SEQUENCE: 6

```
gttntccnaa ccaacttagg agnttggacc tgggraagac cnacntgatc tccgggaggn    60
aaagactnca gttgagccgt gattgcaccc actttactcc aagcctgggc aaccaaaatg   120
agacactggc tccaaacaca aaaacaaaaa caaaaaaaga gtaaattaat ttanagggaa   180
```

```
gnattaaata aataatagca cagttgatat aggttatggt aaaattataa aggtgggana      240
ttaatatcta atgtttggga gccatcacat tattctaaat aatgttttgg tggaaattat      300
tgtacatctt ttaaaatctg tgtaattttt tttcagggaa gtgtttaaaa cctataacgt      360
tgctgtggac tacattactg ttncactcct gatctggaat tttggtgtgg tgggaatgat      420
ttccattcac tggaaaggtc cacttcgact ccagcaggca tatctcatta tgattagtgc      480
cctcatgncc ctgktgttta tcaagtacct ccctgaatgg actgngtggc tcatcttggc      540
tgtgatttca gtatatggta aaacccaaga ctgataattt gtttgtcaca ggaatgcccc      600
actggagtgt tttctttcct catctcttta tcttgattta gagaaaatgg taacgtgtac      660
atcccataac tcttcagtaa atcattaatt agctatagta acttttttcat ttgaagattt      720 cggctgggca tggtagctca tgcctgtaat cttagcactt tgggaggctg aggcgggcag      780
atcacctaag cccagagttc aagaccagcc tgggcaacat ggcaaaacct cgtatctaca      840
gaaaatacaa aaattagccg ggcatggtgg tgcacacctg tagttccagc tacttaggag      900
gctgaggtgg gaggatcgat tgatcccagg aggtcaagnc tgcag                     945
```

<210> SEQ ID NO 7
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: where n may be either a or g or c or t/u, unknown or other

<400> SEQUENCE: 7

```
gttgcaaagt catggattcc tttaggtagc tacattatca acctttttga gaataaaatg       60
aattgagagt gttacagtct aattctatat cacatgtaac ttttatttgg atatatcagt      120
aatagtgctt ttttttttt tttttttttt tttttttttt tttggggana gagtctcgct      180
ctgtcgccag gttggagtgc aatggtgcga tcttggctca ctgaaagctc caccncccgg      240
gttcaagtga ttctcctgcc tcagccnccc aagtagntgg gactacaggg gtgcgccacc      300
acgcctggga taattttggg nttttttagta gagatggcgt ttcaccanct tggngcaggc      360
tggtcttgga actcctgana tcatgatctg cctgccttag cctccccaaa gtgctgggat      420
tncaggggtg agccactgtt cctgggcctc                                      450
```

<210> SEQ ID NO 8
<211> LENGTH: 516
<212> TYPE: DNA
<213> ORGANISM: Homo sapiens
<220> FEATURE:
<221> NAME/KEY: misc_feature
<222> LOCATION: (1)..(516)
<223> OTHER INFORMATION: where n may be either a or g or c or t/u, unknown or other

<400> SEQUENCE: 8

```
gctcatcatg cttcacgggg gaggctgtgc gggaagaatg ctcccacaca gnataaagaa       60
tgctcccgca caggatagag aatgcccccg cacagcatag agaagccccc gcacagcata      120
gagaatgccc ccncacagca tagagaagcc cccgcacagc atagagaatg ctcttcacct      180
ctgggttttt aaccagccaa actaaaatca cagaggscma cacatcattt aagatagaaa      240
tttctgtatc ttttaatttty tttcmaagta gttttactta ttttcagatt ctatttcttt      300
```

```
actagaatta agggataaaa taacaatgtg tgcataatga accctatgaa acmaacmmaa    360
gctaggtttt tttcatagst cttcttccag attgaatgaa cgtctgttct aaaatttaac    420
cccccaggga aatattcagt taactatgtt aaaaacccag acttgtgatt gagttttgcc    480
tgaaaatgct ttcataatta tgtgtgaatg tgtgtc                              516
```

<210> SEQ ID NO 9
<211> LENGTH: 1726
<212> TYPE: DNA
<213> ORGANISM: Homo sapiens
<220> FEATURE:
<221> NAME/KEY: misc_feature
<222> LOCATION: (1)..(1726)
<223> OTHER INFORMATION: where n may be either a or g or c or t/u,
      unknown or other

<400> SEQUENCE: 9

```
ggatccctcc ccttttttaga ccatacaagg taacttccgg acgttgccat ggcatctgta    60
aactgtcatg gtgttggcgg ggagtgtctt ttagcatgct aatgtattat aattagcgta   120
tagtgagcag tgaggataac cagaggtcac tctcctcacc atcttggttt tggtgggttt   180
tggccagctt ctttattgca accagtttta tcagcaagat ctttatgagc tgtatcttgt   240
gctgacttcc tatctcatcc cgnaactaag agtacctaac ctcctgcaaa ttgmagncca   300
gnaggtcttg gncttattn acccagcccc tattcaarat agagtngytc ttggnccaaa    360
cgccyctgac acaaggattt taaagtctta ttaattaagg taagatagkt ccttgsatat   420
gtggtctgaa atcacagaaa gctgaatttg gaaaaaggtg cttggasctg cagccagtaa   480
acaagttttc atgcaggtgt cagtatttaa ggtacatctc aaaggataag tacaattgtg   540
tatgttggga tgaacagaga gaatggagca anccaagacc caggtaaaag agaggacctg   600
aatgccttca gtgaacaatg atagataatc tagacttttta aactgcatac ttcctgtaca   660
ttgttttttc ttgcttcagg ttttttagaac tcatagtgac gggtctgttg ttaatcccag   720
gtctaaccgt taccttgatt ctgctgagaa tctgatttac tgaaaatgtt tttcttgtgc   780
ttatagaatg acaatagaga acggcaggag cacaacgaca gacggagcct tggccaccct   840
ganccattat ctaatggacg acccagggta actcccggca ggtggtggan caagatgagg   900
aagaagatga gganctgaca ttgaaatatg ncgscaagca tgtgatcatg ctctttgkcc   960
ctgtgactct ctgcatggtg gtggtcgtgg ntaccattaa gtcagtcagc ttttataccc   1020
ggaaggatgg gcagctgtac gtatgagttt kgttttatta ttctcaaaasc cagtgtggct   1080 tttctttaca gcatgtcatc atcaccttga aggcctctnc attgaagggg catgacttag   1140
ctggagagcc catcctctgt gatggtcagg agcagttgag agancgaggg gttattactt   1200
catgttttaa gtggagaaaa ggaacactgc agaagtatgt ttcctgtatg gtattactgg   1260
atagggctga agttatgctg aattgaacac ataaattctt ttccacctca gggncattgg   1320
gcgcccattg ntcttctgcc tagaatattc tttcctttnc tnacttkggn ggattaaatt   1380
cctgtcatcc cctcctctt ggtgttatat ataaagtntt ggtgccgcaa aagaagtagc    1440
actcgaatat aaaattttcc ttttaattct cagcaaggna agttacttct atatagaagg   1500
gtgcacccnt acagatggaa caatggcaag cgcacatttg ggacaaggga ggggaaaggg   1560
ttcttatccc tgacacacgt ggtcccngct gntgtgtnct nccccactg antagggtta    1620 gactggacag gcttaaacta attccaattg gntaatttaa agagaatnat ggggtgaatg   1680
ctttgggagg agtcaaggaa gagnaggtag naggtaactt gaatga                  1726
```

<210> SEQ ID NO 10
<211> LENGTH: 1883
<212> TYPE: DNA
<213> ORGANISM: Homo sapiens
<220> FEATURE:
<221> NAME/KEY: misc_feature
<222> LOCATION: (1)..(1883)
<223> OTHER INFORMATION: where n may be either a or g or c or t/u, unknown or other

<400> SEQUENCE: 10

```
cncgtataaa agaccaacat tgccancnac aaccacaggc aagatcttct cctaccttcc        60
cccnnggtgt aataccaagt attcnccaat ttgtgataaa ctttcattgg aaagtgacca       120
ccctccttgg ttaatacatt gtctgtgcct gctttcacac tacagtagca cagttgagtg       180
tttgccctgg agaccatatg acccatagag cttaaaatat tcagtctggc tttttacaga       240
gatgtttctg actttgttaa tagaaaatca acccaactgg tttaaataat gcacatactt       300
tctctctcat agagtagtgc agaggtagnc agtccagatt agtasggtgg cttcacgttc       360
atccaaggac tcaatctcct tctttcttct ttagcttcta acctctagct tacttcaggg       420
tccaggctgg agccctascc ttcatttctg acagtaggaa ggagtagggg agaaaagaac       480
ataggacatg tcagcagaat tctctcctta gaagttccat acacaacaca tctccctaga       540
agtcattgcc cttacttgtt ctcatagcca tcctaaatat aagggagtca gaagtaaagt       600
ctkkntggct gggaatattg gcacctggaa taaaaatgtt tttctgtgaa tgagaaacaa       660
ggggaagatg gatatgtgac attatcttaa gacaactcca gttgcaatta ctctgcagat       720
gagaggcact aattataagc catattacct ttcttctgac aaccacttgt cagcccncgt       780
ggtttctgtg gcagaatctg gttcyatamc aagttcctaa taanctgtas ccnaaaaaat       840
ttgatgaggt attataatta tttcaatata aagcacccac tagatggagc cagtgtctgc       900
ttcacatgtt aagtccttct ttccatatgt tagacatttt ctttgaagca attttagagt       960
gtagctgttt ttctcaggtt aaaaattctt agctaggatt ggtgagttgg ggaaaagtga      1020
cttataagat ncgaattgaa ttaagaaaaa gaaaattctg tgttggaggt ggtaatgtgg      1080
ktggtgatct ycattaacac tganctaggg cttttkgkgtt tgktttattg tagaatctat      1140
accccattca nagaagatac cgagactgtg gccagagag ccctgcactc aattctgaat       1200
gctgccatca tgatcagngt cattgtwgtc atgactannc tcctggtggt tcwgtataaa      1260
tacaggtgct ataaggtgag catgagacac agatctttgn tttccaccct gttcttctta      1320
tggttgggta ttcttgtcac agtaacttaa ctgatctagg aaagaaaaaa tgttttgtct      1380
tctagagata agttaatttt tagttttctt cctcctcact gtggaacatt caaaaaatac      1440
aaaaaggaag ccaggtgcat gtgtaatgcc aggctcagag gctgaggcag gaggatcgct      1500
tgggcccagg agttcacaag cagcttgggc aacgtagcaa gaccctgcct ctattaaaga      1560
aaacaaaaaa caaatattgg aagtatttta tatgcatgga atctatatgt catgaaaaaa      1620
ttagtgtaaa atatatatat tatgattagn tatcaagatt tagtgataat ttatgttatt      1680
ttgggatttc aatgcctttt taggccattg tctcaamaaa taaaagcaga aaacaaaaaa      1740
agttgtaact gaaaaataaa catttccata taatagcaca atctaagtgg gtttttgntt      1800
gtttgtttgn ttgttgaagc agggccttgc cctnycaccc aggntggagt gaagtgcagt      1860
ggcacgattt tggctcactg cag                                              1883
```

<210> SEQ ID NO 11

```
<211> LENGTH: 823
<212> TYPE: DNA
<213> ORGANISM: Homo sapiens
<220> FEATURE:
<221> NAME/KEY: misc_feature
<222> LOCATION: (1)..(823)
<223> OTHER INFORMATION: where n may be either a or g or c or t/u,
      unknown or other

<400> SEQUENCE: 11
caggagtgga ctaggtaaat gnaagntgtt ttaaagagag atgnggncng ggacatagtg    60
gtacacanct gtaatgctca ncactkatgg ggagtactga aggnggnsgg atcacttgng   120
ggtcnggaat ntgagancag cctgggcaan atggcgaaac cctgtctcta ctaaaaatag   180
ccanaawnwa gcctagcgtg gtggcgcrca cgcgtggttc cacctactca ggaggcntaa   240
gcacgagnan tncttgaacc caggaggcag aggntgtggt garctgagat cgtgccactg   300
cactccagtc tgggcgacma agtgagaccc tgtctccnnn aagaaaaaaa aaatctgtac   360 ttttttaaggg ttgtgggacc tgttaattat attgaaatgc ttctyttcta ggtcatccat   420
gcctggctta ttatatcatc tctattgttg ctgctctttt ttacattcat ttacttgggg   480
taagttgtga aatttggggt ctgtctttca gaattaacta cctnngtgct gtgtagctat   540
catttaaagc catgtacttt gntgatgaat tactctgaag ttttaattgt ntccacatat   600
aggtcatact tggtatataa aagactagnc agtattacta attgagacat tcttctgtng   660
ctcctngctt ataataagta gaactgaaag naacttaaga ctacagttaa ttctaagcct   720
ttggggaagg attatatagc cttctagtag gaagtcttgt gcnatcagaa tgttntaaa    780 gaaagggtnt caaggaatng tataaanacc aaaaataatt gat                     823

<210> SEQ ID NO 12
<211> LENGTH: 736
<212> TYPE: DNA
<213> ORGANISM: Homo sapiens

<400> SEQUENCE: 12
gtctttccca tcttctccac agagtttgtg ccttacatta ttactccttg ccattttcaa    60
gaaagcattg tcagctcttc caatctccat caccctttggg cttgttttct actttgccac   120
agattatctt gtacagcctt ttatggacca attagcattc catcaatttt atatctagca   180
tatttgcggt tagaatccca tggatgtttc ttctttgact ataacaaaat ctggggagga   240
caaaggtgat ttcctgtgtc cacatctaac aaatcaagat cccggctgg acttttggag    300 gttccttcca agtcttcctg accaccttgc actattggac tttggaagga ggtgcctata   360
gaaaacgatt tgaacatac ttcatcgcag tggactgtgt cctcggtgca gaaactacca    420
gatttgaggg acgaggtcaa ggagatatga taggcccgga agttgctgtg ccccatcagc   480
agcttgacgc gtggtcacag gacgattttc actgacactg cgaactctca ggactaccgt   540
taccaagagg ttaggtgaag tggtttaaac caaacggaac tcttcatctt aaactacacg   600
ttgaaaatca acccaataat tctgtattaa ctgaattctg aacttttcag gaggtactgt   660
gaggaagagc aggcaccacc agcagaatgg ggaatggaga ggtgggcagg ggttccagct   720 tcccctttgat tttttg                                                  736

<210> SEQ ID NO 13
<211> LENGTH: 893
<212> TYPE: DNA
<213> ORGANISM: Homo sapiens
<220> FEATURE:
```

<221> NAME/KEY: misc_feature
<222> LOCATION: (1)..(893)
<223> OTHER INFORMATION: where n may be either a or g or c or t/u,
      unknown or other

<400> SEQUENCE: 13

| | | |
|---|---|---|
| ggatccgccc gccttggcct cccaaagtgc tgggattaca ggcatgagcc accgctcctg | 60 |
| gctgagtctg cgatttcttg ccagctctac ccagttgtgt catcttaagc aagtcactga | 120 |
| acttctctgg attcccttct cctnnwgtaa aataagnatg ttatctgncc nncctgcctt | 180 |
| gggcattgtg ataaggataa gatgacatta tagaatntng caaaattaaa agcgctagac | 240 |
| aaatgatttt atgaaaatat aaagattagn ttgagtttgg gccagcatag aaaaaggaat | 300 |
| gttgagaaca ttccnttaag gattactcaa gcyccccttt tgstgknwaa tcaganngtc | 360 |
| atnnamntat cntntgtggg ytgaaaatgt ttggttgtct caggcggttc ctacttattg | 420 |
| ctaaagagtc ctaccttgag cttatagtaa atttgtcagt tagttgaaag tcgtgacaaa | 480 |
| ttaatacatt cctggtttac aaattggtct tataagtatt tgattggtnt aaatgnattt | 540 |
| actaggattt aactaacaat ggatgacctg gtgaaatcct atttcagacc taatctggga | 600 |
| gcctgcaagt gacaacagcc tttgcggtcc ttagacagct tggcctggag gagaacacat | 660 |
| gaaagaaagg tttgtttctg cttaatgtaa tctatggaag tgtttttat aacagtataa | 720 |
| ttgtagtgca caaagttctg ttttctttc ccttttcaga acctcaagag gctttgtttt | 780 |
| ctgtgaaaca gtatttctat acagtntgct ccaantgnac agagttacct gcacnncgtt | 840 |
| gtccntactt ccagaatgca cagatgtctg aggacaacca cctgagcaat act | 893 |

<210> SEQ ID NO 14
<211> LENGTH: 475
<212> TYPE: DNA
<213> ORGANISM: Homo sapiens
<220> FEATURE:
<221> NAME/KEY: misc_feature
<222> LOCATION: (1)..(475)
<223> OTHER INFORMATION: where n may be either a or g or c or t/u,
      unknown or other

<400> SEQUENCE: 14

| | | |
|---|---|---|
| tcagaaaata ctttngggca catgagaatc acatgagaac aagctgatgc ataattcctc | 60 |
| ctgtgatgga atgtaatagt aatttaacag tgtcctttct ttttaactgc ctcaaggata | 120 |
| cagcaaaata aaacaaaagc aatatgaagg ctgagaatag gtatcagatt atcataaaaa | 180 |
| gtatagatca aaaggaatct ggtkctnagg ttggcgcagc agcctctaga agcgacnagg | 240 |
| gagacttta gaactaccat tctcctctat aagtggatcc nangcccagg raaacttgat | 300 |
| attgagnaca atggccttac tgaaataacc tgtgatccac tcggnctcat catctccacc | 360 |
| accaccataa atttgatgag tncctataat attccancca gnggaaatac ctggraggtt | 420 |
| actgaaaggc nacnatcaga cnaaaataaa gnataccgta ggtaaattct acagt | 475 |

<210> SEQ ID NO 15
<211> LENGTH: 180
<212> TYPE: DNA
<213> ORGANISM: Homo sapiens
<220> FEATURE:
<221> NAME/KEY: misc_feature
<222> LOCATION: (1)..(180)
<223> OTHER INFORMATION: where n may be either a or g or c or t/u,
      unknown or other

<400> SEQUENCE: 15

```
gttctcnaga tctcttcaaa attcattntg cgctatagga gctgggatta ccgcgggtgc    60
tggaaccaga cttgcnctcc aatggatcct ccanacngga nggggggtgg actcacacca   120
tttacagggg gctcgtaaag aatcctgttt tgantattnt nccgtcaatt accncccaa    180
```

<210> SEQ ID NO 16
<211> LENGTH: 457
<212> TYPE: DNA
<213> ORGANISM: Homo sapiens
<220> FEATURE:
<221> NAME/KEY: misc_feature
<222> LOCATION: (1)..(457)
<223> OTHER INFORMATION: where n may be either a or g or c or t/u,
      unknown or other

<400> SEQUENCE: 16

```
aatgtaacma cmaaaccyca aactcctgna agaanatggt tacttatnga tnccatttnc    60
tttttncact ctcagacata aatataaacm mantttctac tgtggraaaa catctncagg   120
ggncntttan ccatgatctc tagnacnang ggctngtggn tngttttaat gtctctaagc   180
nactngacta gtttctcttn cactgagnaa actgcnacaa gtnnttnctn ctgnatctgn   240
actgnaatgc taagttncaa gtnccaatga gctngtgant tanyctttat ttnamcnaaa   300
gtnnttaatc anccncagtg ttactttgna aagctnctcc ctggacaggc ggcccnactt   360
ctaatgttat gaatgggctg gagnancctc nacntgagtt tnnwaaggnt caacanccaa   420
trgnaantgt amccgactct aaattccaac cnataat                            457
```

<210> SEQ ID NO 17
<211> LENGTH: 373
<212> TYPE: DNA
<213> ORGANISM: Homo sapiens
<220> FEATURE:
<221> NAME/KEY: misc_feature
<222> LOCATION: (1)..(373)
<223> OTHER INFORMATION: where n may be either a or g or c or t/u,
      unknown or other

<400> SEQUENCE: 17

```
atctgtgcta ggtagtgtac taatcattca gtttatctca tttaatctnn atgnaactct    60
aagtcattcg ctntgancna cacataacag atctcgcaac tgnagtttag cgaggccagt   120
taatttkcca aagntcataa tnctaagnag ttctagnatg gagattcmaa gtccnactgt   180
ttagtcaaga gaccctactg ttaactagta cctttacact actaactggg taanccataa   240
ncaattaatg ataaagattg agattactkc cacattctca ctggttataa attaaaacnt   300
caaataaaaa ntcttggcac ttctatggta atatttttat taggataaac tttcaagnag   360
tggatnctag gtg                                                      373
```

<210> SEQ ID NO 18
<211> LENGTH: 422
<212> TYPE: DNA
<213> ORGANISM: Homo sapiens
<220> FEATURE:
<221> NAME/KEY: misc_feature
<222> LOCATION: (1)..(422)
<223> OTHER INFORMATION: where n may be either a or g or c or t/u,
      unknown or other

<400> SEQUENCE: 18

```
cccacactgn tgggccatgg aagccatgag tgtaccacat ggccctgtcc cactggccac    60
agtngattgg ttggntcggg agtagtcacc tgattcaagn tgggccaatc agatcctacc   120
```

```
tccanggggt tnggaattag aaaacagtga ccctagytag tntaggcnac ttgaactgga      180
gggcccatac attcaggagc cttatggggc catgtacaca tggaagcagg aagantgaag      240
gagggagaag tagaggccag aaacccacct gggttcctgt ttcccaatgn taagtccctg      300
ccatgtycct gctcttcctg tggttnggat cttcaaaggt tgctcaaatt nggggcagtg      360
gccctggcag cttttcaaat cctycccatt tttattgaag ctgaaagacc cttgactaga      420
ac                                                                    422

<210> SEQ ID NO 19
<211> LENGTH: 395
<212> TYPE: DNA
<213> ORGANISM: Homo sapiens
<220> FEATURE:
<221> NAME/KEY: misc_feature
<222> LOCATION: (1)..(395)
<223> OTHER INFORMATION: where n may be either a or g or c or t/u,
      unknown or other

<400> SEQUENCE: 19
attgttattt ttcgtcacta cctccccggg tcgggagtgg gtaatttgcg cgcctgctgc      60
cttccttgga tgtggtagcc gtttctcagg ctccctctcc ggaatcgaac cctgattccc     120
cgtcacccgt ggtcaccatg gttaggcacg gcgactacca tcgaaagtta ataggggcaga    180 tctcgagaat tctcgagatc tccntcmaat tattacttca nttkcggtag tgatcagnac     240
naggcagttc tattgatttc tctcctttca ttctgagttt ctccataaat taattggacc     300
taatcatgtt tknaatcctg tcttttaggg ggnanttgna ctntcaagtg tttaaaggga     360
gggncggagn atgattntgg attggagtga gagca                                395

<210> SEQ ID NO 20
<211> LENGTH: 487
<212> TYPE: DNA
<213> ORGANISM: Homo sapiens
<220> FEATURE:
<221> NAME/KEY: misc_feature
<222> LOCATION: (1)..(487)
<223> OTHER INFORMATION: where n may be either a or g or c or t/u,
      unknown or other

<400> SEQUENCE: 20 caganttct gggtnaaaag gacctnanac ataatatagt ggacttncaa taaacactta       60
ccaaatggan aaatgaaccc ctggtcaccc cgatctcact agtncctncc ctgaaacccg     120
ananatctga gtccttttct cctttactaa cccttnctcc aatcctgctc atgggaatta     180
angntgtaaa atangcctgg ggnacctcgg rcctctnccc tgggntctgt gggtgggagn     240
actgtggaag ccgtwtcaat cgcccccacc tatgagagcc tttctncagg gccagccatg     300
aacgtccccc atgtnatcag natctncagg ctactgctgt ccttcytgga twtttaacct    360
ggrggcgggc cagggacaga aaarggaggt ggcaagatcc ttgaacaaaa ggagctataa    420
aagggcgttg ggggaagcaa ggcaaacggc agattaaaca agcaggcacc tcaaggaaac    480
gtgacgc                                                               487

<210> SEQ ID NO 21
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
``` unknown or other

<400> SEQUENCE: 21

| ctcgagatct | ggcccatcat | ttagttttat | ngcttgnagt | ntntagnaga | taaaacatcc | 60 |
| acgtggatct | nctcttagag | aaatcaanta | ctttaggnat | ntgatagtca | gagantggnt | 120 |
| atcaaatnga | aaggnatntn | ggtngancag | ttagttngyn | ccnttngnng | agaccactgg | 180 |
| gntgtngasa | ccagattcmk | gggtncaat | cttanggtaa | tctnagagcc | aacacatggg | 240 |
| tcatnttats | ccccaaactt | agccacatct | bgtggggyta | tggngtcacc | ccaagagcag | 300 |
| gaggagcatg | gntggatgga | aatccatctc | caccactgga | accccaawtt | ctgaatgnat | 360 |
| cacctgttag | agtttcttgt | ycataaaata | gcagggaatt | taggaattta | gttttttttt | 420 |
| aatagtttgg | gccttttatc | cacactctca | ggagcttagg | atacttttct | ccttcagctc | 480 |
| actctgaaac | tccctctgga | | | | | 500 |

<210> SEQ ID NO 22
<211> LENGTH: 406
<212> TYPE: DNA
<213> ORGANISM: Homo sapiens
<220> FEATURE:
<221> NAME/KEY: misc_feature
<222> LOCATION: (1)..(406)
<223> OTHER INFORMATION: where n may be either a or g or c or t/u, unknown or other

<400> SEQUENCE: 22

| tcgagatctg | tggtagtnac | atgatattct | ggcamctact | ttcattatca | cctttattaa | 60 |
| aataaattta | agaaaaaatg | gcagtatgtt | tctgtgragn | ccacgagtac | tcattttaaa | 120 |
| ggactcmaga | gttncagrna | agtaaaaagr | aaagagtaaa | atcattttct | aantytywyy | 180 |
| ttccagaaat | aacgatgttg | agcattaagt | ggacttcatt | tcatactctt | tcmmagntta | 240 |
| tgtaggcata | wawatgtgtg | tgtatataca | tatatatggg | tacatcctta | gagaagttgg | 300 |
| ctggctagat | agacacacnt | naaaaatggr | atcatactct | aatkccattt | nnantttana | 360 |
| aaatacatat | tcaganccnc | tgtncttata | nacagagtaa | ntgaaa | | 406 |

<210> SEQ ID NO 23
<211> LENGTH: 289
<212> TYPE: DNA
<213> ORGANISM: Homo sapiens

<400> SEQUENCE: 23

| gacccagtaa | aacttatctc | atgagcataa | ggctgaatgg | gattgacagc | ctacagaacc | 60 |
| cggattttat | catgagggca | ttagtggggg | ttgggggtta | ggtactgaaa | gtttaaggag | 120 |
| gtgaaaggaa | agcaacttgt | gccttacagg | gtcaagctag | gtcaaggaaa | ttcccaggag | 180 |
| cgtgtggaag | ctctctacct | gataggtgag | ctcaagctta | tgaccgccca | agcttctccc | 240 |
| caagcttccc | ttccactgct | tcctcttgat | tgacttccac | agcaaggtc | | 289 |

<210> SEQ ID NO 24
<211> LENGTH: 367
<212> TYPE: DNA
<213> ORGANISM: Homo sapiens
<220> FEATURE:
<221> NAME/KEY: misc_feature
<222> LOCATION: (1)..(367)
<223> OTHER INFORMATION: where n may be either a or g or c or t/u, unknown or other

<400> SEQUENCE: 24

```
ccatcaggat ttactgagta aaaatctcag gtnttaacca tgccctaaa atgtgctatn      60 ccaaagagga acaggttact tgggaggaaa aaagctgcct gggnaactcc ccncaaatgt    120
ttattttaaa taaaaatggt ngatggaaat attttntaaa agaacttggg gtntaatatg    180
gnatactgcc catcaaacaa aaaggaaat aaaacttcnt tcccatttat aataagttnc    240
ccacccttta ctatcaagat tacaacttat tgaccttta tgctngctng gttttttgg     300 gactgcctaa tccaatgttt aaattttcta ngtctgnatt tcaatgtggg taggagtnat   360
ttttcaa                                                              367
```

```
<210> SEQ ID NO 25
<211> LENGTH: 425
<212> TYPE: DNA
<213> ORGANISM: Homo sapiens
<220> FEATURE:
<221> NAME/KEY: misc_feature
<222> LOCATION: (1)..(425)
<223> OTHER INFORMATION: where n may be either a or g or c or t/u,
      unknown or other

<400> SEQUENCE: 25
gagtatctga caggtaagat tgctttttaa agttgtttta aatgcattac atgactgaga    60
aaagaaaaat gcacatttta ttgttgcagt ttaaaatttc atttngngtg aaactaaacg   120
tgaaacaaaa gggataaatg tgttttgntt ttgttttggt tttacctgtt tggggtattt   180
ttttctgagt ttgtgtagaa acccgtgtgg ntacactggg taatcttgtc agggntacma   240
amcttgggtc ttganttttgg ttanttggnt ttanttggtg nacccatgta cttgctcttc   300
cntcccagaa acatagcttg gtaggcnagg gttaanccag tgtcggcgan cccatgtccc   360
tancacagca tcttgtaagt ttaatgcaca atcgttccnt cccaggatgg anttatcatt   420
ataaa                                                                425
```

```
<210> SEQ ID NO 26
<211> LENGTH: 2377
<212> TYPE: DNA
<213> ORGANISM: Homo sapiens
<220> FEATURE:
<221> NAME/KEY: misc_feature
<222> LOCATION: (1)..(2377)
<223> OTHER INFORMATION: where n may be either a or g or c or t/u,
      unknown or other

<400> SEQUENCE: 26
gagaggcgca ggagccacaa ataaagcaag agccagaatc agaagnggag gaagaagaaa    60
agcaagaaaa agragraana cgagaagaac ccatggraga ggaagaggan ccagancmaa   120
agccttgtct gaaacctact ctgaggccca tcagctctgc tccatctgtt tcctctgcca   180
gtggnaatgc nacacctaac actcctgggg atgagtctcc ctgtggtatt attattcctc   240
atgraaactc accagatcaa cagcaacctg aggagcatag gccmaaaata ggactaagtc   300
ttaaactggg tgcttccaat agtcctggtc agcctaattc tgtgaagaga aagaaactac   360
ctgtagatag tgtcttttaac aaatttgagg atgaagacag tgatgacgta ccccgaaaaa   420
ggaaactggt tcccttggat tatggtgaag atgataaaaa tncaaccaaa ggcactgtaa    480
acactgaaga aaagcgtaaa cacattaaga gtctcattga gaaaatccct acagccaaac    540
ctgagctctt cgcttatccc ctggattggt ctattgtgga ttctatactg atggaacgtc    600
gaattagacc atggattaat aagaaaatca tagaatatat aggtgaagaa gaagctacat    660
```

| | |
|---|---:|
| tagttgattt ngtttgttct aaggttatgg ctcatagtnc accccagagc attttagatg | 720 |
| atgttgccat ggtacttgat gaagaagcag aagtttttat agtcaaaatg tggagattat | 780 |
| tgatatatga aacagaagcc aagaaaattg gtcttgtgaa gtaaaacttt ttatatttag | 840 |
| agttccattt cagatttctt ctttgccacc cttttaagga cttkgaattt ttctttgtct | 900 |
| tkgaagacat tgtgagatct gtaattttt ttttttgtag aaaatgtgaa ttttttggtc | 960 |
| ctctaatttg ttgttgccct gtgtactccc ttggttgtaa agtcatctga atccttggtt | 1020 |
| ctctttatac tcaccaggta caaattactg gtatgtttta taagccgcag ctactgtaca | 1080 |
| cagcctatct gatataatct tgttctgctg atttgtttct tgtaaatatt aaaacgactc | 1140 |
| cccaattatt ttgcagaatt gcacttaata ttgaaatgta ctgtatagga accaacatga | 1200 |
| acaattttaa ttgaaaacac cagtcatcaa ctattaccac ccccactctc ttttcatcag | 1260 |
| aaatggcaag cccttgtgaa ggcatggagt ttaaaattgg aatgcaaaaa ttagcagaca | 1320 |
| atccattcct actgtatttc tgtatgaatg tgtttgtgaa tgtatgtgta aaagtctttc | 1380 |
| ttttccctaa tttgctttgg tggggtcctt aaaacatttc ccaactaaag aatagaattg | 1440 |
| taaaggaaaa gtggtactgt tccaacctga atgtctgtt ataattaggt tattagtttc | 1500 |
| ccagagcatg gtgttctcgt gtcgtgagca atgtgggttg ctaactgtat ggggttttct | 1560 |
| tattaataag atggctgctt cagcttctct tttaaaggaa tgtggatcat agtgattttt | 1620 |
| cctttaatt ttattgctca gaaatgaggc atatccctaa aaatctcgga gagctgtatt | 1680 |
| taatgcattt ttgcactaat tggtccttag tttaattcta ttgtatctgt ttatttaaca | 1740 |
| aaaaattcat catatcaaaa agtgtaagtg aaaaccccct ttaaaacaaa acaaaaaaat | 1800 |
| gaaataaaat taggcaaatt gacagacagt gagagtttta caaacatgat aggtattctg | 1860 |
| ctcggcaatt tgtaagttta catgttattt aaggataaag gtaaatcatt caaggcagtt | 1920 |
| accaaccact aactatttgt tttcattttt gtccttgtaga aggtttatat cttgttttac | 1980 |
| cttggctcat tagtgtttaa aaatgtactg atgatgtgct tagagaaatt cctggggctt | 2040 |
| tcttcgttgt agatcagaat ttcaccaggg agtaaaatta cctgaaaacg taagaagttt | 2100 |
| taaacagctt tccacacaaa ttagatgcaa ctgttcccat gtctgaggta cttatttaaa | 2160 |
| agaaaggtaa agattggcct gttagaaaaa gcataatgtg agctttggat tactggattt | 2220 |
| ttttttttt taaacacacc tggagaggac atttgaaaac actgttctta ccctcgaacc | 2280 |
| ctgatgtggt tccattatgt aaatatttca aatattaaaa atgtatatat ttgaaaaaaa | 2340 |
| aaaaaaaaa aaaattcctg cggccgcaag ggaattc | 2377 |

<210> SEQ ID NO 27
<211> LENGTH: 489
<212> TYPE: DNA
<213> ORGANISM: Homo sapiens
<220> FEATURE:
<221> NAME/KEY: misc_feature
<222> LOCATION: (1)..(489)
<223> OTHER INFORMATION: where n may be either a or g or c or t/u, unknown or other

<400> SEQUENCE: 27

| | |
|---|---:|
| attggagctc caccgcggtg gcggccgctc tagnaactag tggatccccc gggctgcagg | 60 |
| aattctcgag atctccccca agtaaatgaa tgaaaaaaag aacagcaaca atagagatga | 120 |
| tataataagc caggcatgga tgaccttata gcaccctgta tttatacaga accaccagga | 180 |
| ggatagtcat gacaacnatg acactgatca tgatnccagc attcagaatt gagtncaggg | 240 |

-continued

| | |
|---|---|
| ctctctggcc cacagtctcg gtatcttctg tgnatggggt atagattarc tgtccatcct | 300 |
| tccgggnata aaanctgact gacttaatgg tanccacgac caccacccat kcagagagtc | 360 |
| acagggacma aagagcatga tcaacatgct tggcnccata tttcaatntc anctcctcat | 420 |
| cttcttcctc atcttnctcc accacctncc gggagttaac cctggggtcg tccattagat | 480 |
| aatggctca | 489 |

<210> SEQ ID NO 28
<211> LENGTH: 2307
<212> TYPE: DNA
<213> ORGANISM: Homo sapiens

<400> SEQUENCE: 28

| | |
|---|---|
| agggtgcttc agtgtggctg acacagcagc atggtcttga caagttttct tcatcctacc | 60 |
| acaaaatccc agttggtaat agagacttta ctcctaccta tcaaaaccac aaaatgtccc | 120 |
| attaggggg gacatgttgt acatgttagg atcattcaaa taaccaagat tataaggtga | 180 |
| ggaaagatgc ccctaactga ttcttttgtc tctcatcttg ttggttccag ggaccgagtg | 240 |
| gggtcaatct tctggtsstg cctctccagg tctcttccag ccggtcata gacgtactcc | 300 |
| ctctgaggcc gaccgatggt tagaagaggt gtctaagagc gtccgggctc agcagcccca | 360 |
| ggcctcagct gctcctctgc agccagttct ccagcctcct ccacccactg ccatctccca | 420 |
| gccagcatca cctttccaag ggaatgcatt cctcacctct cagcctgtgc cagtgggtgt | 480 |
| ggtcccagcc ctgcaaccag cctttgtccc tgcccagtcc tatcctgtgg ccaatggaat | 540 |
| gccctatcca gcccctaatg tgcctgtggt gggcatcact ccctcccaga tggtggccaa | 600 |
| cgtwtttggc actgcaggcc accctcaggc tgcccatccc catcagtcac ccagcctggt | 660 |
| caggcagcag acattcccte actacgaggc aagcagtgct accaccagtc ccttctttaa | 720 |
| gcctcctgct cagcacctca acggttctgc agctttcaat ggtgtagatg atggcaggtt | 780 |
| ggcctcagca gacaggcata cagaggttcc tacaggcacc tgcccagtgg atccttttga | 840 |
| agcccagtgg gctgcattag aaaataagtc caagcagcgt actaatccct ccctaccaa | 900 |
| cccttcctc agtgacttac agaagacgtt tgaaattgaa ctttaagcaa tcattatggc | 960 |
| tatgtatctt gtccataccc gacagggagc aggggtagc ggtcaaagga gcmaaacaga | 1020 |
| ytttgtctcc tgattagtac tcttttcact aatcccaaag gtcccaagga acaagtccag | 1080 |
| gcccagagta ctgtgagggg tgattttgaa agacatggga aaaagcattc ctagagaaaa | 1140 |
| gctgccttgc aattaggcta agaagtcaa ggaaatgttg ctttctgtac tccctcttcc | 1200 |
| cttacccct tacaaatctc tggcaacaga gaggcaaagt atctgaacaa gaatctatat | 1260 |
| tccaagcaca tttactgaaa tgtaaaacac aacaggaagc aaagcaatgt cccttttgttt | 1320 |
| ttcaggccat tcacctgcct cctgtcagta gtggcctgta ttagagatca agaagagtgg | 1380 |
| tttgtgctca ggctgggaac agagaggcac gctatgctgc cagaattccc aggagggcat | 1440 |
| atcagcaact gcccagcaga gctatatttt ggggagaag ttgagcttcc attttgagta | 1500 |
| acagaataaa tattatatat atcaaaagcc aaaatcttta ttttatgca tttagaatat | 1560 |
| tttaaatagt tctcagatat taagaagttg tatgagttgt aagtaatctt gccaaaggta | 1620 |
| aaggggctag ttgtaagaaa ttgtacatra gattgattta tcattgatgc ctactgaaat | 1680 |
| aaaaagagga aaggctggaa gcatgcagac aggatcccta gcttgttttc tgtcagtcat | 1740 |
| tcattgtaag tagcacattg caacaacaat catgcttatg accaatacag tcactaggtt | 1800 |
| gtagttttt ttaaataaag gaaaagcagt attgtcctgg tttttaaacct atgatggaat | 1860 |

-continued

```
tctaatgtca ttattttaat ggaatcaatc gaaatatgct ctatagagaa tatatctttt    1920
atatattgct gcagtttcct tatgttaatc ctttaacact aaggtaacat gacataatca    1980
taccatagaa gggaacacag gttaccatat tggtttgtaa tatgggtctt ggtgggtttt    2040
gttttatcct ttaaattttg ttcccatgag ttttgtgggg atggggattc tggttttatt    2100
agctttgtgt gtgtcctctt cccccaaacc ccctttggt gagaacatcc ccttgacagt     2160
tgcagcctct tgacctcgga taacaataag agagctcatc tcattttac ttttgaacgt     2220 tggcgcttac aatcaaatgt aagttatata tatttgtact gatgaaaatt tataatctgc    2280
tttaacaaaa ataaatgttc atggtag                                        2307
```

```
<210> SEQ ID NO 29
<211> LENGTH: 343
<212> TYPE: DNA
<213> ORGANISM: Homo sapiens
<220> FEATURE:
<221> NAME/KEY: misc_feature
<222> LOCATION: (1)..(343)
<223> OTHER INFORMATION: where n may be either a or g or c or t/u,
      unknown or other

<400> SEQUENCE: 29
ggcagctatt tacatggcct cacaggcatc agctgaaaag aggacccmaa aagaaattgg     60
agatattgct ggtgttgctg atgttacaat cagrcagttc tatagactga tctatcctcg    120
agccccagat ctgttcctta cagacttcma attkgacacc ccagtggaca aactaccaca    180
gctataaatt gaggcagyta acgtcmaatt cttgannacm aaacttkncc tgttgtacat    240
agcctatacm aaatgctggg ttgagccttt cataaggnaa aacmnaagac atggntacgc    300
attccagggc tkgantactt attgcttggc attcttgtat gta                      343
```

```
<210> SEQ ID NO 30
<211> LENGTH: 363
<212> TYPE: DNA
<213> ORGANISM: Homo sapiens
<220> FEATURE:
<221> NAME/KEY: misc_feature
<222> LOCATION: (1)..(363)
<223> OTHER INFORMATION: where n may be either a or g or c or t/u,
      unknown or other

<400> SEQUENCE: 30
aaagggctaa ccagccactg caccaaaatt agtccttaca ttataatact ctggccattg     60
gaagagaaaa atgggaaaat tcaacaattt gaaagactat gatccctctg gctcatgatc    120
tactgaccag aatgaagtcc tgaaggattt ccttctgtta tgttatctac ccagctaatc    180
tcaaacaaga ggagctggaa agaacaaagc cccatgaagc taccctaga cccagaaagc     240 caagaacagg gccaagaaaa tgaacagcag acaagcctga aatagaagtg gnacagacat    300
gtggnaagac caagtacacc cagttnggtg gtaaagattc cgatatcaag cttatcgata    360
ccg                                                                  363
```

```
<210> SEQ ID NO 31
<211> LENGTH: 362
<212> TYPE: DNA
<213> ORGANISM: Homo sapiens
<220> FEATURE:
<221> NAME/KEY: misc_feature
<222> LOCATION: (1)..(362)
<223> OTHER INFORMATION: where n may be either a or g or c or t/u,
      unknown or other
```

<400> SEQUENCE: 31

```
agtacatggt ttcttgncca ccccasccac ctttccccat ctctaccggy tgatagtctc      60
tcagntagta gaccttttct ngtttagrca gggccacntt tttaaaaact ccagacgggt     120
accctccatg tkgmaggcga cgtggccctg gatcactcaa ctgantgtca tnkgantggt     180
gcccccagag tgaggacaat ggtgnagccc tcctaaggcc ctncctgagt gtccctcctt     240
catgaagatg attctgaggn ttcccaggcc tncacccttc ttkgaaarcc catagnagtt     300
catatgnact nctctnctat gctcaccaaa ctctnccttc atcatacttg ggggatgtgt     360
gt                                                                   362
```

<210> SEQ ID NO 32
<211> LENGTH: 475
<212> TYPE: DNA
<213> ORGANISM: Homo sapiens
<220> FEATURE:
<221> NAME/KEY: misc_feature
<222> LOCATION: (1)..(475)
<223> OTHER INFORMATION: where n may be either a or g or c or t/u, unknown or other

<400> SEQUENCE: 32

```
gtgcatgtaa ttacagttac gatatatgaa acgtacaaaa tattatgagt atataatatg      60
gggagactta atctagtttg ggggatcagg gcacatttct ctaagaaagt gacatttgaa     120
ttgagctctg aaggataaat agacattacc cagaagaata aaatgatggg gaagaaggag     180
gacattttcc gtagatttcc agtggccccn cttgatccct tatccactca tcactnagga     240
ggatattaaa tkctatagaa atggragraa gacmmaaaga gaccctnata tctcgagagg     300
atccagcmaa attccaagag acacaacawt aagaaactng gaaggaagag aaaaggcmmn     360
nnaggnaaaa gaaagacaag gaaattnwnn nagnacggag agaaagagag agggagcgtn     420
naagggnacg agaaaggcga gnacggggac gagaaagggn aagagnacgt aaacg          475
```

<210> SEQ ID NO 33
<211> LENGTH: 346
<212> TYPE: DNA
<213> ORGANISM: Homo sapiens
<220> FEATURE:
<221> NAME/KEY: misc_feature
<222> LOCATION: (1)..(346)
<223> OTHER INFORMATION: where n may be either a or g or c or t/u, unknown or other

<400> SEQUENCE: 33

```
ggaaataaat gagatctcag tggtggtatg gattggactg atctctgtaa ctgtgtntgg      60
aaaaaggacc ggaaaatgaa agccagatcc cagtaagggg tagagagggg ccaagagaac     120
tgaacatctg ggctgccgga gaaatcaaag tctaggaagt aagaggtaag agtgtactac     180
aggggacata ccccaatctc ttggttccct ccctctncct tcctctccca gagacccagg     240
tccctgggac tatnttggat ctgtctctga agctgaaaaa caaaaggcag aggagacagt     300
cggntctaag tgaccaatct caagccagct tggtcagaan tcctaa                    346
```

<210> SEQ ID NO 34
<211> LENGTH: 433
<212> TYPE: DNA
<213> ORGANISM: Homo sapiens
<220> FEATURE:
<221> NAME/KEY: misc_feature
<222> LOCATION: (1)..(433)

<223> OTHER INFORMATION: where n may be either a or g or c or t/u,
unknown or other

<400> SEQUENCE: 34

| | | | | | |
|---|---|---|---|---|---|
| aaatccagtg | caggcaacat | tatgtggaaa | tagaaacagg | gctcctgcta | ggagattgan | 60 |
| attctggctt | tcctttggaa | cccctcactg | actcatcgcc | cctgaancag | ganccancag | 120 |
| gtnccaaggc | tcccctgctc | ctntccctnc | cccagggcga | gataggaarc | cggaarcctg | 180 |
| ggcaggctga | rcccanccga | ctggaaccag | ggnagancct | gtgggtgggt | ggnagggagg | 240 |
| gaaggaggcc | agattcctcc | agaactgggg | ragagaacag | gttttggaag | ttgggggagg | 300 |
| gtttgggttt | cacagtgatg | gtttcatgan | accctggagg | gttncacact | cctggtkcan | 360 |
| ttttgntant | cgtncttga | anacarnccg | cttccttca | accctccncn | taaaaagttt | 420 |
| tgatntttta | agg | | | | | 433 |

<210> SEQ ID NO 35
<211> LENGTH: 350
<212> TYPE: DNA
<213> ORGANISM: Homo sapiens
<220> FEATURE:
<221> NAME/KEY: misc_feature
<222> LOCATION: (1)..(350)
<223> OTHER INFORMATION: where n may be either a or g or c or t/u,
unknown or other

<400> SEQUENCE: 35

| | | | | | |
|---|---|---|---|---|---|
| accaagagcc | cccagtttat | gntaactctc | atgacaaaca | caattttagt | acctctcact | 60 |
| accaactatc | caggaaccag | gantcaccta | ttactacggt | tccagcagaa | tgggaatccc | 120 |
| attctcggat | atccagggta | aatccctgac | catgtgagag | gaatcctagt | gccccaacaa | 180 |
| cctcaccccc | tgactcctcc | tcaanggctc | tgccaagtca | acaaaaaaat | cctctacatt | 240 |
| tacactatct | gtaaagccaa | agaccagcgt | caacctaaat | gtccatcaat | aagggaatgg | 300 |
| ttggataagt | aaaaattatg | cagctgtagg | aaggaatgaa | gaatgtctat | | 350 |

<210> SEQ ID NO 36
<211> LENGTH: 512
<212> TYPE: DNA
<213> ORGANISM: Homo sapiens
<220> FEATURE:
<221> NAME/KEY: misc_feature
<222> LOCATION: (1)..(512)
<223> OTHER INFORMATION: where n may be either a or g or c or t/u,
unknown or other

<400> SEQUENCE: 36

| | | | | | |
|---|---|---|---|---|---|
| aaagggaaca | aaagctggta | ccgggccccc | cctcgaggtc | gacggtatcg | ataagctgga | 60 |
| tatcgaatcc | tcgagatcta | cctaaaaaaa | aaaaattaac | ttcccaaatg | tgggagtcta | 120 |
| ctctgttccc | tcctngtntt | tattnctgtn | tactttycta | anatggttaa | aatgtgtaan | 180 |
| caatatgtgt | cctttnactn | kggkgtgaac | attttttycta | ttataaatyc | twagaaaata | 240 |
| ttnctatggn | tatgagatat | tkgattccaa | gtgcctkgta | atttactyct | caaatgtccc | 300 |
| tgatgtkgga | nattkgttnc | tagtgttyca | ctatttaaaa | aaacagnaat | atctgtctnt | 360 |
| atgctnagag | cttntycagt | ttycaaatta | ttnccttagg | gtaaaatcct | agaagtagaa | 420 |
| ttttgggc | aaattatcta | catatttata | attgtcttgg | tattccaaat | ctcgttttcc | 480 |
| aaaagcttat | atcaatttgt | acttaacacc | ag | | | 512 |

<210> SEQ ID NO 37

```
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: where n may be either a or g or c or t/u,
      unknown or other

<400> SEQUENCE: 37
atttaagatg actggggtc tctncctaat cccatactcc actggagagg anaagtggga      60
aaggttggtc tagttarggt ngntggggac cctcccaaga gctgnagaag cagagataag   120
nagagcctnc tnctaaatcc acatggncct yccaaggntc tcatcctcta ggacctacca   180
ctnctcagtc tacttacttg tctyctgana tgctttctng aggggnagaa aacaaaggaa   240
gagtaataac aagcagnaga aactgcagag aatgnaaaat aagtccatag gagaatgttg   300
naaatagaat catccncctt tacatattgt cactccagga aaactgccaa gaaccactca   360
ttcctctaga tacamttcct gtaggatccy cccagacttc ctcccttaag cacgtcagta   420
ttctccttat tctcccttca tttcaaccct                                     450

<210> SEQ ID NO 38
<211> LENGTH: 766
<212> TYPE: DNA
<213> ORGANISM: Homo sapiens
<220> FEATURE:
<221> NAME/KEY: misc_feature
<222> LOCATION: (1)..(766)
<223> OTHER INFORMATION: where n may be either a or g or c or t/u,
      unknown or other

<400> SEQUENCE: 38
cgagatctgc cccagcccac atttcctttg ttgaatgagt agagaagact gagaagtatc    60
actcacccgt gatgtggttt gtccctttc cagccagtgt gttggtaata aaagtcacct   120
ttcagagctt tggtccccgt aatgcccgtc tttcctgtgt ccaggaataa cctttgntac   180
taggcagtcc tctgaaagat ttgtagaagg ttaaagtgga aagggacttg gaagctcata   240
gaatccatgc ctcttctttt agcatcaagg aattagaagt cctgagagat gaagaatgtt   300
gtcttcccaa ctcaaaccca tttcttgaag ccatttccct ggttactgna ttggccacaa   360
cccttccccc ttgntatcct catcctgcta atgctgtttt taatggcctg ccagtctgga   420
tttgtctttg gcaaccaaac aattttgctt cacaagattc ctacttaagg gaagagaggg   480
gctcctcatt tntcacttgt acaagagcag ggctggtcag ctttacacag gtgtcagatg   540
aaccgtcaca anccagantt ncatgttggc ctcaggaggg cttcnaggtc caacatctcg   600
acgtaaggag cgttcccagt tctttcatgc tcagataaca gtnctaactn cagctgtttc   660
atcccnaatc cctanttgag gtcttaacat ctattccatt ttkccnacma gggttatnct   720
gttaaccctc tncaccagan ttaganctga ctgatncact tcctag                  766

<210> SEQ ID NO 39
<211> LENGTH: 327
<212> TYPE: DNA
<213> ORGANISM: Homo sapiens
<220> FEATURE:
<221> NAME/KEY: misc_feature
<222> LOCATION: (1)..(327)
<223> OTHER INFORMATION: where n may be either a or g or c or t/u,
      unknown or other

<400> SEQUENCE: 39
```

```
tcatacttgt atagttcknt aagataatca ctctctcact cagacatnng gngrarngcc      60
cntcgatcac ttggganagg ngacttgcma tgtttaatga ttgtcanccm nanaantaag    120
ctnacagggc aaaaacagcc tyangtcagt tctntctccc taatcctcta graknaaatc    180
nnawrntrnn actctgnntc tgtgccatna nanatnttnc anttgtattt atgnactcca    240
catngagtac acctcactaa wtntnctnct gggnaacncc cscmccantt tttnnttgnt    300
gananacarc aatgctggca tacngtg                                        327

<210> SEQ ID NO 40
<211> LENGTH: 431
<212> TYPE: DNA
<213> ORGANISM: Homo sapiens
<220> FEATURE:
<221> NAME/KEY: misc_feature
<222> LOCATION: (1)..(431)
<223> OTHER INFORMATION: where n may be either a or g or c or t/u,
      unknown or other

<400> SEQUENCE: 40
ccagactttc ataactngtg ttattatgaa gattagagtn ctgaagctta ctggattaga     60
agagnacgag ggggtagctg ccccaatata ttctaatttc tctkgaggac caccaaatng   120
gmagagtgtc tctgataggg aaaaggaaga gttggaaggn atcttagcct ctagganaaa   180
agaaccattt ttattggcca ccaaagttac atctagtkgc ctacaaattt atntccaaac   240
tccttatcct gccaattcag ggtcctgnaa actgatgcca aactatagtt tagtctncta   300
tcacatgact gcattataca tacccaatta tctgggmaaa cagacctgat ccaaacacag   360
ttkggtnctt tccttnccrt nccttkgttt agcctgtycc gtctactngg ggtgtcttkg   420
atttgctcca g                                                         431

<210> SEQ ID NO 41
<211> LENGTH: 276
<212> TYPE: DNA
<213> ORGANISM: Homo sapiens
<220> FEATURE:
<221> NAME/KEY: misc_feature
<222> LOCATION: (1)..(276)
<223> OTHER INFORMATION: where n may be either a or g or c or t/u,
      unknown or other

<400> SEQUENCE: 41
tttttttcca ccagacttac caaattttag atgnatggaa gaactgtaaa tncccataaa     60
gntaatctat ncatngaccc ccaccattat gatagagatc atntggtgan taatgaaaga   120
tgaaactctc agctgggaaa gtaanaagga ataggatgta agtatgagct cctgtttttt   180
attatnttta tggatgcccc ctcagaaaaa tatgnaaagg ggtaactgac tnggaaatgg   240
gtnttttatg natagtaagt cccactcacg aggttt                              276

<210> SEQ ID NO 42
<211> LENGTH: 270
<212> TYPE: DNA
<213> ORGANISM: Homo sapiens
<220> FEATURE:
<221> NAME/KEY: misc_feature
<222> LOCATION: (1)..(270)
<223> OTHER INFORMATION: where n may be either a or g or c or t/u,
      unknown or other

<400> SEQUENCE: 42
tcgagatcta aagcagatgn agactttnca cnaaataaat ttactgcttt tttyctgtga     60
```

```
nataagttnc gagaaggaaa gctttkgatt nctrnatgag tycagtggat tatyctnagn      120
actagagtkg nkgtkgaagn catggnacat ttatatagwt ywttcagttc tacactaaat      180
gatggaagaa tgagaaatcc tatatgcaaa atagaaaagt ycatyctyca taattgagaa      240
cattgagcag ttggattacc aagatctcga                                       270
```

<210> SEQ ID NO 43
<211> LENGTH: 580
<212> TYPE: DNA
<213> ORGANISM: Homo sapiens
<220> FEATURE:
<221> NAME/KEY: misc_feature
<222> LOCATION: (1)..(580)
<223> OTHER INFORMATION: where n may be either a or g or c or t/u,
      unknown or other

<400> SEQUENCE: 43

```
cttagtttta gactagtttc attatactac cagtttctaa tatgttggtt ttttattcac       60
tatttgatat atttgtttta atatatgttc ttgttttagc aggtaaaaga atcataacaa      120
atgtttttaa aagaacatta ttattcttta ataactgtct ttttatgcat ttggcatgcc      180 aactttttc attaacatct tgggtatttt ataaaaagag ggaaagctca atgtttaaca       240
ggtagctttt cttaggagct aaattaaata tttaacaaat ctccttccct tcncccttcc      300
ccatccctca aagnatgggt gnanttatct ttaactttg ggctngcatc cntgnaagct       360
tatggntant catagtctna cmaaactagg gtcaccnaac ttggcagcag aaataatcta      420
gtcttactgt gataactacc caattacttt attattttc cagttncagt tccaaatgtt      480
ttgtggnaan aatttttnct gtttgtgatt ttccaagctt agaggggaa accaactttc      540 cagtgttgga gagcactgna tagtttatgn attgtgtaaa                            580
```

<210> SEQ ID NO 44
<211> LENGTH: 348
<212> TYPE: DNA
<213> ORGANISM: Homo sapiens
<220> FEATURE:
<221> NAME/KEY: misc_feature
<222> LOCATION: (1)..(347)
<223> OTHER INFORMATION: where n may be either a or g or c or t/u,
      unknown or other

<400> SEQUENCE: 44

```
tgtttcttaa nacagaaaaa aatttactga tnggacattg ttctaagtgt attattgtat       60
taaatggatc atttaattta atcttcataa ctgacatagg agttgagtaa cttgtgtggt      120
caaatagcta gtaagtgatg agtaggctgg gcgcagtggc tcaagcctgt aatcccagca      180
ctctgggagg ctgaggcagg cagatcactt gaggtcagga gtttgagacc agcctggnca      240
acatggnaaa acctcgtctc tactaaaaat acaaaaatta gctgggcgtg gtgggngcgc      300
acttgtagnc ccagntactc ggaaggctng aggcaggagg aatcgctt                   348
```

<210> SEQ ID NO 45
<211> LENGTH: 430
<212> TYPE: DNA
<213> ORGANISM: Homo sapiens
<220> FEATURE:
<221> NAME/KEY: misc_feature
<222> LOCATION: (1)..(430)
<223> OTHER INFORMATION: where n may be either a or g or c or t/u,
      unknown or other

<400> SEQUENCE: 45

```
gctcatcatg cttcacgggg gaggctgtgc gggaagaatg ctcccacaca gnataaagaa      60
tgctcccgca caggatagag aatgcccccg cacagcatag agaagccccc gcacagcata     120
gagaatgccc ccncacagca tagagaagcc cccgcacagn atagagaatg ctcttcacct     180
ctgggttttt aaccagccaa actaaaatca cagagggcaa cacatcattt aagatagaaa     240
tttctgtatc ttttaatttc tttcaaagta gttttactta tttncagatt ctatttcttt     300
actagaatta agggataaaa taacaatgtg tgcataatga accctatgaa acaaacaaaa     360
gctaggtttt ntncataggt ctncttccnn attgaatgaa cgtctntcct caaatttanc     420
cccccaggga                                                            430

<210> SEQ ID NO 46
<211> LENGTH: 402
<212> TYPE: DNA
<213> ORGANISM: Homo sapiens
<220> FEATURE:
<221> NAME/KEY: misc_feature
<222> LOCATION: (1)..(400)
<223> OTHER INFORMATION: where n may be either a or g or c or t/u,
      unknown or other

<400> SEQUENCE: 46
caaaccctat gngaaatgga aaggaaacta ttctaaagca taaaaggtag aaatatatat      60
accacccatc aagaaagatt atttttgntg aactcaagtc accagagtgg ctaaagccca     120
gtagaatgga aatgattata tggaaggtga ggccaacggg accagaacat actgtgatag     180
acagnaagga gctgtctatc ttctattctc ccacagaagg aggtgactaa gtcanctgcc     240
caagcaatgt tatatctgca attgatgtnc agcagtacaa gtctgaacaa cttggattgg     300
ntgattaant gtccnacant aaacatacaa gtcntaatag ctatctctat atagtctttg     360
ggtntttaca aggcactgnc acatnatctc acctattcct cc                        402

<210> SEQ ID NO 47
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 47
agnatccaga attgagtgna gngttctctg gnccacagtc tcggtatctn ctgtgaaatg      60
gggtatagat tctacaataa aacaaacaca nnggccctag gtcagtgtta atggagatca     120
ccanccacat taccacctcc aacacagaat tttcttttc ttaatncaat ncgtntctta      180
taagtcactt tnccccaact caccaatcta gntaagaatt tttaccctga gaaaacagc     240 tacactctaa aattgctnca aagaaaatgt ctaacatntg gaaagaagga cttaacatgt     300
gangnagaca ctggctccat ctagngggtg ctttnttttg aaataattat aatnccncat     360
caaattttng ggggntacag cttattagga acttgttata gaaccagatt ctgccacaga     420
anccacgtgg gttgacaagt ggttgncaga agaaaggtaa tatggcttat nattagggnc     480
tcncatctgc agagtaattg                                                 500

<210> SEQ ID NO 48
<211> LENGTH: 460
<212> TYPE: DNA
<213> ORGANISM: Homo sapiens
```

```
<220> FEATURE:
<221> NAME/KEY: misc_feature
<222> LOCATION: (1)..(460)
<223> OTHER INFORMATION: where n may be either a or g or c or t/u,
      unknown or other

<400> SEQUENCE: 48
aaaatgcttg anncaaatgt catctagttc catctctacg actctcatgg ggtccaaaga       60
agagttttan ttgagtttta gaatgtgaag ttgtgaagtg tctgaaaaac tacatggtgn      120
tctgaaagnc aaacttttag ccttggggga gagcatctaa gacagnaggt gaagggnagg      180
ggttagaact agagggattg aagaatatta tccatatagg ttagggttag gtnnggcaac      240
gttttataga acaaacattg gcaagctaca gccacaggcc agatctgtct nctaccttcc      300
cacaaaggtg taataacaaa gttattcaca aatgtgtgaa taaactnnca ttggaaagtg      360
cccacgctcc tnggtttata cattgtctgt ggctgctttc acactacagt agcacaggtg      420
agtgtntgca ctggagacca tatgccccat agagctttaa                            460

<210> SEQ ID NO 49
<211> LENGTH: 372
<212> TYPE: DNA
<213> ORGANISM: Homo sapiens
<220> FEATURE:
<221> NAME/KEY: misc_feature
<222> LOCATION: (1)..(370)
<223> OTHER INFORMATION: where n may be either a or g or c or t/u,
      unknown or other

<400> SEQUENCE: 49
atcaagcaac agtgtgttat gcctatactc catgtttata tgtgtgtatt aaaaaatgta       60
tttngtatat atgtgtatgt ataagtgtgt gtgtgtgtat gatgattctn ctcccgnttt      120
gaaggtgaaa gaaagcacac ctttatttaa gcataaactt tgggtttcan gatactgtct      180
ggaaaaatga tttatctccc actttgaaat tccaaaatac gtacatatat ttttttttc       240 ttttcttttt tagtttnagg gtcttgctgt gttgcccagg ctggagtgca gtagtgtgat      300
catagntcac acagnctcta actcccaggn tcaagntatc ttcctgcccc agnctcctga      360
gtagntggga ct                                                          372

<210> SEQ ID NO 50
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 50
caaaaaatca aagggaagnt ggaacccctg cccacctctc cattccccat tctgctggtg       60
gtgnctgctc ttcctcacag tacctcctga aaagttcaga attcagttaa tacagaatta      120
ttgggttgat tttcaacgtg tagtttaaga tgaagagttc cgnttggttt aaaccacttc      180
acctaacctc ttggtaacgg tagtcctgag agttcgcagt gtcantgaaa atcgtcctgt      240
gaccacgcgt caagctgctg atggggggaca gaaacttccg ggnctatcat atctccttga      300
nctcggccct caaatctggt agtttctgca ccgagggaca cagtccactg cgatgaagta      360
tgttcaaaat cgnttctttt agggaactcc ttccaaagtc caatagtgna aggtggtcaa      420
ggaaggattt ggaaggaagn tgnaaaagtc agncgggaat cttgatttgg ntagntgtgg      480
```
ananaggaaa tcacttggcc                                                500

<210> SEQ ID NO 51
<211> LENGTH: 105
<212> TYPE: DNA
<213> ORGANISM: Homo sapiens
<220> FEATURE:
<221> NAME/KEY: misc_feature
<222> LOCATION: (1)..(105)
<223> OTHER INFORMATION: where n may be either a or g or c or t/u,
      unknown or other

<400> SEQUENCE: 51
ggaaagaggt ctcctaacac ccagacagtg taaaaatcca gttttcttc cttttggnng      60 gagacagagt ctcgcactgt agctcaggct ggagtgcagt ggcac                   105

<210> SEQ ID NO 52
<211> LENGTH: 387
<212> TYPE: DNA
<213> ORGANISM: Homo sapiens
<220> FEATURE:
<221> NAME/KEY: misc_feature
<222> LOCATION: (1)..(387)
<223> OTHER INFORMATION: where n may be either a or g or c or t/u,
      unknown or other

<400> SEQUENCE: 52
agtcccagct actcaggagg ctggggcagg aagatagctt gagcctggga gttagaggct     60
gtgtgagcta tgatcacact actgcactcc agcctgggca acacagcaag accctaaaac   120 taaaaagaa aagaaaaaaa aaatatatgt acgtattttg gaatttcaaa gtgggagata   180
aatcattttt ccagacagta tctngaaacc caaagtttat gcttaaataa aggtgtgctt   240
tctttcacct tcaaagcggg agaagaatca tcatacacac acacacactt atacatacac   300
atatatacaa aatacatttt ttaatacaca catataaaca tggagtatag gcataacaca   360
ctgttgcttg ataaaatata gggatcc                                       387

<210> SEQ ID NO 53
<211> LENGTH: 380
<212> TYPE: DNA
<213> ORGANISM: Homo sapiens
<220> FEATURE:
<221> NAME/KEY: misc_feature
<222> LOCATION: (1)..(377)
<223> OTHER INFORMATION: where n may be either a or g or c or t/u,
      unknown or other

<400> SEQUENCE: 53
tatatttnat caagcaacag tgtgttatgc ctatactcca tgtttatatg tgtgtattaa     60
aaaatgtant ttgtatatat gtgtatgtat aagtgtgtgt gtgtgtatga tgattctcct   120
cccgnnttga aggtgaaaga aagcacacct ttatttaagc ataaactttg ggtttcnaga   180
tactgtctgg aaaaatgatt tatctcccac tttgaaattc caaaatacgt acatatattt   240
tttttttctt ttcttttta gtttnagggt cttgctgtgt tgcccaggct ggagtgcagt   300
agtgtgatca tagntcacac aggctctaac tcccaggntc aagctatctt cctgccccag   360
nctcctgagt aggtgggact                                              380

<210> SEQ ID NO 54
<211> LENGTH: 521
<212> TYPE: DNA
<213> ORGANISM: Homo sapiens

```
<220> FEATURE:
<221> NAME/KEY: misc_feature
<222> LOCATION: (1)..(521)
<223> OTHER INFORMATION: where n may be either a or g or c or t/u,
      unknown or other

<400> SEQUENCE: 54
ctgcagtaag ccacgttcat gccactgtac tctagcgtgg atgacagaga gagatcctgt    60 cttttggaaga aaaaaacaaa aagaaaaaaa aaagagtatg ccatggcct tataatatag   120 aaggggtcac atattaatct ctgaaaatgg atctcttgtg ggctttcata caaggcaaca   180
gccacagagt acgtacctga aagctgcctg ggnttaatgg ctggnagtat gttctaactn   240
gttcaggnac ccatgtcacn actggtggtt acagaatgtg aatctcacac tgtccnaaat   300
cggttttatt tttaaaanga ataattctan tacattacct tataaaaagt aggtaaccta   360
attttggntt ttaaaagtga attgagggca gatgcaagtg gntcacacct attaatccca   420
aataccttgg agagggcaag gtaggaggat tggttgagc ccaggagtcc aaagaccagg    480
ctagggaata ttgnaagaan gtcctctcta caanaaanaa t                       521

<210> SEQ ID NO 55
<211> LENGTH: 516
<212> TYPE: DNA
<213> ORGANISM: Homo sapiens
<220> FEATURE:
<221> NAME/KEY: misc_feature
<222> LOCATION: (1)..(516)
<223> OTHER INFORMATION: where n may be either a or g or c or t/u,
      unknown or other

<400> SEQUENCE: 55
ctgcangaag cttttnttnc ttttnggngg agacagagtc ttgctgtgtc ancccaggct    60
ggggtgcagt ggnacagtca tagctcactg caaccttgaa ctccctggnt catgcgatcc   120
tcccacttca gcctctcaag tagctagaac tacaggtgtg caccaccatg cctgactaac   180
ttgtttattn gngggagaga gaacgntctt gctatattgc ctaggctggt cnttgaactc   240
ttgggntnca agcaatcctc ctaccttggc ctctncaagg tanttgggat tnataggtgt   300
gagccacntg catctggcct caattcactt ttaaaatnca aaattaggtt acctactttt   360
tataaggtaa tgtattagaa ttattcttnn naaaaataaa accgatttgg gaaagngtga   420
gantcacatt ctgtaaccac cagtggtgaa atgggtcccc gaacaaggta gaacatactc   480
ccagccatta accccaggga gngttcaagt ccgtnc                             516

<210> SEQ ID NO 56
<211> LENGTH: 505
<212> TYPE: DNA
<213> ORGANISM: Homo sapiens
<220> FEATURE:
<221> NAME/KEY: misc_feature
<222> LOCATION: (1)..(505)
<223> OTHER INFORMATION: where n may be either a or g or c or t/u,
      unknown or other

<400> SEQUENCE: 56
ggatcctgtt tcttaaaaca gaaaaaaatt tactgatagn acattgttct aagtgtatta    60
ttgtattaaa tggatcattt aatttaatct tcataactga cataggagtt gagtaacttg   120
tgtggtcaaa tagctagtaa gtgatgagta ggctgggcgc agtggntcaa gcctgtaatc   180
ccagcactct gggaggctga ggcaggcaga tcacttgagg tcaggagttt gagaccagcc   240
tggccaacat ggnaaaacct cgtctctact aaaaatacaa aaattagctg ggcgtggtgg   300
```

```
gtgcgcactt gtagtcccag ctactcggaa gggttgaggc aggaggaatc gcttggtccc      360
cgggagggag aggttgntng tgnagctgag atcacgccac tngcactcca ggctgggnaa      420
caaaagggag acctttnctc aaaaaaaaat naaaataaaa agtgatgagt aggattggga      480
cccnagacat cttttctcca agacc                                           505

<210> SEQ ID NO 57
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 57
ctgcagnctc aaaccttgt cctgggatca acaatcctc ccacctcagc cttcaaagta        60
gatagaacta caggcatgca ctaccatgcc taatttttta aaaaaaatt ttttttcaga      120 gatgagatct cactgtgttt cccaggnttg tccggaactc ctggactcaa gcgatcctcc     180
caccttgggc tgccaaagtg ttgggattac aggcatgagc caccatgcct ggccatacac     240
tttttttttt tttttaanca agacggagtc tngttctgtc gcccagactg gagtgcaggg     300
gcgtnnatct tggctcactt gaaagcttcg cctcccaggg ttcatgccgt tctcctgnct     360
cagcctccca agtnggtggg actacaggna tctgcaccac gnccggttat ttnttgggtt     420
tgnngnaggg acgggggttc accatgttag gcaggatgac ttcggacttc cngacccaag     480
atcaccctgc tcggctccca                                                 500

<210> SEQ ID NO 58
<211> LENGTH: 440
<212> TYPE: DNA
<213> ORGANISM: Homo sapiens
<220> FEATURE:
<221> NAME/KEY: misc_feature
<222> LOCATION: (1)..(440)
<223> OTHER INFORMATION: where n may be either a or g or c or t/u,
      unknown or other

<400> SEQUENCE: 58
gaattccaga cgagcctggg caacacagtg agactctatc actacaaaaa aattttaaaa      60
ttagctaaag ttgatggnac atgcctgcag tcccagctac tcaggaggct ggggcaggaa     120
gatagcttga gcctgggagt tagaggctgt gtgagctatg atcacactac tgcactccag     180
cctgggcaac acagcaagac cctaaaacta aaaagaaaa gaaaaaaaaa atatatgtac      240
gtntttgggg aatttcaaag tgggagataa atcattttc cagacagtnt cttgaaaccc      300
aaagtttatg cttaaataaa ggtgtgcttt ctttcacctt caaangcggg agaaggatca     360
tcatncacac acacacactn atcatncaca tttttacaaa tncaattnnn naatacaaca     420
cattttaaca tggggttttg                                                 440

<210> SEQ ID NO 59
<211> LENGTH: 513
<212> TYPE: DNA
<213> ORGANISM: Homo sapiens
<220> FEATURE:
<221> NAME/KEY: misc_feature
<222> LOCATION: (1)..(513)
<223> OTHER INFORMATION: where n may be either a or g or c or t/u,
      unknown or other
```

<400> SEQUENCE: 59

```
ggatcctgtt tcttaaaaca gaaaaaaatt tactgatagn acattgttct aagtgtatta      60
ttgtattaaa tggatcattt aatttaatct tcataactga cataggagtt gagtaacttg     120
tgtggtcaaa tagctagtaa gtgatgagta ggctgggcgc agtggctcaa gcctgtaatc    180
ccagcactct gggaggctga ggcaggcaga tcacttgagg tcaggagttt gagaccagcc    240
tggccaacat ggnaaaacct cgtctctact aaaaatacaa aaattagctg gcgtggtgg      300
ntgcgcactt gtagtcccag ctactcggaa ggctngaggc aggaggaatc gcttgatccc    360
ngggagggag aggttggtng tgangctgag atcacgncac ttgnactcca gnctgggnaa    420
caaangngag atcttntctc aaaaaaaaat aaaantaaaa ngtgatgagt aggatttgga    480
ccccagacat cctntctcca ggacctggna ttc                                 513
```

<210> SEQ ID NO 60
<211> LENGTH: 390
<212> TYPE: DNA
<213> ORGANISM: Homo sapiens
<220> FEATURE:
<221> NAME/KEY: misc_feature
<222> LOCATION: (1)..(390)
<223> OTHER INFORMATION: where n may be either a or g or c or t/u,
      unknown or other

<400> SEQUENCE: 60

```
gaattcctgg nctcaagtga tcctctcacc tcagcctccc aaattgctgg gattagagtg      60
tgagccactg tgcctagcct gcatatatct atttttaatg actgctaaat ctcattgtat    120
gaaaatttat gtcctagcta taaaatttgn tagcacatgt ttaattttt ctaatttcag     180
atgttttaaa ctaatatttc ccaaagtata gtatggcatt ttaggtatga tatgatcttt    240
nntcctcttc gtactcattt ttatagttat ggcctgtgca actggtttcc catttatatg    300
aatgatacag agcttcctat taagaaaaag ttcagcttgg ggaaaaaaa agtgaattgt     360
caacttngag ggaaaaaagt gaattattgg                                     390
```

<210> SEQ ID NO 61
<211> LENGTH: 366
<212> TYPE: DNA
<213> ORGANISM: Homo sapiens
<220> FEATURE:
<221> NAME/KEY: misc_feature
<222> LOCATION: (1)..(366)
<223> OTHER INFORMATION: where n may be either a or g or c or t/u,
      unknown or other

<400> SEQUENCE: 61

```
tcaagtacct ccctgaatgg actgcgtggc tcatcttggc tgtgatttca gtatatggta      60
aaacccaaga ctgataattt gtttgtcaca ggaatgcccc actggagtgt tttctttcct    120
catctcttta tcttgattta gagaaaatgg taacgtgtac atcccataac tcttcagtaa    180
atcattaatt agctatagta acttttttcat ttgaagattt cggctgggca tggtagctca    240
tgcctgtaat cttagcactt tgggaggctg aggcgggcag atcacctaag cccagagttc    300
aagaccagcc tgggcaacat ggcaaaacct cgtatctaca gaaaatacaa aaattngncg    360
ggnatg                                                               366
```

<210> SEQ ID NO 62
<211> LENGTH: 498
<212> TYPE: DNA

<213> ORGANISM: Homo sapiens
<220> FEATURE:
<221> NAME/KEY: misc_feature
<222> LOCATION: (1)..(498)
<223> OTHER INFORMATION: where n may be either a or g or c or t/u,
      unknown or other

<400> SEQUENCE: 62

```
aacaccaggg ncatgagggc actaatcata atgagatatg cctgctggag tcgaagtgga      60
ccttttccagt gaatggaaat cattcccacc acaccaaaat tccagatcag gagtgnaaca   120
gtaatgtagt ccacagcaac gttataggtt ttaaacactt ccctgaaaaa aaattacaca   180
gattttaaaa gatgtacaat aatttccacc aaaacattat ttagaataat gtgatggctc   240
ccaaacatta gatattaatn tcccaccttt ataattttac cataacctat atcaactgtg   300
ctattattta tttaatnctt ccctntaaat taatttactc tttttttgtt tttgttttg    360
ngtttggagc cagtgtctca ttttggttgc ccaggcttgg agtaaagtgg gtgcaatcac   420
ggctcaactg nagtctttnc ctccnggaga tcaggtnggt cttccccagg tccaanctcc   480
taagttggtt ngganaac                                                 498
```

<210> SEQ ID NO 63
<211> LENGTH: 469
<212> TYPE: DNA
<213> ORGANISM: Homo sapiens
<220> FEATURE:
<221> NAME/KEY: misc_feature
<222> LOCATION: (1)..(469)
<223> OTHER INFORMATION: where n may be either a or g or c or t/u,
      unknown or other

<400> SEQUENCE: 63

```
taaacaacag ggncatgagg gcactaatca taatgagata tgcctgctgg agtcgaagtg     60
gaccttttcca gtgaatggaa atcattccca ccacaccaaa attccagatc aggagtgaaa   120
cagtaatgta gtccacagca acgttatagg ttttaaacac ttccctgaaa aaaaattaca   180
cagattttaa aagatgtaca ataatttcca ccaaaacatt atttagaata atgtgatggc   240
tcccaaacat tagatattaa tntcccacct ttataatttt accataacct atatcaactg   300
tgctattatt tatttaatnc ttccctctaa attaatttac tcttttttg ttttgtttt    360
tgtgttttgga gccagtgtct cattttggtt gcccaggctt ggagtaaagt gggtgcaatc   420
acggctcaac tgnagtcttt acctcccgga gatcangttg gtctttccc                469
```

<210> SEQ ID NO 64
<211> LENGTH: 370
<212> TYPE: DNA
<213> ORGANISM: Homo sapiens
<220> FEATURE:
<221> NAME/KEY: misc_feature
<222> LOCATION: (1)..(370)
<223> OTHER INFORMATION: where n may be either a or g or c or t/u,
      unknown or other

<400> SEQUENCE: 64

```
gtttatcaag tacctccctg aatggactgn gtggctcatc ttggctgtga tttcagtata     60
tggtaaaacc caagactgat aatttgtttg tcacaggaat gccccactgg agtgttttct   120
ttcctcatct ctttatcttg atttagagaa aatggtaacg tgtacatccc ataactcttc   180
agtaaatcat taattagcta tagtaacttt tcatttgaa gatttcggct gggcatggta    240
gctcatgcct gtaatcttag cactttggga ggctgaggcg ggcagatcac ctaagcccag   300
```

```
agttcaagac cagcctgggc aacatggcaa aacctcgtat ctacagaaaa tacaaaaatt    360 agccnggnat                                                           370
```

<210> SEQ ID NO 65
<211> LENGTH: 316
<212> TYPE: DNA
<213> ORGANISM: Homo sapiens
<220> FEATURE:
<221> NAME/KEY: misc_feature
<222> LOCATION: (1)..(316)
<223> OTHER INFORMATION: where n may be either a or g or c or t/u,
      unknown or other

<400> SEQUENCE: 65

```
gtcatggtgt tggcggggag tgtcttttag catgctaatg tattataatt agcgtatagt     60
gagcagtgag gataaccaga ggtcactctc ctcaccatct tggttttggt gggttttggc    120
cagcttcttt attgcaacca gttttatcag caagatcttt atgagctgta tcttgtgctg    180
acttcctatc tcatcccgna actaagagta cctaacctcc tgnaaattga agnccagnag    240
gtcttggcct tatttnaccc agcccctatt caaaatagag tngttcttgg nccaaacgcc    300
cctgacacaa ggattt                                                   316
```

<210> SEQ ID NO 66
<211> LENGTH: 448
<212> TYPE: DNA
<213> ORGANISM: Homo sapiens
<220> FEATURE:
<221> NAME/KEY: misc_feature
<222> LOCATION: (1)..(448)
<223> OTHER INFORMATION: where n may be either a or g or c or t/u,
      unknown or other

<400> SEQUENCE: 66

```
ctgcagnccg ggggatcctg gtaaaagtca caaggtcagc ctactaaagc agggaaaact     60
aaaggcaagt aaacacgtgc agacaaaaaa agggataaag aaaaggaatt aagaaactag    120 cattttttaan gtgggggagg tgaatgcttc ccagaatggg tttatatcac ttgcttgngg    180
gccttctgag tgttggnaac aacctgtcat catcacacat acctgtcatc tttaatggtc    240
tccatacatt actaatagat tatacagatg gccatcactt aacacttcca ctcactcaat    300
ttgtncaaca tgcaaggtta ccctcttttt tngcttacng ccacaaagca ttgganaagg    360
tttgtgattt ttactagccn ccacttcatc aaatttaagc attttctttt tcctnttaac    420
anccaggaca ggnttnaacn aaggaaat                                      448
```

<210> SEQ ID NO 67
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: where n may be either a or g or c or t/u,
      unknown or other

<400> SEQUENCE: 67

```
ctgcagctcc aagcaccttt ttcaaattca gctttctgtg atttcagacc acatatgcaa     60
ggaactatct taccttaatt aataagactt taaaatcctt gtgtcagagg cgtttggacc    120
agagcaactc tatcttgaat aggggctggg taaaataagg ccaagaccta ctgggctgca    180
tttgcaggag gttaggtact cttagttacg ggatgagata ggaagtcagc acaagataca    240
```

-continued

| | |
|---|---|
| gctcataaag gatcttgctg ataaaactgg ttgcaataaa gaagctggnc aaaacccacc | 300 |
| aaaaccaaga tggtgaggag agtgacctct ggttatcctc actgntcact atacgntaat | 360 |
| tattatacat tagcatgcta aaagacactc cccgcaacaa ccatganagg tttacaagtt | 420 |
| nccatggnaa cgnncccgga ngntancttg | 450 |

<210> SEQ ID NO 68
<211> LENGTH: 388
<212> TYPE: DNA
<213> ORGANISM: Homo sapiens
<220> FEATURE:
<221> NAME/KEY: misc_feature
<222> LOCATION: (1)..(388)
<223> OTHER INFORMATION: where n may be either a or g or c or t/u,
    unknown or other

<400> SEQUENCE: 68

| | |
|---|---|
| ctgnagcctc caccacccag gttcaggtga ttctcctgcc gtagnctcat gagtagntgg | 60 |
| gattacaggc atgtgccacc atgcccgact aattttata tttttagtag agacggggtt | 120 |
| tcaccatgtt gggcaggctg gtctcaaact cctgacctca agtgatctgc ccaccttggc | 180 |
| ctcccaaagt gctgggattt caggcgcctg gcctgttact tgattatatg ctaaacaagg | 240 |
| ggtggattat tcatgagttt tctgggaaag aggtgggcaa ttcccggaac tgagggatcc | 300 |
| ctcccccttnn nagaccatac aaggtaactt ccggacgttg gcatggnatc ttgttaaact | 360 |
| tgtcatggng ttgggggga gtgtctttt | 388 |

<210> SEQ ID NO 69
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
    unknown or other

<400> SEQUENCE: 69

| | |
|---|---|
| ctgcagaagt atgtttcctg tatggtatta ctggataggg ctgaagttat gctgaattga | 60 |
| acacataaat tcttttccac ctcagggnca ttgggcgccc attgctcttc tgcctagaat | 120 |
| attctttcct tttctaactt tggtggatta aattcctgtc atcccctcc tcttggtgtt | 180 |
| atatataaag tnttggtgcc gcaaaagaag tagcactcga atataaaatt ttccttttaa | 240 |
| ttctcagcaa ggnaagttac ttctatatag aagggtgcac ccntacagat ggaacaatgg | 300 |
| caagcgcaca tttgggacaa gggaggggaa agggttctta tccctgacac acgtggtccc | 360 |
| ngctgntgtg tnctncccc actgantagg gttagactgg acaggcttaa actaattcca | 420 |
| attggntaat ttaaagagaa tnatggggtg aatgctttgg gaggagtcaa ggaagagnag | 480 |
| gtagnaggta acttgaatga | 500 |

<210> SEQ ID NO 70
<211> LENGTH: 435
<212> TYPE: DNA
<213> ORGANISM: Homo sapiens
<220> FEATURE:
<221> NAME/KEY: misc_feature
<222> LOCATION: (1)..(435)
<223> OTHER INFORMATION: where n may be either a or g or c or t/u,
    unknown or other

<400> SEQUENCE: 70

```
ctgcagagta attgcaactg gagttgtctt aagataatgt cacatatcca tcttcccctt      60
gtttctcatt cacagaaaaa catttttatt ccaggtgcca atattcccag ccaaaaagac     120
tttacttctg actcccttat atttaggatg gctatgagaa caagtaaggg caatgacttc     180
tagggagatg tgttgtgtat ggaacttcta aggagagaat tctgctgaca tgtcctatgt     240
tcttttctcc cctactcctt cctactgtca gaaatgaagg ctagggctcc agcctggacc     300
ctgaagtaag ctagaggtta gaagctaaag aagaaagaag gagattgagt ccttggatga     360
acgtgaagcc accctactaa tctggactgn ctacctctgn actactctat gagagagaaa     420
gtatgtgcat tattt                                                     435

<210> SEQ ID NO 71
<211> LENGTH: 439
<212> TYPE: DNA
<213> ORGANISM: Homo sapiens
<220> FEATURE:
<221> NAME/KEY: misc_feature
<222> LOCATION: (1)..(439)
<223> OTHER INFORMATION: where n may be either a or g or c or t/u,
      unknown or other

<400> SEQUENCE: 71
catgctcttt gtccctgtga ctctctgcat ggtggtggtc gtggntacca ttaagtcagt      60
cagcttttat acccggaagg atgggcagct gtacgtatga gtttggtttt attattctca     120
aagccagtgt ggcttttctt tacagcatgt catcatcacc ttgaaggcct ctgcattgaa     180
ggggcatgac ttagctggag agcccatcct ctgtgatggt caggagcagt tgagagagcg     240
aggggttatt acttcatgtt ttaagtggag aaaaggaaca ctgcagaagt atgtttcctg     300
tatggtatta ctggataggg ctgaagttat gctgaattga acacataaat tcttttccac     360
ctcaggggca ttgggcgccc attgntcttc tgcctagaat attctttcct ttnctnactt     420
gggnggatta aattcctgt                                                 439

<210> SEQ ID NO 72
<211> LENGTH: 318
<212> TYPE: DNA
<213> ORGANISM: Homo sapiens
<220> FEATURE:
<221> NAME/KEY: misc_feature
<222> LOCATION: (1)..(318)
<223> OTHER INFORMATION: where n may be either a or g or c or t/u,
      unknown or other

<400> SEQUENCE: 72
tccatctcta cgactctcat ggggtccaaa gaagagtttt aattgagttt tagaatgtgn      60
agttgtgaag tgtctgaaaa actacatggt gntctgaaag ncaaacttt agccttgggg     120 gagagcatct aagacagnag gtgaagggga ggggttagan ctagagggat tgaagaatat     180
tatccatata ggttagggtt aggtgtggca acgttttata gaacaaacat tggnaagcta     240
cagacacagg ccagntctgt ctnctacctn tccacaaagg tgtnataaca aagttannca     300
caaatgtgtg aataaact                                                  318

<210> SEQ ID NO 73
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: where n may be either a or g or c or t/u,
``` unknown or other

<400> SEQUENCE: 73

```
gttgcaaagt catggattcc tttaggtagc tacattatca acctttttga gaataaaatg    60
aattgagagt gttacagtct aattctatat cacatgtaac ttttatttgg atatatcagt   120
aatagtgctt tttcnttttt tttttttntt tttttnntt ttnggggana gagtctcgct   180
ctgtcgccag gttggagtgc aatggtgcga tcttggctca ctgaaagctc caccncccgg   240
gttcaagtga ttctcctgcc tcagccnccc aagtagntgg gactacaggg gtgcgccacc   300
acgcctggga taattttggg nttttagta gagatggcgt ttcaccanct tggngcaggc   360
tggtcttgga actcctgana tcatgatctg cctgccttag cctccccaaa gtgctgggat   420
tncagggtg agccactgtt cctgggcctc                                     450
```

<210> SEQ ID NO 74
<211> LENGTH: 489
<212> TYPE: DNA
<213> ORGANISM: Homo sapiens
<220> FEATURE:
<221> NAME/KEY: misc_feature
<222> LOCATION: (1)..(489)
<223> OTHER INFORMATION: where n may be either a or g or c or t/u,
      unknown or other

<400> SEQUENCE: 74

```
ctgcagntga gccgtgattg canccactttt actccnagcc tgggcaanca aaatgagaca    60
ctggctncaa acacaaaaac aaaaacaaaa aaagagtaaa ttaatttaaa gggaagtatt   120
aaataaataa tagcacagtt gatataggtt atggtaaaat tataaaggtg ggatattaat   180
atctaatgtt tgggagccat cacattattc taaataatgt tttggtggaa attattgtac   240
atcttttaaa atctgtgtaa ttttttttca gggaagtgtt taaaacctat aacgttgctg   300
tggactacat tactgttgca ctcctgatct ggaattttgg tgtggtggga atgatttcca   360
ttcactggaa aggtccactt cgactccagc aggcatatct cattatgatt agtgccctca   420
tggccctggt gtttatcaag taccncccctg aatggactgg gtggctcatc ttggctgtga   480
tttcagtat                                                           489
```

<210> SEQ ID NO 75
<211> LENGTH: 449
<212> TYPE: DNA
<213> ORGANISM: Homo sapiens
<220> FEATURE:
<221> NAME/KEY: misc_feature
<222> LOCATION: (1)..(449)
<223> OTHER INFORMATION: where n may be either a or g or c or t/u,
      unknown or other

<400> SEQUENCE: 75

```
ctgcagnctt gacctcctgg gatcaatcga tcctcccacc tcagcctcct aagtagctgg    60
aactacaggt gtgcaccacc atgcccggct aattttttgta ttttctgtag atacgaggtt   120
ttgccatgtt gcccaggctg gtcttgaact ctgggcttag gtgatctgcc cgcctcagcc   180
tcccaaagtg ctaagattac aggcatgagc taccatgccc agccgaaatc ttcaaatgaa   240
aaagttacta tagctaatta atgatttact gaagagttat gggatgtaca cgttaccatt   300
ttctctaaat caagataaag agatgaggaa agaaaacact ccagtggggc attcctgtga   360
caaacaaatt atcagtcttg ggttttacna tatactgaaa tcacagccaa gatgagccac   420
gcagtccatt cagggaggta cttgataaa                                     449
```

<210> SEQ ID NO 76
<211> LENGTH: 490
<212> TYPE: DNA
<213> ORGANISM: Homo sapiens
<220> FEATURE:
<221> NAME/KEY: misc_feature
<222> LOCATION: (1)..(490)
<223> OTHER INFORMATION: where n may be either a or g or c or t/u,
      unknown or other

<400> SEQUENCE: 76

| | | | | | |
|---|---|---|---|---|---|
| ttcttgccgt | tcccgacccg | agcctggtgc | cccttcccca | ttatgatcct | tntcgcttcc | 60 |
| ggcggcatcg | ggatgccccg | cgttgcaggc | catnctgtcc | cagncaggta | gatgacgacc | 120 |
| atcagggaca | gcttcaagga | tcgctcgcgg | ctcttaccag | cctaacttcg | atcattggac | 180 |
| cgctgatcgt | cacggcgatt | tatcccgcct | cggcgagcac | atggaacggg | ttggcatgga | 240 |
| ttgtaggcgc | cgcccatatac | cttgtctgcc | tcccccgcgt | tgcgtcgcgg | tgcatggagc | 300 |
| cggnccacct | cgacctgaat | ggaanccggc | ggcacctcgc | taacggattc | accactccaa | 360 |
| gaattggagc | caatcaattc | ttgcggagaa | ctgtgaatgc | ncaaaccaac | ccttggcaga | 420 |
| acatatccat | cgcgtccgcc | atctccanca | gccgcacgcg | gcgcatctcg | ggcagcgttg | 480 |
| ggtcctgcag | | | | | | 490 |

<210> SEQ ID NO 77
<211> LENGTH: 470
<212> TYPE: DNA
<213> ORGANISM: Homo sapiens
<220> FEATURE:
<221> NAME/KEY: misc_feature
<222> LOCATION: (1)..(470)
<223> OTHER INFORMATION: where n may be either a or g or c or t/u,
      unknown or other

<400> SEQUENCE: 77

| | | | | | |
|---|---|---|---|---|---|
| ctgcagtgtt | taaaaaataa | aataaactaa | aagtttattt | atgaggagta | cactgctttc | 60 |
| ttgtaaacac | atgtacaagc | catataatag | agttcatttc | nnaccctagt | tacgaaaaca | 120 |
| ctagaaagtc | tncacccggc | caagataaca | catctttagg | taaaaatagc | aagaaatatt | 180 |
| ttatgggttg | tttacttaaa | tcatagtttt | caggttgggc | acagtggntc | atgcctgtaa | 240 |
| tcccagcact | ttatgcggct | gaggcaggca | gatcagttga | ggtcagaagt | ttgagaccag | 300 |
| cctgggcaat | gtggcaaaac | ctcatctcca | ctaaaaatac | aaaaattagc | caggcatggt | 360 |
| ggtgcacaca | tgttaattcc | cagctacttg | ggaggnttga | gacaggaggg | tcgcttggnc | 420 |
| ctaggaggga | agaagttgna | gggancttaa | tgtcactgca | ctctagnttg | | 470 |

<210> SEQ ID NO 78
<211> LENGTH: 445
<212> TYPE: DNA
<213> ORGANISM: Homo sapiens
<220> FEATURE:
<221> NAME/KEY: misc_feature
<222> LOCATION: (1)..(445)
<223> OTHER INFORMATION: where n may be either a or g or c or t/u,
      unknown or other

<400> SEQUENCE: 78

| | | | | | |
|---|---|---|---|---|---|
| cactcaattc | tgaatgctgc | catcatgatc | agtgtcattg | ttgtcatgac | tannctcctg | 60 |
| gtggttctgt | ataaatacag | gtgctataag | gtgagcatga | gacacagatc | tttgnttttcc | 120 |
| accctgttct | tcttatggtt | gggtattctt | gtcacagtaa | cttaactgat | ctaggaaaga | 180 |

```
aaaaatgttt tgtcttctag agataagtta attttagtt ttcttcctcc tcactgtgga      240
acattcaaaa aatacaaaaa ggaagccagg tgcatgtgta atgccaggct cagaggctga      300
ggcaggagga tcgcttgggc ccaggagttc acaagcagct tgggcaacgt agcaagaccc      360
tgcctctatt aaagaaaaca aaaacaaat attggaagta ttttatatgc atggaatcta      420
tatgtcatga aaaattagt gtaaa                                             445
```

<210> SEQ ID NO 79
<211> LENGTH: 496
<212> TYPE: DNA
<213> ORGANISM: Homo sapiens
<220> FEATURE:
<221> NAME/KEY: misc_feature
<222> LOCATION: (1)..(496)
<223> OTHER INFORMATION: where n may be either a or g or c or t/u,
      unknown or other

<400> SEQUENCE: 79

```
cctgtattta tactgaacca ccaggaggat agtcatgact acaatgacnc tgatcatgat       60
ggcagcattc agaattgagt gcagggctct ctggcccaca gtctcggtat cttctgtgaa      120
tggggtatag attctacaat aaaacaaaca caaaagccct aggtcagtgt aatggagat      180 caccaaccac attccacct ccaacacaga atttctttt tcttaattca attcgnatct       240
tataagtcac ttttcccaa ctcaccaatn ctagctaaga attttaacc tgagaaaaac       300 agctacactc taaaattgct tcaaagaaaa tgtctaacat atggaaagaa ggacttaaca      360
tgtgaagcag acactggctc catctagtgg gtgctttata ttgaaataat tataatacct      420
catcaaattt tttngggtac agnttattag gaacttggta tggaaccaga ttctgccaca      480
gaaaccacgn gggctg                                                     496
```

<210> SEQ ID NO 80
<211> LENGTH: 496
<212> TYPE: DNA
<213> ORGANISM: Homo sapiens
<220> FEATURE:
<221> NAME/KEY: misc_feature
<222> LOCATION: (1)..(496)
<223> OTHER INFORMATION: where n may be either a or g or c or t/u,
      unknown or other

<400> SEQUENCE: 80

```
cattagataa tggntcaggg tggccaaggc tccgtctgtc gttgtgctcc tgccgttctc       60
tattgtcatt ctataagcac aagaaaaaca ttttcagtaa atcagattct cagcagaatc      120
aaggtaacgg ttagacctgg gattaacaac agaccccgtca ctatgagttc taaaaacctg    180
aagcaagaaa aacaatgta caggaagtat gcagtttaaa agtctagatt atctatcatt      240
gttcactgaa ggcattcagg tcctctcttt tacctgggtc ttggnttgct ccattctctc      300
tgttcatccc aacatacaca attgtactta tcctttgaga tgtaccttaa atactgacac     360
ctgcatgaaa acttgtttac tggctgcagg tccaagcacc tttttcnaaa ttcagctttc    420
tgtgatttca gaccacatat gcaaggaact atcttacctt aattaataag antttaaaat    480
ccttgtgtca gaggcg                                                     496
```

<210> SEQ ID NO 81
<211> LENGTH: 368
<212> TYPE: DNA
<213> ORGANISM: Homo sapiens
<220> FEATURE:

```
<221> NAME/KEY: misc_feature
<222> LOCATION: (1)..(368)
<223> OTHER INFORMATION: where n may be either a or g or c or t/u,
      unknown or other

<400> SEQUENCE: 81
aggancgctt gggcccagga gttcacaagc agcttgggca acgtagcaag accctgcctc      60
tattaaagaa acaaaaaaac aaatattgga agtattttat atgcatggaa tctatatgtc     120
atgaaaaaat tagtgtaaaa tatatatatt atgattagnt atcaagattt agtgataatt     180
tatgttatnn ngggatttca atgccttttt aggccattgt ctcaaaaaat aaaagcagaa     240
aacaaaaaaa gttgtaactg aaaaataaac atttccatat aatagcacaa tctaagtggg     300
tttttgnttg tttgtttgnt tgttgaagca gggccttgcc ctnccaccca ggntggagtg     360
aagtgcag                                                              368

<210> SEQ ID NO 82
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 82
gaattccttt ttttttttttt tttttttttt ttnctcctaa tgttttatt gtnccttaga      60 taactggata gnacaaagtt ngncttngtt ttttacttaa aaaacgtact ttccgcatac     120
tgtngcccgt atgactttcc tgtcccatcg gaaaccagag tttccccagg tgagcccttc     180
ctatctgngg ntacatgatt tagctaattt aacaagaaga gagtaattcc ttnggattat     240
tatcaacatg aaacttggac tatgtctcta taagggtgaa cactgatttt ttttttcttt     300
ttagaaacaa aaaccatcca cttattaatc caaactacgg gattggattt acaacaatca     360
tcgcatnaac tgaacatacg aagttaccac tcaagggaat nacagaagaa cgttgnacaa     420
tntntcttac ggggtacgng aattcaaaca atgtgggggan aggaacttca ntctacaaan     480
tctgaccatc gnttcagtat                                                 500

<210> SEQ ID NO 83
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: where n may be either a or g or c or t/u,
      unknown or other

<400> SEQUENCE: 83
gaattccttt actcttcttt aattctaccg tctttgggca tacatctcat ttgntgtgga      60
agaaggtctg acagnagggc tgacagcacc gattcataac acattctttt catcatacaa     120
agagtaagac cctagaataa tgggaccatc tgctaccacg acagagctgc cttactggct     180
gtagaaaaag actgcttgtg tgggagagaa gaatgaggac agaggaggca tctgggcaa      240 gtgagcgtac aagtatntct acaaattcag aatttggtgg aaaatccaaa tttgncttca     300
acatgataga gaattgatga gaaaatagct gtnctgtttc caaaatttac tgaatttggg     360
aacctgaggt taaaactttt aggatnaagc aactcaggtt caagacttng nctngggaag     420
```

-continued gaatggaaac acagacggga atgagtntca                                              450

<210> SEQ ID NO 84
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: where n may be either a or g or c or t/u,
      unknown or other

<400> SEQUENCE: 84
caactgtatt tatacagnaa ccaccaggag datagtcatg acaacaatga caaactagga         60
atagccccct ttcacttctg agtcccagag gttaccaag gcaccctct gacatccggc          120
ctgcttcttc tcacatgana aaaactagcc cccagtntga tccgcaggtn gaggaatncc         180
ccgggtcgag gttcggatcc tggatgacag accctctcgc ccctgaaggn dataaccggg        240
tgtggtacat ggacggntat cacaacaacc gcttcgnacg tgagtacaag tccatggttg        300
acttcatgaa cacggacaat ttcacctccc accgtctccc ccaccctgg tcgggcacgg         360
ggnaggtggt ctncaacggt tctttctnct tcaacaagtt ccagagccac atcatcatca       420
ggtttggacc tgaaganaga gaacatcctc                                         450

<210> SEQ ID NO 85
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 85
ggatccctcc cctttttaga ccatacaagg taacttccgg acgttgccat ggcatctgta         60
aactgtcatg gtgttggcgg ggagtgtctt ttagcatgct aatgtattat aattagcgta       120
tagtgagcag tgaggataac cagaggtcac tctcctcacc atcttggttt tggtgggttt       180
tggccagctt cttttattgca accagtttta tcagcaagat cttatgagc tgtatcttgt       240
gctgacttcc tatctcatcc cgtaactaag agtacctaac ctcctgcaaa tngcagccca       300
gtaggtcttg gncttatttt acccagcccc tattcaagat agagttgctc ntggtccaaa       360
cgcctctgac acaaggattt taaagtctta ttaattaagg taagataggt ccttggatat       420
gtggtctgaa atcacagaaa gctgaatttg gaaaaggtg cttggagctg cagccagtaa        480
acaagttttc atgcaggtgt                                                    500

<210> SEQ ID NO 86
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 86
ctgcagtgag ccaaaatcgt gccactgcac ttcactccag cctgggtgac agggcaaggc         60
cctgcttcaa caaacaaaca aacaaacaaa aacccactta gattgtgcta ttatatggaa       120

| | |
|---|---|
| atgtttatttt tcagttaca acttttttg ttttctgctt ttatttgttg agacaatggc | 180 |
| ctaaaaaggc attgaaatnc caaaataaca taaattatca ctaaatcttg ataactaatc | 240 |
| ataatatata tattttacac taattttttc atgacatata gattccatgc atataaaata | 300 |
| cttccaatat ttgttttttg ttttctttaa tagaggcagg gtcttgctac gttgcccaag | 360 |
| ctgcttgtga actcctgggc ccaagcgatc ctcctgcctc agcctctgag cctggcatta | 420 |
| cacatgcacc tggcttcctt tttgtntttt ttgaatgttc cacagtgagg aggaagaaaa | 480 |
| ctnaaaatta acttatctct | 500 |

<210> SEQ ID NO 87
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: where n may be either a or g or c or t/u, unknown or other

<400> SEQUENCE: 87

| | |
|---|---|
| ctgcagatga gaggcactaa ttataagcca tattacccttt cttctgacaa ccacttgtca | 60 |
| gcccacgtgg tttctgtggc agaatctggt tctataacaa gttcctaata agctgtagcc | 120 |
| aaaaaaattt gatgaggtat tataattatt tcaatataaa gcacccacta gatggagcca | 180 |
| gtgtctgctt cacatgttaa gtccttcttt ccatatgtta gacattttct ttgaagcaat | 240 |
| tttagagtgt agctgttttt ctcaggttaa aaattcttag ctaggattgg tgagttgggg | 300 |
| aaaagtgact tataagatac gaattgaatt aagaaaaaga aaattctgtg ttggaggtgg | 360 |
| taatgtgggt ggtgatcttc attaacactg anctagggnt ttggggtttg gtttattgta | 420 |
| gaatctatac cccattcana gaagataccg | 450 |

<210> SEQ ID NO 88
<211> LENGTH: 502
<212> TYPE: DNA
<213> ORGANISM: Homo sapiens
<220> FEATURE:
<221> NAME/KEY: misc_feature
<222> LOCATION: (1)..(502)
<223> OTHER INFORMATION: where n may be either a or g or c or t/u, unknown or other

<400> SEQUENCE: 88

| | |
|---|---|
| ctgcagccag taaacaagtt ttcatgcagg tgtcagtatt taaggtacat ctcaaaggat | 60 |
| aagtacaatt gtgtatgttg ggatgaacag agagaatgga gcaagccaag acccaggtaa | 120 |
| aagagaggac ctgaatgcct tcagtgaaca atgatagata atctagactt ttaaactgca | 180 |
| tacttcctgt acattgtttt ttcttgcttc aggttttttag aactcatagt gacgggtctg | 240 |
| ttgttaatcc caggtctaac cgttaccttg attctgctga gaatctgatt tactgaaaat | 300 |
| gttttttcttg tgcttataga atgacaatag agaacggcag gagcacaacg acagacggag | 360 |
| ccttggccac cctgagccat tatctaatgg acgacccagg gtaactcccg gcaggtggtg | 420 |
| gagcaagatg aggaagaaga tgaggagctg acattgaaat atggcggcna gcatgtgatc | 480 |
| atgctcnttg gccctgtgan tc | 502 |

<210> SEQ ID NO 89
<211> LENGTH: 499
<212> TYPE: DNA
<213> ORGANISM: Homo sapiens

```
<220> FEATURE:
<221> NAME/KEY: misc_feature
<222> LOCATION: (1)..(499)
<223> OTHER INFORMATION: where n may be either a or g or c or t/u,
      unknown or other

<400> SEQUENCE: 89
ctgcagtgtt cctttctcc acttaaaaca tgaagtaata acccctcgnt ctctcaactg      60
ctcctgacca tcacagagga tgggctctcc agctaagtca tgccccttca atgnagaggc    120
cttcaaggtg atgatgacat gctgtaaaga aaagccacac tgggtttgag aataataaaa    180
caaaactcat acgtacagct gcccatcctt ccgggtataa aagctgactg acttaatggt    240
agccacgacc accaccatgc agagagtcac agggacaaag agcatgatca catgcttggc    300
gncatatttc aatgtcagnt cctcatcttc ttcctcatct tgntccacca cctgccggga    360
gttaccntgg gtcgtccatt agataatggg tcagggtggc caaggctccg tctgtcgttg    420
tgctcctgcc gttctctatt gtcattctat aagcacaaga aaacatttn cagtaaatca     480 gatnctcagc agaatcaag                                                  499

<210> SEQ ID NO 90
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 90
taactcccag gntcaagatn tctncctgcg ttagcctcct gagtagctgg gactataggt      60
atgtgccact attcctgaaa acataatcag ttttgaaggt agtgtctggg ctgggcgcag    120
tggntcacgc cttcaatccc agcactttgg gaggncgagg tgggcggatc acctgaggtc    180
aggagttcga gaccagcctg accaacatgg gataagactc catctctact aaaaatacaa    240
aaaattagcc aggcatggtg gngcatgcct gtaatcccag ctactcagga ggntgaggna    300
ggagaattgg ttggaaccta ggaagcagag gctgtggtgg agccgagatc gcaccattgg    360
actccaggct gggnaacaag agtgaaaatc cntcttaaaa aaaaaaaaaa aaaggtagng    420
ttttgnccgg ngcgggggt cacgcctgta atcccagnat tggggangc aaggnggggg     480 gtcannangn nagnagtccg                                                 500

<210> SEQ ID NO 91
<211> LENGTH: 502
<212> TYPE: DNA
<213> ORGANISM: Homo sapiens
<220> FEATURE:
<221> NAME/KEY: misc_feature
<222> LOCATION: (1)..(502)
<223> OTHER INFORMATION: where n may be either a or g or c or t/u,
      unknown or other

<400> SEQUENCE: 91
gaattctgct gacatgtcct atgttctttt ctcccctact ccttcctact gtcagnaatg      60
aagggtaggg ctccagcctg gaccctgaag taagctagag gttagaagct aaagaagaaa    120
gaaggagatt gagtccttng atgaacgtga agccaccgta ctaatctgga ctgcctacct    180
ctgcactact ctatgagaga gaaagtatgt gcattattta aaccagttgg ttgattttc     240 tattaacaaa gtcagaaaca tctctgtaaa aagccagact gaatatttta agctctatgg    300
```

```
gtcatatggt ctccagggca aacactcaac tgtgctactg tagtgtgaaa gcaggcacag    360
acaatgtatt aaccaaggag ggtggtcact ttccaatgaa agtttatcac aaattggnga    420
atacttggta ttacaccnng ggggaaggta ggagaagatc ttgcctgtgg ttgtngntgg    480
caatgttggt cttttatacg ng                                             502
```

<210> SEQ ID NO 92
<211> LENGTH: 495
<212> TYPE: DNA
<213> ORGANISM: Homo sapiens
<220> FEATURE:
<221> NAME/KEY: misc_feature
<222> LOCATION: (1)..(495)
<223> OTHER INFORMATION: where n may be either a or g or c or t/u,
      unknown or other

<400> SEQUENCE: 92

```
gaattctctc cttagaagtt ccatacacaa cacatctccc tagaagtcat tgcccttact     60
tgttctcata gccatcctaa atataaggga gtcagaagta aagtctggnt ggctgggaat    120
attggcacct ggaataaaaa tgttttctg tgaatgagaa acaaggggaa gatggatatg    180
tgacattatc ttaagacaac tccagttgca attactctgc agatgagagg cactaattat    240
aagccatatt accttttcttc tgacaaccac ttgtcagccc acgtggtttc tgtggcagaa    300
tctggttcta taacaagttc ctaataagct gtagccaaaa aaatttgatg aggtattata    360
attatttcaa tataaagcac ccactagatg gagccagtgt ctgcttcaca tgttaagtcc    420
ttctttccat atgttagaca tttctttgaa gcaatttag agtgtagctg tttctcaggt    480
taaaattctt agtag                                                     495
```

<210> SEQ ID NO 93
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 93

```
tatggttgcc tattcttgtc acagtaactn aactgatcta ggaaagaaaa aatgttttgt     60
cttctagaga taagttaatt tttagttttc ttcctcctca ctgtggaaca ttcaaaaaat    120
acaaaaagga agccaggtgc atgtgtaatg ccaggctcag aggctgaggc aggaggatcg    180
cttgggccca ggagttcaca agcagcttgg gcaacgtagc aagaccctgc ctctattaaa    240
gaaaacaaaa aacaaatatt ggaagtattt tatatgcatg gaatctatat gtcatgaaaa    300
aattagtgta aaatatatat attatgatta gttatcaaga tttagtgata atttatgtta    360
ttttgggatt tcaatgcctt tttaggccat tgtctcaaaa aaataaaagc aggaaaacaa    420
aaaaagttgt aacttgaaaa ataaacattt ccatatttat agccaactaa gtgggtttng    480
ggtnggttgg gttggttggt                                                500
```

<210> SEQ ID NO 94
<211> LENGTH: 385
<212> TYPE: DNA
<213> ORGANISM: Homo sapiens
<220> FEATURE:
<221> NAME/KEY: misc_feature
<222> LOCATION: (1)..(385)

<223> OTHER INFORMATION: where n may be either a or g or c or t/u,
     unknown or other

<400> SEQUENCE: 94

```
ttatcattaa caggtcccac aacccttaaa aagtacagat ttttttttc ttngtggaga      60
cagggtctca cttggtcgcc cagactggag tgcagtggca cgatctcagt tcaccacaac    120
ctctgcctcc tgggttcaag caatnctcgt gcttaagcct cctgagtagg tggaaccacg    180
cgtgcgcgcc accacgctag gttnattgtg gcttttttag tagagacagg gtttcgccat    240
gttgcccagg ctggtctcan attccngacc tcaagtgatc cgnccgcctc agactcccaa    300
agtgntgagc attacagntg tgtaccacta tgtcccngnc cncatctctc tttaaaacan    360
cttncattta cctagtccac tcctg                                          385
```

<210> SEQ ID NO 95
<211> LENGTH: 330
<212> TYPE: DNA
<213> ORGANISM: Homo sapiens
<220> FEATURE:
<221> NAME/KEY: misc_feature
<222> LOCATION: (1)..(330)
<223> OTHER INFORMATION: where n may be either a or g or c or t/u,
     unknown or other

<400> SEQUENCE: 95

```
gacctagaaa agaaagcatt tcaanntaat taacaggtcc cacaacccctt aaaaagtaca    60
gattttttt ttctttnngg agacagggtc tcactttgtc gcccagactg gagtgcagtg   120
gcacgatctc agctcaccac ancctctgcc tcctgggttc aagnanttct cgtgcttang   180
cctcctgagt aggtggaacc acgcgtgtgc gccaccacgc taggctactt tntgtatttt   240
tagtagagac agggtttcgc catnttgccc aggctgntct caaattcctg acccncaagt   300
gatccccccn ccttcagtac tccccatcag                                    330
```

<210> SEQ ID NO 96
<211> LENGTH: 382
<212> TYPE: DNA
<213> ORGANISM: Homo sapiens
<220> FEATURE:
<221> NAME/KEY: misc_feature
<222> LOCATION: (1)..(382)
<223> OTHER INFORMATION: where n may be either a or g or c or t/u,
     unknown or other

<400> SEQUENCE: 96

```
ggtggncgtt ctagaactag tggcncccaa ggnagaagaa gttttcttag tacagaacaa    60
aatgaaangt ctcccatgtc tacttctttc tacacagaca cggcatccat ccgttttct   120
cantctttcc nccacctttc ccgtctttct attccacaaa gccgncattg tcatcctggc   180
ccnttctcaa tgagctgttg nntacacctc ccagacggcg tggtggncgg tcagagggc    240
tcctcacttc ccagtagggg tggccgngca ggnggtgccc cncacccccc gggcggggtg   300
gttngtccnn ccggngggnt gcaccnccc caccccctccc cnctctncta ctggcggtcg    360
tntattncan natctttaag ca                                            382
```

<210> SEQ ID NO 97
<211> LENGTH: 360
<212> TYPE: DNA
<213> ORGANISM: Homo sapiens
<220> FEATURE:
<221> NAME/KEY: misc_feature
<222> LOCATION: (1)..(360)

<223> OTHER INFORMATION: where n may be either a or g or c or t/u, unknown or other

<400> SEQUENCE: 97

| ggatccaaag gaagttagag gccagctcag tctacacctg ctactgntca gtgcccaccc | 60 |
| --- | --- |
| ggtcaaggga gaccaacaca tggtaaaggt caagggcttc ttggaaggca gtcagcagcc | 120 |
| tgtgcaagat gttctccaca ctgctcagnt taaggggagc tggggcagg acctcagctg | 180 |
| gnatctctgc ttcaccagtg tccagggtt gcacaattct tgtttactcg taggatattt | 240 |
| aatcttggnn ggtgctatca taaatgggac ttatccnctn attatgtttt cttactagtt | 300 |
| gtttatgtga aggttattga tttgggtttc actttatttn gtggnaatgg agtttcactc | 360 |

<210> SEQ ID NO 98
<211> LENGTH: 208
<212> TYPE: DNA
<213> ORGANISM: Homo sapiens
<220> FEATURE:
<221> NAME/KEY: misc_feature
<222> LOCATION: (1)..(208)
<223> OTHER INFORMATION: where n may be either a or g or c or t/u, unknown or other

<400> SEQUENCE: 98

| aatgtcacgg attcctttag gtagntacac ccatcaacct ttttgagaat aaaatgaatt | 60 |
| --- | --- |
| gagagtgtta cagtctaatt ctatatcaca tgtaacttt atttggatat atcagtaata | 120 |
| gtgctttttt tttttttttt tttttttttt tttttttng gnganagagt ctcgctctgt | 180 |
| cgccaggttg gagtgnaatg gtgcgatc | 208 |

<210> SEQ ID NO 99
<211> LENGTH: 470
<212> TYPE: DNA
<213> ORGANISM: Homo sapiens
<220> FEATURE:
<221> NAME/KEY: misc_feature
<222> LOCATION: (1)..(470)
<223> OTHER INFORMATION: where n may be either a or g or c or t/u, unknown or other

<400> SEQUENCE: 99

| aacaaggttt ctcggtcggc ggtgaatata ccggggcgtc gatatttgtt gcggaatact | 60 |
| --- | --- |
| cccctgaccg taaacgtggc tttatgggca gctggctgga cttcggttct attgccgggt | 120 |
| ttgtgctggg tgcgggcgtg gtggtgttaa tttcgaccat tgtcggcgaa gcgaacttcc | 180 |
| tcgattgggg ctggcgtatt ccgttcttta tcgctctgcc gttagggatt atcgggcttt | 240 |
| acctgcgcca tgcgctggaa gagactccgg cgttccagca gnatgtcgat aaactggaac | 300 |
| agggcgaccg tgaaggtttg gaggatggcc cgaaagtctc gtttaaagag attggcacta | 360 |
| aatactggng cagnctgttg aatgtttggg cttggtaatt ggcaaccaac gtgattacta | 420 |
| natgttggtg acctatattg ccgagttatt ggcggataac ctgaattatc | 470 |

<210> SEQ ID NO 100
<211> LENGTH: 440
<212> TYPE: DNA
<213> ORGANISM: Homo sapiens
<220> FEATURE:
<221> NAME/KEY: misc_feature
<222> LOCATION: (1)..(440)
<223> OTHER INFORMATION: where n may be either a or g or c or t/u, unknown or other

<400> SEQUENCE: 100

```
taattatatt gaaatgcttc tcntctaggt catccatgnc tggnttatta tatcatctct      60
attgntgntg ctcttttta catncattta cttggggtaa gttgtgaaat ttggggtctg      120
tctttcagaa ttaactacct nngtgctgtg tagctatcat ttaaagccat gtactttgnt    180
gatgaattac tctgaagttt taattgtntc cacatatagg tcatacttgg tatataaaag    240
actagncagt attactaatt gagacattct tctgtngctc ctngcttata ataagtagaa    300
ctgaaagnaa cttaagacta cagttaattc taagcctttg gggaaggatt atatagcctt    360
ctagtaggaa gtcttgtgcn atcagaatgt ttntaaagaa agggtntcaa ggaatngtat    420
aaanaccaaa ataattgat                                                 440
```

<210> SEQ ID NO 101
<211> LENGTH: 449
<212> TYPE: DNA
<213> ORGANISM: Homo sapiens
<220> FEATURE:
<221> NAME/KEY: misc_feature
<222> LOCATION: (1)..(449)
<223> OTHER INFORMATION: where n may be either a or g or c or t/u, unknown or other

<400> SEQUENCE: 101

```
aaaacaaagc ctcttgaggt tctgaaaagg gaaagaaaaa cagaactttg tgcactacaa    60
ttatactgtt ataaaaaaca cttccataga ttacattaag cagaaacaaa cctttctttc    120
atgtgttctc ctccaggcca agctgtctaa ggaccgcaaa ggctgttgtc acttgcaggc    180
tcccagatta ggtctgaaat aggatttcac caggtcatcc attgttagtt aaatcctagt    240
aaattcattt anaccaatca atacttata agaccaattt gtaaaccagg aatgtattaa     300
tttgtcacga ctttcaacta actgacaaat ttactataag ctcaaggtag gactctttag    360
caataagtag gaaccgcctg agacaaccaa acatttcaa cccacaaang atactttaat    420
gactttctga tttnccagca aaagggggg                                      449
```

<210> SEQ ID NO 102
<211> LENGTH: 425
<212> TYPE: DNA
<213> ORGANISM: Homo sapiens
<220> FEATURE:
<221> NAME/KEY: misc_feature
<222> LOCATION: (1)..(425)
<223> OTHER INFORMATION: where n may be either a or g or c or t/u, unknown or other

<400> SEQUENCE: 102

```
ggatccgccc tcctcggcct cccaaagtgt tgggattaca ggcgtgagcc accgcacctg    60 gcttttttt tttttttttt tggnggagac agagtcttac tctgttgccc aagctggagt     120
gcagtggtgc aatcttggtt cactgnaacc tccacctcca gagttcaagc aattctctgc    180
ctcagtttct ggagtagctg ggattacagg tgcctgccat cacgcctggc taaatttggn    240
attttttttt agtagagaca gggtttcacc atgttggcca ggctggtctt gaactcctga    300
ccttgtgatc caccagcctc ggcctcccaa attgntggga ttacaggcgt gagccaccac    360
aaccaggcta agttttaaa acatgccaag tgtatttaca taatgcgata cganttatgt     420
acata                                                                425
```

<210> SEQ ID NO 103
<211> LENGTH: 386
<212> TYPE: DNA

<213> ORGANISM: Homo sapiens
<220> FEATURE:
<221> NAME/KEY: misc_feature
<222> LOCATION: (1)..(386)
<223> OTHER INFORMATION: where n may be either a or g or c or t/u,
      unknown or other

<400> SEQUENCE: 103

```
ggatccgccc gccttggcct cccaaagtgc tgggattaca ggcatgagcc accgctcctg      60
gctgagtctg cgatttcttg ccagctctac ccagttgtgt catcttaagc aagtcactga     120
acttctctgg attcccttct cctnttgtaa aataagcatg ttatctgtcc nncctgcctt     180
gggcattgtg ataaggataa gatgacatta tagaatntng caaaattaaa agcgctagac     240
aaatgatttt atgaaaatat aaagattagn ttgagtttgg gccagcatag aaaaaggaat     300
gttgagaaca ttccnttaag gattactcaa gctcccttg gtgtatatca gnngtcanna      360
cntatcttng gggctgaaaa atgttt                                          386
```

<210> SEQ ID NO 104
<211> LENGTH: 224
<212> TYPE: DNA
<213> ORGANISM: Homo sapiens
<220> FEATURE:
<221> NAME/KEY: misc_feature
<222> LOCATION: (1)..(224)
<223> OTHER INFORMATION: where n may be either a or g or c or t/u,
      unknown or other

<400> SEQUENCE: 104

```
gaaaagggaa agaaaaacag aactttgtgc actacaatta tactgttata aaaaacactt      60
ccatagatta cattaagcag aaacaaacct ttctttcatg tgttctcctc caggccaagc     120
tgtctaagga ccgcaaaggc tgttgtcact tgcaggctcc cagattaggt ctgaaatagg     180
atttcaccag gtcatccatt gttagttaaa tcctagtaaa tnca                     224
```

<210> SEQ ID NO 105
<211> LENGTH: 440
<212> TYPE: DNA
<213> ORGANISM: Homo sapiens
<220> FEATURE:
<221> NAME/KEY: misc_feature
<222> LOCATION: (1)..(440)
<223> OTHER INFORMATION: where n may be either a or g or c or t/u,
      unknown or other

<400> SEQUENCE: 105

```
ggatccgccc tcctcggcct cccaaagtgt tgggattaca ggcgtgagcc accgcacctg      60
gctttttttt ttttttttttt tggnggagac agagtcttac tctgttgccc aagctggagt     120
gcagtggtgc aatcttggtt cactgcaacc tccacctcca gagttcaagc aattctctgc     180
ctcagtttct ggagtagctg gattacaggt gcctgccat cacgcctggn taaatttggg      240
attttttttt agtagagaca gggtttcanc atgttggcca ggntggtctt ggactcctga     300
cctggtgaac caccaggctc gggctccaaa tttggttggg attacagggg gtnaancaac     360
cacaacccag nctaaagttt tnaaaacatn caaagtgttt taaaatnatg ngatacgatt     420
tattgtacaa ttaatttat                                                   440
```

<210> SEQ ID NO 106
<211> LENGTH: 448
<212> TYPE: DNA
<213> ORGANISM: Homo sapiens
<220> FEATURE:

<221> NAME/KEY: misc_feature
<222> LOCATION: (1)..(448)
<223> OTHER INFORMATION: where n may be either a or g or c or t/u,
    unknown or other

<400> SEQUENCE: 106

| | |
|---|---|
| gtctttccca tcttctccac agagtttgtg ccttacatta ttactccttg ccattttcaa | 60 |
| gaaagcattg tcagctcttc caatctccat caccttt ggg cttgttttct actttgccac | 120 |
| agattatctt gtacagcctt ttatggacca attagcattc catcaatttt atatctagca | 180 |
| tatttgcggn tagaatccca tggatgtttc ttctttgact ataacaaaat ctggggagga | 240 |
| caaaggtgat tttcctgtgt ccacatctaa caaagtcaag atccccggct ggacttttgg | 300 |
| aggttccttc caagtcttcc tgaccacctt gcactattgg actttggnaa ggaggtgcct | 360 |
| atagaaaacg attttggaac atacttcatc gcaggggac tgtgtccccc ggtggcagaa | 420 |
| nctaccaaga tttgcgggnc gaggtcaa | 448 |

<210> SEQ ID NO 107
<211> LENGTH: 198
<212> TYPE: DNA
<213> ORGANISM: Homo sapiens
<220> FEATURE:
<221> NAME/KEY: misc_feature
<222> LOCATION: (1)..(198)
<223> OTHER INFORMATION: where n may be either a or g or c or t/u,
    unknown or other

<400> SEQUENCE: 107

| | |
|---|---|
| ggatccgccc gccttggcct cccaaagtgc tgggattaca ggcatgagcc accgctcctg | 60 |
| gctgagtctg cgatttcttg ccagctctac ccagttgtgt catcttaagc aagtcactga | 120 |
| acttctctgg attcccttct ccttnagtaa aataagnatg ttatctgncc gccctgcctn | 180 |
| ggnnattgng ataaggat | 198 |

<210> SEQ ID NO 108
<211> LENGTH: 500
<212> TYPE: DNA
<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
    unknown or other

<400> SEQUENCE: 108

| | |
|---|---|
| ctgcagtgag ccgtgattgc accactttac tccagcctgg gcaacaaaat gagaccctgg | 60 |
| ctcaaaaaca aaacaaaaa caaaaaaga gtaaattaat ttaaagggaa gtattaaata | 120 |
| aataatagca cagttgatat aggttatggt aaaattataa aggtgggata ttaatatcta | 180 |
| atgtttggga gccatcacat tattctaaat aatgtnttgg tgaaaattat tgtacatctt | 240 |
| ttaaaatctg tgtaatttt tttcagggaa gtgtttaaaa cctataacgt tgctgtggac | 300 |
| tacattactg ttgcactcct gatctggaat ttgggtgtg gtgggaatga tttccattca | 360 |
| ctggaaaggt ccacttcgac tccagcaggc atatctcatt atgattagtg cctcatggnc | 420 |
| ctggtgttta tcaaagtacc tccctgaatg gactgcgtgg gtcatcttgg ntgtgattca | 480 |
| gtatatggta aaacccaaga | 500 |

<210> SEQ ID NO 109
<211> LENGTH: 500
<212> TYPE: DNA

<213> ORGANISM: Homo sapiens
<220> FEATURE:
<221> NAME/KEY: misc_feature
<222> LOCATION: (1)..(500)
<223> OTHER INFORMATION: where n may be either a or g or c or t/u,
      unknown or other

<400> SEQUENCE: 109

| | | |
|---|---|---|
| ctgcagcctt gacctcctgg gatcaatcga tcctcccacc tcagcctcct aagtagctgg | 60 |
| aactacaggt gtgcaccacc atgcccggct aatngntgta tttctgtag atacgaggtn | 120 |
| tngccatgtt gcccaggctg gtcttgaact ctgggcttag gtgatctgcc cgcctcagcc | 180 |
| tcccaaagtg ctaagattac aggcatgagc taccatgccc agccgaaatc ttcaaatgaa | 240 |
| aaagttacta tagctaatta atgatttact gaagagttat gggatgtaca cgttaccatt | 300 |
| ttctctaaat caagataaag agatgaggaa agaaaacact ccagtggggc attcctgtna | 360 |
| caaaacaaat tatcagtctt ggggtttnac catatactga aatcacaggc aagatgagcc | 420 |
| acgcagtcca tncagggagg tactggataa caccagggnc atgagggact aatcataatg | 480 |
| agatatgctg ctggagtcga | 500 |

<210> SEQ ID NO 110
<211> LENGTH: 550
<212> TYPE: DNA
<213> ORGANISM: Homo sapiens
<220> FEATURE:
<221> NAME/KEY: misc_feature
<222> LOCATION: (1)..(550)
<223> OTHER INFORMATION: where n may be either a or g or c or t/u,
      unknown or other

<400> SEQUENCE: 110

| | | |
|---|---|---|
| ctgcaggatg agagcgatct cttnttncat ttcctgcgct acgcgctgcg ggcgaccaaa | 60 |
| ttctttcgcc ataataaatt ctcctgacna aaaggggct gttagcccct ttttaaaatt | 120 |
| aatttcaggt ggaagggctg ttcacgttga cctgataaga cgcgccagcg tcacatcagg | 180 |
| caatccatgc cggatgcagc gtaaacgcct tatcccgcat ggaaccctaa aaaccttaag | 240 |
| caatggtacg ttggatctcg atgatttcga atacttcgat cacatcgnca gtgcggacgt | 300 |
| cgttgtagtt cttaacgccg ataccacatt ccataccgtt acgggacttc gttaacgtca | 360 |
| tctttggaag cggggcaggg actccagctc gncttcgtag ataaccacgt tggcacgcag | 420 |
| gaacgcgggt cgggttgtga cgtttaacac aacttccggg taaccataca ggctgngatg | 480 |
| gnaccaaatt tcgggggatt tggacaagtc aagaacttcc cgccagaccg ataatcttgt | 540 |
| tgttcagttc | 550 |

<210> SEQ ID NO 111
<211> LENGTH: 541
<212> TYPE: DNA
<213> ORGANISM: Homo sapiens
<220> FEATURE:
<221> NAME/KEY: misc_feature
<222> LOCATION: (1)..(541)
<223> OTHER INFORMATION: where n may be either a or g or c or t/u,
      unknown or other

<400> SEQUENCE: 111

| | | |
|---|---|---|
| ctgcagcttt cctttaaact aggaagactt gttcctatac cccagtaacg atacactgta | 60 |
| cactaagcaa atagcagtca aacccaaatg aaatttntac agatgttctg tgtcatttta | 120 |
| tnttgtttat gttgtctccc ccaccccac cagttcacct gccatttatt tcatattcat | 180 |

```
tcaacgtctn nntgtgtaaa aagagacaaa aacattaaa ctttttcct tcgttaattc      240 ctccctacca cccatttaca agtttagccc atacatttta ttagatgtct tttatgtttt   300
tcttttncta gatttagtgg ctgngttgtg tccgaaaggt ccacttcgta ttgctggttg   360
aaacagctca ggagagaaat gaaacgcttt ttccagctct catttactcc tgtaagtatt   420
tggagaatga tattgaatta gtaatcagng tagaatttat cgggaacttg aaganatgtn   480
actatggcaa tttcanggna cttgtctcat cttaaatgan agnatccctg gactcctgna   540
g                                                                   541
```

<210> SEQ ID NO 112
<211> LENGTH: 241
<212> TYPE: DNA
<213> ORGANISM: Homo sapiens
<220> FEATURE:
<221> NAME/KEY: misc_feature
<222> LOCATION: (1)..(241)
<223> OTHER INFORMATION: where n may be either a or g or c or t/u, unknown or other

<400> SEQUENCE: 112

```
nnccncncn nnnnnnttn ntnttgcccg ataactatag ggngacttgg agatccaccg     60
cggtggcggn cgntctagaa ctagtggatc ccccgggntg caggacccaa cgctgcccga  120
gatgcgccgc gtgcggttgc tggagatggc ggacgcgatg gatatgttct gccaagggtt  180
ggtttgcgca ttcacagttc tccgcaagaa ttgattggct ccaattcttg gagtggtgaa  240
t                                                                   241
```

<210> SEQ ID NO 113
<211> LENGTH: 834
<212> TYPE: DNA
<213> ORGANISM: Homo sapiens
<220> FEATURE:
<221> NAME/KEY: misc_feature
<222> LOCATION: (1)..(834)
<223> OTHER INFORMATION: where n may be either a or g or c or t/u, unknown or other

<400> SEQUENCE: 113

```
ccccccncc nnnnttttn ngcagcccgt aattaccctc actnccggga acaaaagctg     60
ggtaccgggc cccccctcga ggtcgacggt atcgataagc ttgatatcga attcctgcag  120
tgtttaaaaa ataaaataaa ctaaaagttt atttatgagg agtacactgc tttcttgtaa  180
acacatgtac aagccatata atagagttca tttttttaccc tagttacgga aacactagaa  240
agtcttcacc cggccaagat aacacatctt tagtaaaaat agcaagaaat attttatggg  300
ttgtttactt aaatcatagt tttcaggttg ggcacagtgg ntcatgcctg taatcccagc  360
actttatgcg gntgaggcag gcagatcagt tgaggtcaga agtttggaga ccagnctggg  420
caatgtggna aaacctcatc tccactaaaa atacaaaaat tagncaggca tggtggtgca  480
cacatgtaat tccagntact tggggaggct gagacaggag gatcgnttga acctagggag  540
ggaggagttg gagtgagcta atgtcaatgc actcttggtt ggggcganag agcaagatct  600
ttcttccaaa aaaaaaaaa aaaaaaaagc caggtgnggn ggtcaaggct gtaatccaga  660
attngggagg ccgnggaggn natcantgng gnaggngtca agngggggcng gccacatggg  720 gaacccgttn ttnttaaatn aaaattagcc ggggngggg aggactntat ccngttccgg   780
nggtgnggag gatcnttatt ntggnggagg gtggatgnnc cagttgacnc cccc         834
```

<210> SEQ ID NO 114
<211> LENGTH: 838
<212> TYPE: DNA
<213> ORGANISM: Homo sapiens
<220> FEATURE:
<221> NAME/KEY: misc_feature
<222> LOCATION: (1)..(838)
<223> OTHER INFORMATION: where n may be either a or g or c or t/u,
      unknown or other

<400> SEQUENCE: 114
ttgggcncnc gccccttaan tttttatngn ttnctanaaa aanannnggc ncnntaaaat    60 atatttttn ttgtgacccc ttttaaaagg gacccnctaa aaaattttnt ggttnntttn   120
gatttangtg ggtgnttttn ttatattttt ggngagnntc tgtagtcntc nccctcaaac   180
anntcntacn atnggnancg tgactctgtc nttngtnann ntcgntntcn ngtnattcna   240
ggnncctcgc gcnncncggg cnnngttttt tttnncnntt tttaagccna annctcagta   300
ncntccaacg gngctnngac annngnnnct ntcgngggtn ccctctntnt ngnncnnggc   360
tnnngnnnnc ngncngcngn gccntgcgnn nngnnngngg nnngntnnca tanggatngn   420
gntgctcnnc ncnngngtnn tnagtaggna nttttntnnt acttgccnnc nnntngctgc   480
gagnanagcn anntngnngn agngnngntg cgcggannntt ccctgatna nctcgagcng   540 nttacnggng cnncctngaa naagngnngt anngtgccga gncgctannc tgagcctgag   600
tntcgacngg natngtgnnt cntacngtta ngggnngcnn gancgggntg antcnccggn   660
ngancnagcg actgcctntc angcgaancg tntcangnnn gtagagcana gggtnannng   720
tcnnnnaagc ntnnagtgan tgtcntnacn ngtganttac ggcntagnct tgatntnnan   780
ncgaggnnnn atnnannntt ggananttnn tnnnntcncn tcgcggngng ncnngccg    838

<210> SEQ ID NO 115
<211> LENGTH: 803
<212> TYPE: DNA
<213> ORGANISM: Homo sapiens
<220> FEATURE:
<221> NAME/KEY: misc_feature
<222> LOCATION: (1)..(803)
<223> OTHER INFORMATION: where n may be either a or g or c or t/u,
      unknown or other

<400> SEQUENCE: 115
attcgcgcgt agcccgataa ctatagggcg acntggagnt ccaccgcggt ggcggccgct    60
ctagnaacta gtggatcccc cgggctgcag gaattcacgg actaatcctc tacagatctt   120
gctggagtgg cctttcagcc ttttgtgact gtttgtagtg aaatgtacac acaagcctac   180
aaggcagccc agatgtacca taactgtggg aaaattaaaa aaaaaaaaac acagaacctc   240
tctatgttgc ccatgctgga ctcaaactct tagacaagca atcctcgtac ctcagcctcc   300
tgagttcctg agtagctggg actacaagca tgcaccacca tgccaggcta tgagaaagtt   360 cttttttattg atccagacct tattgcctgg taacttccac cactgttcct agctctgntc   420
tctggtccta acagaggaaa atcttgaccc cacacctagt gcaactggat agcttatngt   480
tgggctngtg tttcctctat tctgggtcca ccctaaaatc cnatagatac tccaactgct   540
canagnaaac caagctctct ctctnncttn ctttcttnnn ctctattnat tnatgggnna   600
tnattnattn ngggatggn gttcggtcgc cgcccggctg gngtgaaatg ggggaggcaa   660
tcaatttaac cccacccngg gtccagggat ctcgttnaaa ccgnnnnnnn nnnnnnnna   720 ngnncnncnc nnnccnntnn nnnggtttnn nngnnnnggg nnnccnnnnn nannnnnntn   780

```
nnnccnccna nnntncnnnn ccc                                          803
```

<210> SEQ ID NO 116
<211> LENGTH: 780
<212> TYPE: DNA
<213> ORGANISM: Homo sapiens
<220> FEATURE:
<221> NAME/KEY: misc_feature
<222> LOCATION: (1)..(780)
<223> OTHER INFORMATION: where n may be either a or g or c or t/u,
      unknown or other

<400> SEQUENCE: 116

```
cnnnnnnncc cnntnattnt acgccagccg cgtaattaac cctcactaaa gggaacaaaa    60
gctgggtacc gggccccccc tcgaggtcga cggtatcgat aagcttgata tcgaattcca   120
actcctcact tgccagatgt gaccttaagc aagtgaactt ctgtgtgcca cactgttttc   180
atctgtaaaa ggataaaggg aatatcataa attagnttgt taagccttag tttaataatg   240
tctctaagtt ttacatataa gtagacagtg tctttcttgt ttagtgaata atcattctta   300
ttatttaata gtatctctac taaatttatt gtgtaagatt atactaatct tgtttagtgc   360
gtggtaatca cttctgctca tatttaacct ataagcataa tatagtttat ttatatacca   420
nttatttatt ttattttatt tgnngagatg cagcttgtct tttncaaccc agggntgngg   480
ngnagnngng naancttgnt tcactgnaac cnccaccncc caggtncaag ngattctcct   540
gntcaagccn cctnagnagn tggnattaca gnacgantac annccagnta nnnnggntnt   600
nngtngnna ggnnncacan nngcaggtn nntcgnctcc nngccantna ctnnnnccan    660
ccccnnngnn nnnnatanag natnancann nnccncnnnn ncnnnnnnng gnggannccn   720
nntngcngnn anngnnannn nntnnnnnnn nnggncnnng nnnnnnnncc nnnnnnccccc  780
```

<210> SEQ ID NO 117
<211> LENGTH: 803
<212> TYPE: DNA
<213> ORGANISM: Homo sapiens
<220> FEATURE:
<221> NAME/KEY: misc_feature
<222> LOCATION: (1)..(803)
<223> OTHER INFORMATION: where n may be either a or g or c or t/u,
      unknown or other

<400> SEQUENCE: 117

```
nnnnnnnnnc cnnnnnnttc gnncgtaacn cgantcacta tagggcgact tggagctcca    60
ccgcggtggc ggccgctcta gaactagtgg atccccggg ctgcaggaat tcgatatcaa   120
gctttngtgt gtaaaaagta ttagaatctc atgttttga acaaggttgg cagtgggttg   180
ggaggaggga ttgagattg atgcgatagg aatgtgaagg gatagcttgg ggtggatttt   240
attttttaat tttaattttt atttnttgag atggagtctt gctctgtctc ccaggctgga   300
gtgcagtggt gtgatctcag ctcacgggtt caagcgattc tcctgctgca gcctcccgag   360
tagctgggat tacaggagcg cgccaccaca cccggntaat ttnnttgtat ttttagtaga   420
gacggggttt caccatgttg gttaggctgg tctagaactc caacctcat gatccgcctg    480
cttcggcctc ccaaagtgcc ggaattacag gcgtgagcga ctgcacccgg ccgcttgggg   540
gtggattttt aaagaaattt agaagaatgt aacttggcca gataccatgt acccgttaat   600
tcatttncgg tttttggat acccatttg nnattctccc nccactggat aaataagggn    660
ggttcattnt ngnttagttt gggtntttt nagtgtggnt tctgcttatn attagaatgg   720
nctncttttnc caanctggaa agggaggagt taaaatcant accagaanca gaaattcttt   780
```
tcanttgttg cncnagaaat gcc                                              803

<210> SEQ ID NO 118
<211> LENGTH: 819
<212> TYPE: DNA
<213> ORGANISM: Homo sapiens
<220> FEATURE:
<221> NAME/KEY: misc_feature
<222> LOCATION: (1)..(819)
<223> OTHER INFORMATION: where n may be either a or g or c or t/u,
      unknown or other

<400> SEQUENCE: 118
tnccnnnncn nnnnnaattt tngcagncgc gtaattaacc tcactaaagg gaacaaaagc        60
tgggtaccgg gccccccctc gaggtcgacg gtatcgataa gcttccctcc ccttcctcag       120
ctctggcgac cctgcgctgt ggtggttctc caaccacact cattctcctc agctggctcc      180
ttgctcttct tccacccct cgttggaagt gttcctaagt gtttggcttg gcctcctctt       240 cccctt cctt agnttagact tctccactgc tccaacatca actggaaatc tatggaattg    300
attcctgttt tcagctccag tcctgttcac agggcatttt cacctgctgg cacttccaaa     360
gtgacacttc caaaccactt cctcgccctc ctctctaaac caggtctttc ttcctaactt     420
ccttatttct gagaatgtct ctgncatgtt ctaaactgaa aactcctagt caactncaca     480
ctttattccc tggatcctca attgggttcc catgtnccgt tagtgtttct tggtaagnct    540
ctgccancac cgnaggatcg actctaatca catctcaact gaattatggn aaagtcaact    600
caattctctc aaccatccca ggctccacta tggntaatat gctaaggaga gctgacccaa    660
cggggagaag atctgngggg gaggagagaa acaaagntaa tggaatnatt ctcgaaaagc    720
ccacaaggng aaggataacc cncttccnct cgaaagaggg gggatcgcca gatntcgcgc    780
ccggaaagaa accggggnga gggggttaca ntgtaagnc                           819

<210> SEQ ID NO 119
<211> LENGTH: 796
<212> TYPE: DNA
<213> ORGANISM: Homo sapiens
<220> FEATURE:
<221> NAME/KEY: misc_feature
<222> LOCATION: (1)..(796)
<223> OTHER INFORMATION: where n may be either a or g or c or t/u,
      unknown or other

<400> SEQUENCE: 119
tnttggctgg tactgcttga gcaactggtg aaactccgcg cctcacgccc cgggtgtgtc       60
cttgtccagg ggcgacgagc attctgggcg aagtccgcac gcctcttgtt cgaggcggaa    120 gacgggtct gatgctttct ccttggtcgg gactgtctcg aggcatgcat gtccagtgac     180
tcttgtgttt gctgctgctt ccctctcaga ttcttctcac cgttgtggtc agctctgctt    240
taggcatatt aatccatagt ggaggctggg atgggtgaga gaattgaggt gacttttcca    300
taattcaggt gagatgtgat tagagttcga tctgcggtgg tggcagaggc ttacaagaaa    360
cactaacggg acatgggaac caattgagga tcagggaata aagtgtgaag ttgactagga    420
ggttttcagt ttagaacatg gcagagacat tctcagaaat aaggaagtta ggaagaaaga    480
ctggtttaga gaggagggcg angaagtggt ttgggaagtg tcactttggg aagtgccagc    540
aggtgaaaat gcctgtgaca ggatggagct gaaaacagga tcaattccat agattccagt    600
tgatgtngga gcagggagaga agtcttagct aaggaagggg aagaggaggc caaggnaaca    660

| | |
|---|---|
| cttaggacaa ttgnaacgan gggggggag aagagnaagg gccacttagg ggataatnt | 720 |
| ggtgggggac ccccaagnna gggcgcannn ttaggagggg gggannntcan aggaaagtgg | 780 |
| aagnttgggt ttanct | 796 |

<210> SEQ ID NO 120
<211> LENGTH: 802
<212> TYPE: DNA
<213> ORGANISM: Homo sapiens
<220> FEATURE:
<221> NAME/KEY: misc_feature
<222> LOCATION: (1)..(802)
<223> OTHER INFORMATION: where n may be either a or g or c or t/u,
      unknown or other

<400> SEQUENCE: 120

| | |
|---|---|
| attcgtcgta ncccgatnac tatagggcga cttggagctc caccgcggtg gcggncgcgg | 60 |
| gcagggnccg gnccttttgtg gccgcccggg ccgcgaagcc ggtgtcctaa aagatgaggg | 120 |
| gcggggcgcg gncggttggg gctggggaac cccgtgtggg aaaccaggag gggcggcccg | 180 |
| tttctcgggc ttcggcgcg gccggtgga gagagattcc ggggagcctt ggtccggaaa | 240 |
| tgctgtttgc tcgaagacgt ctcagggcgc aggtgccttg ggccgggatt agtagccgtc | 300 |
| tgaactggag tggagtagga gaaagaggaa gcgtcttggg ctgggtctgc ttgagcaact | 360 |
| ggtgaaactc cgcgcctcac gccccggtg tgtccttgtc caggggcgac gagcattctg | 420 |
| ggcgaagtcc gcacgcctct tgttcgaggc ggaagacggg gtcttgatgc tttctccttg | 480 |
| ggtcgggggac tgtctcgagg catgcatgtc cagtgactct tgtgtttggt gntgcttccc | 540 |
| tctcagatct tctcaccgng gtgggcaact ctgtttaggc atattatcca tagnggaggc | 600 |
| tggatggttg aaanaattga ggtnattttc cataatcaag tgaaatttga tagagtccgn | 660 |
| ctttngggt gnaagggtta aaaaaaaata acggaaatgg aacaatgagg tcaaggatta | 720 |
| gttgagttgn tagnggttca attaganatg aaggnatcta aaataggagt agagaannng | 780 |
| ttnaaagagg gaaaattttg cc | 802 |

<210> SEQ ID NO 121
<211> LENGTH: 793
<212> TYPE: DNA
<213> ORGANISM: Homo sapiens
<220> FEATURE:
<221> NAME/KEY: misc_feature
<222> LOCATION: (1)..(793)
<223> OTHER INFORMATION: where n may be either a or g or c or t/u,
      unknown or other

<400> SEQUENCE: 121

| | |
|---|---|
| atatgcagcc gcgtaattaa cctcactaaa gggaacaaaa gctgggtacc gggcccccc | 60 |
| tcgaggtcga cggtatcgat aagcttgata tcgaattcct gcagcccggg ggatccgccc | 120 |
| cgcggcctcc caaagtgctg ggattacagg cgtgagccac cgccccgggn ctcacatttt | 180 |
| atttctattg gctagcgctg ctctaaatct tctgttcctt ctgctacacc aggcctaaca | 240 |
| ctcaaaatcc ctgccaacct tttccttcct gaagcttccc tccccttcct cagctctggc | 300 |
| gaccctgcgc tgtggtggtt ctccaaccac actcattctc ctcagctggc tccttgctct | 360 |
| tcttccaccc cctcgntgga agtgttccta agtgtttggc ttggcctcct cttcccttc | 420 |
| cttagcttag acttctccac tgctccaaca tcaactggaa atctatggaa ttgattcctg | 480 |
| tttcagctcc agtcctgttc acaggggatt ttcanctggt ggcatttcca aagtgaaatt | 540 |
| ccaaaccact tcctcggcct cctcttctaa ancaggtctt tcttcctaac ttccttattc | 600 |

```
ttgagaatgt ctctgcatgt tcttaaantg aaaactccta gtcaaattca aatttatccc      660
tgatcccaaa tggtcccatt cccgtagggt ttntgtagcc tgcacaccga ggtcggantt      720
tatnnattca ccgattatgg aaagtaacca atcttnacca nccagctcat ttgttntntg      780
ctaagagggt ncc                                                         793

<210> SEQ ID NO 122
<211> LENGTH: 440
<212> TYPE: DNA
<213> ORGANISM: Homo sapiens
<220> FEATURE:
<221> NAME/KEY: misc_feature
<222> LOCATION: (1)..(440)
<223> OTHER INFORMATION: where n may be either a or g or c or t/u,
      unknown or other

<400> SEQUENCE: 122
aaagtcatgg attcctttag gtagctacat tatcaacctt tttgagaata aaatgaattg       60
agagtgttac agtctaattc tatatcacat gtaactttta tttggatata tcagtaatag      120 tgcttttttcn tttttttttt ttnttttttt tnnttttngg gganagagtc tcgctctgtc     180
gccaggttgg agtgcaatgg tgcgatcttg gctcactgaa agctccaccn cccgggttca     240
agtgattctc ctgcctcagc cncccaagta gntgggacta caggggtgcg ccaccacgcc     300
tgggataatt ttgggntttt tagtagagat ggcgtttcac canncttggng caggctggtc    360 ttggaactcc tganatcatg atctgcctgc cttagcctcc ccaaagtgct gggattncag     420
gggtgagcca ctgttcctgg                                                 440

<210> SEQ ID NO 123
<211> LENGTH: 453
<212> TYPE: DNA
<213> ORGANISM: Homo sapiens
<220> FEATURE:
<221> NAME/KEY: misc_feature
<222> LOCATION: (1)..(453)
<223> OTHER INFORMATION: where n may be either a or g or c or t/u,
      unknown or other

<400> SEQUENCE: 123
cttagtctgt ntcgtagtca tattaattgt aagtntacac taataagaat gtgtcagagc      60
tcttaatgtc aaaactttga ttacacagtc cctttaaggc agttctgttt taaccccagg     120
tgggttaaat attccagcta tctgaggagc ttttngataa ttggacctca ccttagtagt    180
tctctaccct ggccacacat tagaatcact tgggagcttt taaaactgta agctctgccc    240
tgagatattc ttactcaatt taattgtgta gttttttaaaa ttccccagga aattctggta   300
tttctgttta ggaaccgctg cctcaagcct agcagnacag atatgtagga aattagctct    360
gtaaggttgg tcttacaggg gataaacaga tccttcctta gnccctggga cttaatcact   420
gagagtttgg gtggnggttt ngnatttaat gac                                 453

<210> SEQ ID NO 124
<211> LENGTH: 369
<212> TYPE: DNA
<213> ORGANISM: Homo sapiens
<220> FEATURE:
<221> NAME/KEY: misc_feature
<222> LOCATION: (1)..(369)
<223> OTHER INFORMATION: where n may be either a or g or c or t/u,
      unknown or other

<400> SEQUENCE: 124
```

```
gacacacatt cacacataat tatgaaagca ttttcaggca aaactcaatc acaagtctgg      60
gtttttaaca tagttaactg aatatttccc ttgggggggtt aaattttaga acagacgtnc    120
atncaatctg gaagaagagc tatgaaaaaa acctagcttg ggtnggtttc atagggtnca    180
ttatgnacac attgttattt tatcccttaa tnctagtaaa gaaatagaat ctgaaaataa    240
gtaaaactac ttggaaaaaa nttaaaagat acagaaattt ctatcttaaa tgatgtgtgg    300
gccnctgtga ttttagtngg gntggttaaa ancccagagg tgaagagnat nctctatgct    360 gtgnggggg                                                            369

<210> SEQ ID NO 125
<211> LENGTH: 516
<212> TYPE: DNA
<213> ORGANISM: Homo sapiens
<220> FEATURE:
<221> NAME/KEY: misc_feature
<222> LOCATION: (1)..(516)
<223> OTHER INFORMATION: where n may be either a or g or c or t/u,
      unknown or other

<400> SEQUENCE: 125
gctcatcatg cttcacgggg gaggctgtgc gggaagaatg ctcccacaca gnataaagaa      60
tgctcccgca caggatagag aatgcccccg cacagcatag agaagccccc gcacagcata    120
gagaatgccc ccncacagca tagagaagcc cccgcacagc atagagaatg ctcttcacct    180
ctgggttttt aaccagccaa actaaaatca cagaggscma cacatcattt aagatagaaa    240
tttctgtatc ttttaattty tttcmaagta gttttactta ttttcagatt ctatttcttt    300
actagaatta agggataaaa taacaatgtg tgcataatga accctatgaa acmaacmmaa    360
gctaggtttt tttcatagst cttcttccag attgaatgaa cgtctgttct aaaatttaac    420
cccccaggga aatattcagt taactatgtt aaaaacccag acttgtgatt gagttttgcc    480
tgaaaatgct ttcataatta tgtgtgaatg tgtgtc                               516

<210> SEQ ID NO 126
<211> LENGTH: 121
<212> TYPE: DNA
<213> ORGANISM: Homo sapiens

<400> SEQUENCE: 126
gtataatgca ggtgctataa ggtgagcatg agacacagat ctttgctttc caccctgttc      60
ttcttatggt tgggtattct tgtcacagta acttaactga tctaggaaag aaaaaatgtt    120
t                                                                    121

<210> SEQ ID NO 127
<211> LENGTH: 18
<212> TYPE: DNA
<213> ORGANISM: Artificial Sequence
<220> FEATURE:
<223> OTHER INFORMATION: primer

<400> SEQUENCE: 127
tggagactgg aacacaac                                                   18

<210> SEQ ID NO 128
<211> LENGTH: 21
<212> TYPE: DNA
<213> ORGANISM: Artificial Sequence
<220> FEATURE:
<223> OTHER INFORMATION: oligonucleotide primer
```

<400> SEQUENCE: 128
gtgtggccag ggtagagaac t                                              21

<210> SEQ ID NO 129
<211> LENGTH: 19
<212> TYPE: DNA
<213> ORGANISM: Artificial sequence
<220> FEATURE:
<223> OTHER INFORMATION: oligonucleotide primer

<400> SEQUENCE: 129
atctccggca ggcatatct                                                 19

<210> SEQ ID NO 130
<211> LENGTH: 21
<212> TYPE: DNA
<213> ORGANISM: Artificial Sequence
<220> FEATURE:
<223> OTHER INFORMATION: PCR primer

<400> SEQUENCE: 130
tgaaatcaca gccaagatga g                                              21

<210> SEQ ID NO 131
<211> LENGTH: 19
<212> TYPE: DNA
<213> ORGANISM: Artificial Sequence
<220> FEATURE:
<223> OTHER INFORMATION: primer

<400> SEQUENCE: 131
ccatagcctg tttcgtagc                                                 19

<210> SEQ ID NO 132
<211> LENGTH: 19
<212> TYPE: DNA
<213> ORGANISM: Artificial Sequence
<220> FEATURE:
<223> OTHER INFORMATION: primer

<400> SEQUENCE: 132
ccatagccta tttcgtagc                                                 19

<210> SEQ ID NO 133
<211> LENGTH: 2792
<212> TYPE: DNA
<213> ORGANISM: Homo sapiens

<400> SEQUENCE: 133
tgggacaggc agctccgggg tccgcggttt cacatcggaa acaaaacagc ggctggtctg      60
gaaggaacct gagctacgag ccgcggcggc agcggggcgg cggggaagcg tatacctaat     120
ctgggagcct gcaagtgaca acagcctttg cggtccttag acagcttggc ctggaggaga     180
acacatgaaa gaaagaacct caagaggctt tgttttctgt gaaacagtat ttctatacag     240
ttgctccaat gacagagtta cctgcaccgt tgtcctactt ccagaatgca cagatgtctg     300
aggacaacca cctgagcaat actgtacgta gccagaatga aatagagaaa cggcaggagc     360
acaacgacag acggagcctt ggccaccctg agccattatc taatggacga ccccagggta     420
actcccggca ggtggtggag caagatgagg aagaagatga ggagctgaca ttgaaatatg     480
gcgccaagca tgtgatcatg ctctttgtcc ctgtgactct ctgcatggtg gtggtcgtgg     540

```
ctaccattaa gtcagtcagc ttttataccc ggaaggatgg gcagctaatc tatacccat      600
tcacagaaga taccgagact gtgggccaga gagccctgca ctcaattctg aatgctgcca     660
tcatgatcag tgtcattgtt gtcatgacta tcctcctggt ggttctgtat aaatacaggt     720
gctataaggt catccatgcc tggcttatta tatcatctct attgttgctg ttctttttt     780
cattcattta cttgggggaa gtgtttaaaa cctataacgt tgctgtggac tacattactg     840
ttgcactcct gatctggaat tttggtgtgg tgggaatgat ttccattcac tggaaaggtc     900
cacttcgact ccagcaggca tatctcatta tgattagtgc cctcatggcc ctggtgttta     960
tcaagtacct ccctgaatgg actgcgtggc tcatcttggc tgtgatttca gtatatgatt    1020
tagtggctgt tttgtgtccg aaaggtccac ttcgtatgct ggttgaaaca gctcaggaga    1080
gaaatgaaac gcttttttcca gctctcattt actcctcaac aatggtgtgg ttggtgaata    1140
tggcagaagg agaccggaa gctcaaagga gagtatccaa aaattccaag tataatgcag     1200
aaagcacaga aagggagtca caagacactg ttgcagagaa tgatgatggc gggttcagtg    1260
aggaatggga agcccagagg gacagtcatc tagggcctca tcgctctaca cctgagtcac    1320
gagctgctgt ccaggaactt tccagcagta tcctcgctgg tgaagaccca gaggaaaggg    1380
gagtaaaact tggattggga gatttcattt tctacagtgt tctggttggt aaagcctcag    1440
caacagccag tggagactgg aacacaacca tagcctgttt cgtagccata ttaattggtt    1500
tgtgccttac attattactc cttgccattt tcaagaaagc attgccagct cttccaatct    1560
ccatcacctt tgggcttgtt ttctactttg ccacagatta tcttgtacag cctttttatgg   1620
accaattagc attccatcaa ttttatatct agcatatttg cggttagaat cccatggatg    1680
tttcttcttt gactataacc aaatctgggg aggacaaagg tgattttcct gtgtccacat    1740
ctaacaaagt caagattccc ggctggactt ttgcagcttc cttccaagtc ttcctgacca    1800
ccttgcacta ttggactttg aaggaggtg cctatagaaa acgatttgaa acatacttca     1860
tcgcagtgga ctgtgtccct cggtgcagaa actaccagat ttgagggacg aggtcaagga    1920
gatatgatag gcccggaagt tgctgtgccc catcagcagc ttgacgcgtg gtcacaggac    1980
gatttcactg acactgcgaa ctctcaggac taccggttac caagaggtta ggtgaagtgg    2040
tttaaaccaa acggaactct tcatcttaaa ctacacgttg aaaatcaacc caataattct    2100
gtattaactg aattctgaac ttttcaggag gtactgtgag gaagagcagg caccagcagc    2160
agaatgggga atgagaggt gggcaggggt tccagcttcc ctttgatttt ttgctgcaga     2220
ctcatccttt ttaaatgaga cttgttttcc cctctctttg agtcaagtca aatatgtaga    2280
ttgccttgg caattcttct tctcaagcac tgacactcat taccgtctgt gattgccatt     2340
tcttcccaag gccagtctga acctgaggtt gctttatcct aaaagttta acctcaggtt     2400
ccaaattcag taaattttgg aaacagtaca gctatttctc atcaattctc tatcatgttg    2460
aagtcaaatt tggattttcc accaaattct gaatttgtag acatacttgt acgctcactt    2520
gcccccagat gcctcctctg tcctcattct tctctcccac acaagcagtc ttttctaca    2580
gccagtaagg cagctctgtc rtggtagcag atggtcccat tattctaggg tcttactctt    2640
tgtatgatga aaagaatgtg ttatgaatcg gtgctgtcag ccctgctgtc agaccttctt    2700
ccacagcaaa tgagatgtat gcccaaagcg gtagaattaa agaagagtaa aatggctgtt    2760
gaagcaaaaa aaaaaaaaaa aaaaaaaaaa aa                                   2792
```

<210> SEQ ID NO 134
<211> LENGTH: 467

```
<212> TYPE: PRT
<213> ORGANISM: Homo sapiens

<400> SEQUENCE: 134

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400
```

```
Ser Gly Asp Trp Asn Thr Thr Ile Ala Cys Phe Val Ala Ile Leu Ile
            405                 410                 415

Gly Leu Cys Leu Thr Leu Leu Leu Ala Ile Phe Lys Lys Ala Leu
        420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 135
<211> LENGTH: 1964
<212> TYPE: DNA
<213> ORGANISM: Mus musculus
<220> FEATURE:
<221> NAME/KEY: misc_feature
<222> LOCATION: (1)..(1964)
<223> OTHER INFORMATION: where n may be either a or g or c or t/u,
      unknown or other

<400> SEQUENCE: 135
```

| | | | | | |
|---|---|---|---|---|---|
| accanacanc | ggcagctgag | gcggaaacct | aggctgcgag | ccggccgccc | gggcgcggag | 60 |
| agagaaggaa | ccaacacaag | acagcagccc | ttcgaggtct | ttaggcagct | tggaggagaa | 120 |
| cacatgagag | aaagaatccc | aagaggtttt | gttttctttg | agaaggtatt | tctgtccagc | 180 |
| tgctccaatg | acagagatac | ctgcaccttt | gtcctacttc | cagaatgccc | agatgtctga | 240 |
| ggacagccac | tccagcagcg | ccatccggag | ccagaatgac | agccagaac | ggcagcagca | 300 |
| gcatgacagg | cagagacttg | acaaccctga | gccaatatct | aatgggcggc | cccagagtaa | 360 |
| ctcaagacag | gtggtggaac | aagatgagga | ggaagacgaa | gagctgacat | tgaaatatgg | 420 |
| agccaagcat | gtcatcatgc | tctttgtccc | cgtgaccctc | tgcatggtcg | tcgtcgtggc | 480 |
| caccatcaaa | tcagtcagct | tctataccg | gaaggacggt | cagctaatct | acaccccatt | 540 |
| cacagaagac | actgagactg | taggccaaag | agccctgcac | tcgatcctga | atgcggccat | 600 |
| catgatcagt | gtcattgtca | ttatgaccat | cctcctggtg | gtcctgtata | aatacaggtg | 660 |
| ctacaaggtc | atccacgcct | ggcttattat | ttcatctctg | ttgttgctgt | tcttttttc | 720 |
| gttcatttac | ttaggggaag | tatttaagac | ctacaatgtc | gccgtggact | acgttacagt | 780 |
| agcactccta | atctggaatt | ttggtgtggt | cgggatgatt | gccatccact | ggaaaggccc | 840 |
| ccttcgactg | cagcaggcgt | atctcattat | gatcagtgcc | ctcatggccc | tggtatttat | 900 |
| caagtacctc | cccgaatgga | ccgcatggct | catcttggct | gtgatttcag | tatatgattt | 960 |
| ggtggctgtt | ttatgtccca | aggcccact | tcgtatgctg | gttgaaacag | ctcaggaaag | 1020 |
| aaatgagact | ctctttccag | ctcttatcta | ttcctcaaca | atggtgtggt | tggtgaatat | 1080 |
| ggctgaagga | gacccagaag | cccaaaggag | ggtacccaag | aaccccaagt | ataacacaca | 1140 |
| aagagcggag | agagacacac | aggacagtgg | ttctgggaac | gatgatgtg | gcttcagtga | 1200 |
| ggagtgggag | gcccaaagag | acagtcacct | ggggcctcat | cgctccactc | ccgagtcaag | 1260 |
| agctgctgtc | caggaacttt | ctgggagcat | tctaacgagt | gaagaccgg | aggaaagagg | 1320 |
| agtaaaactt | ggactgggag | atttcatttt | ctacagtgtt | ctggttggta | aggcctcagc | 1380 |
| aaccgccagt | ggagactgga | acacaaccat | agcctgcttt | gtagccatac | tgatcggcct | 1440 |
| gtgccttaca | ttactcctgc | tcgccatttt | caagaaagcg | ttgccagccc | tcccccatctc | 1500 |

-continued

```
catcaccttc gggctcgtgt tctacttcgc cacggattac cttgtgcagc ccttcatgga      1560
ccaacttgca ttccatcagt tttatatcta gcctttctgc agttagaaca tggatgtttc      1620
ttctttgatt atcaaaaaca caaaaacaga gagcaagccc gaggaggaga ctggtgactt      1680
tcctgtgtcc tcagctaaca aaggcaggac tccagctgga cttctgcagc ttccttccga      1740
gtctccctag ccacccgcac tactggactg tggaaggaag cgtctacaga ggaacggttt      1800
ccaacatcca tcgctgcagc agacggtgtc cctcagtgac ttgagagaca aggacaagga      1860
aatgtgctgg gccaaggagc tgccgtgctc tgctagcttt gaccgtgggc atggagattt      1920
acccgcactg tgaactctct aaggtaaaca aagtgaggtg aacc                       1964
```

<210> SEQ ID NO 136
<211> LENGTH: 467
<212> TYPE: PRT
<213> ORGANISM: Mus musculus
<220> FEATURE:
<221> NAME/KEY: MISC_FEATURE
<222> LOCATION: (1)..(467)
<223> OTHER INFORMATION: where X is unknown or other

<400> SEQUENCE: 136

```
Met Thr Glu Ile Pro Ala Pro Leu Ser Tyr Phe Gln Asn Ala Gln Met
1               5                   10                  15

Ser Glu Asp Ser His Ser Ser Ala Ile Arg Ser Gln Asn Asp Ser
            20                  25                  30

Gln Glu Arg Gln Gln Gln His Asp Arg Gln Arg Leu Asp Asn Pro Glu
        35                  40                  45

Pro Ile Ser Asn Gly Arg Pro Gln Ser Asn Ser Arg Gln Val Val Glu
    50                  55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Xaa
            180                 185                 190

Val Asp Tyr Val Thr Val Ala Leu Leu Ile Trp Asn Trp Gly Val Val
        195                 200                 205

Gly Met Ile Ala Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270
```

```
Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
        290                 295                 300

Ala Gln Arg Arg Val Pro Lys Asn Pro Lys Tyr Asn Thr Gln Arg Ala
305                 310                 315                 320

Glu Arg Glu Thr Gln Asp Ser Gly Ser Gly Asn Asp Asp Gly Gly Phe
                325                 330                 335

Ser Glu Glu Trp Glu Ala Gln Arg Asp Ser His Leu Gly Pro His Arg
        340                 345                 350

Ser Thr Pro Glu Ser Arg Ala Ala Val Gln Glu Leu Ser Gly Ser Ile
        355                 360                 365

Leu Thr Ser Glu Asp Pro Glu Glu Arg Gly Val Lys Leu Gly Leu Gly
        370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Xaa Val Ala Ile Leu Ile
                405                 410                 415

Gly Leu Cys Leu Xaa Leu Leu Leu Leu Ala Ile Tyr Lys Lys Gly Xaa
        420                 425                 430

Pro Ala Xaa Pro Ile Ser Ile Thr Phe Gly Phe Val Phe Xaa Phe Ala
        435                 440                 445

Thr Asp Tyr Leu Val Gln Pro Phe Met Asp Gln Leu Ala Phe His Gln
        450                 455                 460

Phe Tyr Ile
465

<210> SEQ ID NO 137
<211> LENGTH: 2285
<212> TYPE: DNA
<213> ORGANISM: Mus musculus
<220> FEATURE:
<221> NAME/KEY: misc_feature
<222> LOCATION: (1)..(2285)
<223> OTHER INFORMATION: where n may be either a or g or c or t/u,
      unknown or other

<400> SEQUENCE: 137
gaattcggca cgagggcatt ccagcagtg aggagacagc cagaagcaag cttttggagc     60
tgaaggaacc tgagacagaa gctagtcccc cctctgaatt ttactgatga agaaactgag    120
gccacagagc taaagtgact tttcccaagg tcgcccagcg aggacgtggg acttctcaga    180
cgtcaggaga gtgatgtgag ggagctgtgt gaccatagaa agtgacgtgt taaaaaccag    240
cgctgccctc tttgaaagcc agggagcatc attcatttag cctgctgaga agaagaaacc    300
aagtgtccgg gattcaagac ctctctgcgg ccccaagtgt tcgtggtgct tccagaggca    360
gggctatgct cacattcatg gcctctgaca gcgaggaaga agtgtgtgat gagcggacgt    420
ccctaatgtc ggccgagagc cccacgccgc gctcctgcca ggagggcagg cagggcccag    480
aggatggaga gaatactgcc cagtggagaa gccaggagaa cgaggaggac ggtgaggagg    540
accctgaccg ctatgtctgt agtggggttc ccggcggcc gccaggcctg aggaagagc      600 tgaccctcaa atacggagcg aagcatgtga tcatgctgtt tgtgcctgtc actctgtgca    660
tgatcgtggt ggtagccacc atcaagtctg tgcgcttcta cacagagaag aatggacagc    720
tcatctacac gccattcact gaggacacac cctcggtggg ccagcgcctc tcaactccg     780 tgctgaacac cctcatcatg atcagcgtca tcgtggttat gaccatcttc ttggtggtgc    840
```

```
tctacaagta ccgctgctac aagttcatcc atggctggtt gatcatgtct tcactgatgc    900
tgctgttcct cttcacctat atctaccttg gggaagtgct caagacctac aatgtggcca    960
tggactaccc caccctcttg ctgactgtct ggaacttcgg ggcagtgggc atggtgtgca   1020
tccactggaa gggccctctg gtgctgcagc aggcctacct catcatgatc agtgcgctca   1080
tggccctagt gttcatcaag tacctcccag agtggtccgc gtgggtcatc ctgggcgcca   1140
tctctgtgta tgatctcgtg gctgtgctgt gtcccaaagg gcctctgaga atgctggtag   1200
aaactgccca ggagagaaat gagcccatat tccctgccct gatatactca tctgccatgg   1260
tgtggacggt tggcatggcg aagctggacc cctcctctca gggtgccctc cagctcccct   1320
acgacccgga gatggaagaa gactcctatg acagttttgg ggagccttca taccccgaag   1380
tctttgagcc tcccttgact ggctacccag gggaggagct ggaggaagag gaggaaaggg   1440
gcgtgaagct tggcctcggg gacttcatct tctacagtgt gctggtgggc aaggcggctg   1500
ccacgggcag cggggactgg aataccacgc tggcctgctt cgtggccatc ctcattggct   1560
tgtgtctgac cctcctgctg cttgctgtgt tcaagaaggc gctgcccgcc ctccccatct   1620
ccatcacgtt cgggctcatc ttttacttct ccacggacaa cctggtgcgg ccgttcatgg   1680
acaccctggc ctcccatcag ctctacatct gagggacatg gtgtgccaca ggctgcaagc   1740
tgcagggaat tttcattgga tgcagttgta tagtttttaca ctctagtgcc atatattttt   1800
aagactttc tttccttaaa aaataaagta cgtgtttact tggtgaggag gaggcagaac   1860
cagctctttg gtgccagctg tttcatcacc agactttggc tcccgctttg gggagcgcct   1920
cgcttcacgg acaggaagca cagcaggttt atccagatga actgagaagg tcagattagg   1980
gtggggagaa gagcatccgg catgagggct gagatgccca aagagtgtgc tcgggagtgg   2040
cccctggcac ctgggtgctc tggctggaga ggaaaagcca gttccctacg aggagtgttc   2100
ccaatgcttt gtccatgatg tccttgttat tttattnccy ttanaaactg antcctnttn   2160
ttnttdcggc agtcacmctn ctgggragtg gcttaatagt aanatcaata aanagntgag   2220
tcctnttaga aaaaaaaaaa aaaaaaaaaa aaaaaaaaaa aaaaaaaaaa aaaaaaaaaa   2280
aaaaa                                                               2285
```

<210> SEQ ID NO 138
<211> LENGTH: 448
<212> TYPE: PRT
<213> ORGANISM: Homo sapiens

<400> SEQUENCE: 138

```
Met Leu Thr Phe Met Ala Ser Asp Ser Glu Glu Val Cys Asp Glu
1               5                  10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
                100                 105                 110
```

```
Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
130                 135                 140

Met Ile Ser Val Ile Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Thr Val
        195                 200                 205

Trp Asn Phe Gly Ala Val Met Val Cys Ile His Trp Lys Gly Pro
210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
                260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
        290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Ala Thr Gly Ser Gly Asp
        370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
                420                 425                 430

Leu Val Arg Pro Phe Met Asp Thr Leu Ala Ser His Gln Leu Tyr Ile
        435                 440                 445
```

<210> SEQ ID NO 139
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 139
ggtaccgcca ccatgacaga ggtacctgca c                           31

<210> SEQ ID NO 140
<211> LENGTH: 25

```
<212> TYPE: DNA
<213> ORGANISM: Artificial Sequence
<220> FEATURE:
<223> OTHER INFORMATION: oligonucleotide primer

<400> SEQUENCE: 140
gaattcactg gctgtagaaa aagac                                    25

<210> SEQ ID NO 141
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 141
ggatccggtc cacttcgtat gctg                                     24

<210> SEQ ID NO 142
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 142 tttttgaat tcttaggcta tggttgtgtt cca                            33

<210> SEQ ID NO 143
<211> LENGTH: 19
<212> TYPE: DNA
<213> ORGANISM: Artificial Sequence
<220> FEATURE:
<223> OTHER INFORMATION: oligonucleotide

<400> SEQUENCE: 143
gattagtggt tgttttgtg                                           19

<210> SEQ ID NO 144
<211> LENGTH: 19
<212> TYPE: DNA
<213> ORGANISM: Artificial Sequence
<220> FEATURE:
<223> OTHER INFORMATION: oligonucleotide

<400> SEQUENCE: 144
gattagtggc tgttttgtg                                           19

<210> SEQ ID NO 145
<211> LENGTH: 19
<212> TYPE: DNA
<213> ORGANISM: Artificial Sequence
<220> FEATURE:
<223> OTHER INFORMATION: primer

<400> SEQUENCE: 145
tttttccagc tctcattta                                           19

<210> SEQ ID NO 146
<211> LENGTH: 19
<212> TYPE: DNA
<213> ORGANISM: Artificial Sequence
<220> FEATURE:
<223> OTHER INFORMATION: primer

<400> SEQUENCE: 146
```

-continued

| tttttccagt tctcattta | 19 |

<210> SEQ ID NO 147
<211> LENGTH: 19
<212> TYPE: DNA
<213> ORGANISM: Artificial sequence
<220> FEATURE:
<223> OTHER INFORMATION: primer

<400> SEQUENCE: 147

| tacagtgttc tggttggta | 19 |

<210> SEQ ID NO 148
<211> LENGTH: 19
<212> TYPE: DNA
<213> ORGANISM: Artificial Sequence
<220> FEATURE:
<223> OTHER INFORMATION: oligonucleotide

<400> SEQUENCE: 148

| tacagtgttc tggttggta | 19 |

<210> SEQ ID NO 149
<211> LENGTH: 19
<212> TYPE: DNA
<213> ORGANISM: Artificial Sequence
<220> FEATURE:
<223> OTHER INFORMATION: oligonucleotide

<400> SEQUENCE: 149

| tacagtgttg tggttggta | 19 |

<210> SEQ ID NO 150
<211> LENGTH: 1092
<212> TYPE: DNA
<213> ORGANISM: Homo sapiens
<220> FEATURE:
<221> NAME/KEY: misc_feature
<222> LOCATION: (1)..(1092)
<223> OTHER INFORMATION: where n may be either a or g or c or t/u, unknown or other

<400> SEQUENCE: 150

| gtctagataa gncaacattc aggggtagaa ggggactgtt tatttttttcc tttagtctct | 60 |
| cttaaagagt gagaaaaatt ttcccaggaa tcccggtgga ctttgcttca ccactcatag | 120 |
| gttcatacca agttacaacc ccacaacctt agagcttttg ttaggaagag cttggtggg | 180 |
| attaccgtgc ttggcttggc ttggtcagga ttcaccacca gagtcatgtg ggagggggtg | 240 |
| ggaacccaaa caattcagga ttctgccctc aggaaataaa ggagaaaata gctgttggat | 300 |
| aaactaccag caggcactgc tacagcccat gctttgtggt ttaagggcca gctagttaca | 360 |
| atgacagcta gttactgttt ccatgtaatt ttcttaaagg tattaaattt ttctaaatat | 420 |
| tagagctgta acttccactt tctcttgaag gcacagwaag ggagtcacaa gacactgttg | 480 |
| cagagaatga tgatggcggg ttcagtgagg aatgggaasc ccagrgggac antcatctag | 540 |
| ggcctcatcg ctctacacct gagtcacgag ctkctntcca ggractttcc ancagtatcc | 600 |
| tcgctggtga agacccagag gaaagnatgt tcanttctcc atntttcaaa gtcatggatt | 660 |
| cctttaggta gctacattat caacctttt gagaataaaa tgaattgaga gtgttacagt | 720 |
| ctaattctat atcacatgta acttttattt ggatatatca gtaatagtgc ttttynttt | 780 |
| ttttttttt ttttttttttt ttttnggnga nagagtctcg ctctgtcgcc aggttggagt | 840 |

| | |
|---|---:|
| gcaatggtgc gatcttggct cactgaaagc tccaccnccc gggttcaagt gattctcctg | 900 |
| cctcagccnc ccaagtagnt gggactacag gggtgcgcca ccacgcctgg gataattttg | 960 |
| ggnttttag tagagatggc gtttcaccan cttgggngcag gctggtcttg gaactcctga | 1020 |
| natcatgatc tgcctgcctt agcctcccca aagtgctggg attncagggg tgagccactg | 1080 |
| ttcctgggcc tc | 1092 |

<210> SEQ ID NO 151
<211> LENGTH: 1003
<212> TYPE: DNA
<213> ORGANISM: Homo sapiens
<220> FEATURE:
<221> NAME/KEY: misc_feature
<222> LOCATION: (1)..(1003)
<223> OTHER INFORMATION: where n may be either a or g or c or t/u, unknown or other

<400> SEQUENCE: 151

| | |
|---|---:|
| ctgcagtgag ccgagatcat gctgctgtac tccagcctgg gccacagagc caaactccat | 60 |
| ctcccaaaaa aaaaaaatat taattaatat gatnaaatga tgcctatctc agaattcttg | 120 |
| taaggatttc ttagkacaag tgctgggtat aaactatana ttcratagat gncgattatt | 180 |
| acttaytatt gttattgata ataacagca gcatctacag ttaagactcc agagtcagtc | 240 |
| acatagaatc tggnactcct attgtagnaa acccnmmag aaagaaaaca cagctgaagc | 300 |
| ctaattttgt atatcattta ctgacttctc tcattcattg tggggttgag tagggcagtg | 360 |
| atattttgta attgtgaaat catancaaag agtgaccaac tttttaatat ttgtaacctt | 420 |
| tccttttag ggggagtaaa acttggattg ggagatttca ttttctacag tgttctggtt | 480 |
| ggtaaagcct cagcaacagc cagtggagac tggaacacaa ccatagcctg tttcgtagcc | 540 |
| atattaattg tmmstataca ctaataagaa tgtgtcagag ctcttaatgt cmaaactttg | 600 |
| attacacagt cccctttaagg cagttctgtt ttaaccccag gtgggttaaa tattccagct | 660 |
| atctgaggag ctttttngata attggacctc accttagtag ttctctaccc tggccacaca | 720 |
| ttagaatcac ttgggagctt ttaaaactgt aagctctgcc ctgagatatt cttactcaat | 780 |
| ttaattgtgt agttttttaaa attccccagg aaattctggt atttctgttt aggaaccgct | 840 |
| gcctcaagcc tagcagcaca gatatgtagg aaattagctc tgtaaggttg gtcttacagg | 900 |
| gataaacaga tccttcctta gtccctggac ttaatcactg agagtttggg tggtggtttt | 960 |
| ggatttaatg acacaacctg tagcatgcag tgttacttaa gac | 1003 |

<210> SEQ ID NO 152
<211> LENGTH: 1726
<212> TYPE: DNA
<213> ORGANISM: Homo sapiens
<220> FEATURE:
<221> NAME/KEY: misc_feature
<222> LOCATION: (1)..(1726)
<223> OTHER INFORMATION: where n may be either a or g or c or t/u, unknown or other

<400> SEQUENCE: 152

| | |
|---|---:|
| ggatccctcc cctttttaga ccatacaagg taacttccgg acgttgccat ggcatctgta | 60 |
| aactgtcatg gtgttggcgg ggagtgtctt ttagcatgct aatgtattat aattagcgta | 120 |
| tagtgagcag tgaggataac cagaggtcac tctcctcacc atcttggttt tggtgggttt | 180 |
| tggccagctt ctttattgca accagttta tcagcaagat ctttatgagc tgtatccttgt | 240 |
| gctgacttcc tatctcatcc cgnaactaag agtacctaac ctcctgcaaa ttgmagncca | 300 |

```
gnaggtcttg gncttatttn acccagcccc tattcaarat agagtngytc ttggnccaaa      360
cgccyctgac acaaggattt taaagtctta ttaattaagg taagatagkt ccttgsatat      420
gtggtctgaa atcacagaaa gctgaatttg gaaaaaggtg cttggasctg cagccagtaa      480
acaagttttc atgcaggtgt cagtatttaa ggtacatctc aaaggataag tacaattgtg      540
tatgttggga tgaacagaga gaatggagca anccaagacc caggtaaaag agaggacctg      600
aatgccttca gtgaacaatg atagataatc tagactttta aactgcatac ttcctgtaca      660
ttgttttttc ttgcttcagg tttttagaac tcatagtgac gggtctgttg ttaatcccag      720
gtctaaccgt taccttgatt ctgctgagaa tctgatttac tgaaaatgtt tttcttgtgc      780
ttatagaatg acaatagaga acggcaggag cacaacgaca gacggagcct tggccaccct      840
ganccattat ctaatggacg acccagggta actcccggca ggtggtggan caagatgagg      900
aagaagatga gganctgaca ttgaaatatg ncgscaagca tgtgatcatg ctctttgkcc      960
ctgtgactct ctgcatggtg gtggtcgtgg ntaccattaa gtcagtcagc ttttataccc     1020
ggaaggatgg gcagctgtac gtatgagttt kgttttatta ttctcaaasc cagtgtggct     1080
tttctttaca gcatgtcatc atcaccttga aggcctctnc attgaagggg catgacttag     1140
ctggagagcc catcctctgt gatggtcagg agcagttgag agancgaggg gttattactt     1200
catgttttaa gtggagaaaa ggaacactgc agaagtatgt ttcctgtatg gtattactgg     1260
atagggctga agttatgctg aattgaacac ataaattctt ttccacctca gggncattgg     1320
gcgcccattg ntcttctgcc tagaatattc tttccttttnc tnacttkggn ggattaaatt     1380
cctgtcatcc ccctcctctt ggtgttatat ataaagtntt ggtgccgcaa aagaagtagc     1440
actcgaatat aaaattttcc ttttaattct cagcaaggna agttacttct atatagaagg     1500
gtgcacccnt acagatggaa caatggcaag cgcacatttg ggacaaggga ggggaaaggg     1560
ttcttatccc tgcacacgt ggtcccngct gntgtgtnct nccccactg antaggtta       1620
gactggacag gcttaaacta attccaattg gntaatttaa agagaatnat ggggtgaatg     1680
ctttgggagg agtcaaggaa gagnaggtag naggtaactt gaatga                   1726
```

<210> SEQ ID NO 153
<211> LENGTH: 1883
<212> TYPE: DNA
<213> ORGANISM: Homo sapiens
<220> FEATURE:
<221> NAME/KEY: misc_feature
<222> LOCATION: (1)..(1883)
<223> OTHER INFORMATION: where n may be either a or g or c or t/u, unknown or other

<400> SEQUENCE: 153

```
cncgtataaa agaccaacat tgccancnac aaccacaggc aagatcttct cctaccttcc       60
cccnnggtgt aataccaagt attcnccaat ttgtgataaa ctttcattgg aaagtgacca      120
ccctccttgg ttaatacatt gtctgtgcct gctttcacac tacagtagca cagttgagtg      180
tttgccctgg agaccatatg acccatagag cttaaaatat tcagtctggc ttttttacaga    240
gatgtttctg actttgttaa tagaaaatca acccaactgg tttaaataat gcacatactt      300
tctctctcat agagtagtgc agaggtagnc agtccagatt agtasggtgg cttcacgttc      360
atccaaggac tcaatctcct tctttcttct ttagcttcta acctctagct tacttcaggg      420
tccaggctag agccctasce ttcatttctg acagtaggaa ggagtagggg agaaaagaac      480
ataggacatg tcagcagaat tctctcctta gaagttccat acacaacaca tctccctaga     540
```

| | |
|---|---:|
| agtcattgcc cttacttgtt ctcatagcca tcctaaatat aagggagtca gaagtaaagt | 600 |
| ctkkntggct gggaatattg gcacctggaa taaaaatgtt tttctgtgaa tgagaaacaa | 660 |
| ggggaagatg gatatgtgac attatcttaa gacaactcca gttgcaatta ctctgcagat | 720 |
| gagaggcact aattataagc catattacct ttcttctgac aaccacttgt cagcccncgt | 780 |
| ggtttctgtg gcagaatctg gttcyatamc aagttcctaa taanctgtas ccnaaaaaat | 840 |
| ttgatgaggt attataatta tttcaatata aagcacccac tagatggagc cagtgtctgc | 900 |
| ttcacatgtt aagtccttct ttccatatgt tagacatttt ctttgaagca atttagagt | 960 |
| gtagctgttt ttctcaggtt aaaaattctt agctaggatt ggtgagttgg ggaaaagtga | 1020 |
| cttataagat ncgaattgaa ttaagaaaaa gaaaattctg tgttggaggt ggtaatgtgg | 1080 |
| ktggtgatct ycattaacac tganctaggg ctttkgkgtt tgktttattg tagaatctat | 1140 |
| accccattca nagaagatac cgagactgtg ggccagagag ccctgcactc aattctgaat | 1200 |
| gctgccatca tgatcagngt cattgtwgtc atgactannc tcctggtggt tcwgtataaa | 1260 |
| tacaggtgct ataaggtgag catgagacac agatctttgn tttccacccct gttcttctta | 1320 |
| tggttgggta ttcttgtcac agtaacttaa ctgatctagg aaagaaaaaa tgttttgtct | 1380 |
| tctagagata agttaatttt tagttttctt cctcctcact gtggaacatt caaaaaatac | 1440 |
| aaaaaggaag ccaggtgcat gtgtaatgcc aggctcagag gctgaggcag gaggatcgct | 1500 |
| tgggcccagg agttcacaag cagcttgggc aacgtagcaa gaccctgcct ctattaaaga | 1560 |
| aaacaaaaaa caaatattgg aagtatttta tatgcatgga atctatatgt catgaaaaaa | 1620 |
| ttagtgtaaa atatatatat tatgattagn tatcaagatt tagtgataat ttatgttatt | 1680 |
| ttgggatttc aatgcctttt taggccattg tctcaamaaa taaaagcaga aaacaaaaaa | 1740 |
| agttgtaact gaaaaataaa catttccata taatagcaca atctaagtgg gtttttgntt | 1800 |
| gtttgtttgn ttgttgaagc agggccttgc cctnycaccc aggntggagt gaagtgcagt | 1860 |
| ggcacgattt tggctcactg cag | 1883 |

<210> SEQ ID NO 154
<211> LENGTH: 1990
<212> TYPE: DNA
<213> ORGANISM: Homo sapiens
<220> FEATURE:
<221> NAME/KEY: misc_feature
<222> LOCATION: (1)..(1990)
<223> OTHER INFORMATION: where n may be either a or g or c or t/u,
    unknown or other

<400> SEQUENCE: 154

| | |
|---|---:|
| atgtttgaca atttctccgt tccacccttg attaaataag gtagtattca ttttttaagt | 60 |
| tttagctttt ggatatatgt gtaagtgtgg tatgctgtct aatgaattaa gacaattggt | 120 |
| nctktcttta cccmacanct ggacmaagag caggcaagat ncaanaatca agtgacccag | 180 |
| ncaaaccaga cacattttct gctctcagct agcttgccac ctagaaagac tggttgtcna | 240 |
| agttggagtc caagaatcgc ggaggatgtt taaaatgcag tttctcaggt tctcnccacc | 300 |
| caccagaagt tttgattcat tgagtggtgg gagagggcag agatatttgc gattttaaca | 360 |
| gcattctctt gattgtgatg cagctggttc scaaataggg accctaaaga aatgacaggt | 420 |
| gttaaattta ggatggccat cgcttgtatg ccgggagaag cacacgctgg gcccaattta | 480 |
| tatagggct ttcgtcctca gctcgagcar cctcagaacc ccgacaaccy acgccagckc | 540 |
| tctgggcgga ttccrtcagk tggggaagsc caggtggagc tctggkttct ccccgcaatc | 600 |

```
gtttctccag gccggaggcc ccgccccctt cctcctggct cctcccctcc tccgtgggcc        660
gnccgccaac gacgccagag ccggaaatga cgacaacggt gagggttctc gggcggggcc        720
tgggacaggc agctccgggg tccncgnnwt nacatcggaa acaaaacagc ggctggtctg        780
gaaggaacct gakctacgac ccgcggcggc agcggggcgg cggggaagcg tatgtgcgtg        840
atggggagtc cggcaagcc aggaaggcac cgcggacatg gcggccgcg ggcagggncc         900
ggnccttgt ggccgcccgg gccgcgaagc cggtgtccta aaagatgagg ggcggggcgc         960
ggccggttgg ggctggggaa ccccgtgtgg gaaaccagga ggggcggccc gtttctcggg       1020
cttcgggcgc ggccgggtgg agagagattc cggggagcct tggtccggaa atgctgtttg       1080
ctcgaagacg tctcagggcg caggtgcctt gggccgggat tagtagccgt ctgaactgga       1140
gtggagtagg agaaagagga agcgtcttgg gctgggtctg cttgagcaac tggtgaaact       1200
ccgcgcctca cgccccgggt gtgtccttgt ccaggggcga cgagcattct gggcgaagtc       1260
cgcacgcctc ttgttcgagg cggaagacgg ggtcttgatg cttttctcctt ggtcgggact      1320
gtctcgaggc atgcatgtcc agtgactctt gtgtttgctg ctgcttccct ctcagattct       1380
tctcaccgtt gtggtcagct ctgctttagg catattaatc catagtggag gctgggatgg       1440
gtgagagaat tgaggtgact tttccataat tcaggtgaga tgtgattaga gtycggatcc       1500
tncggtggtg gcagaggctt accaagaaac actaacggga catgggaacc aattgaggat       1560
ccagggaata aagtgtgaag ttgactagga ggttttcagt ttaagaacat ggcagagaca       1620
ttctcagaaa taaggaagtt aggaagaaag acctggttta gagaggaggg cgaggaagtg       1680
gtttggaagt gtcactttgg aagtgccagc aggtgaaaat gccctgtgaa caggactgga       1740
gctgaaaaca ggaatcaatt ccatagattt ccagttgatg ttggagcagt ggagaagtct       1800
aanctaagga aggggaagag gaggccaagc caaacactta ggaacactn cnacgagggg        1860
gtggaagaag agcaaggagc cagctgagga gaatgagtgt ggttggagaa ccaccacagc       1920
ncagggtcgc caganctgag gaaggggagg gaagcttatc gagkamsgwc racmkcgagt       1980
tggcagggat                                                             1990

<210> SEQ ID NO 155
<211> LENGTH: 736
<212> TYPE: DNA
<213> ORGANISM: Homo sapiens

<400> SEQUENCE: 155
gtctttccca tcttctccac agagtttgtg ccttacatta ttactccttg ccattttcaa        60
gaaagcattg tcagctcttc caatctccat caccctttggg cttgttttct actttgccac      120
agattatctt gtacagcctt ttatggacca attagcattc catcaatttt atatctagca       180
tatttgcggt tagaatccca tggatgtttc ttctttgact ataacaaaat ctggggagga       240
caaaggtgat ttcctgtgtc cacatctaac aaatcaagat ccccggctgg acttttggag       300
gttccttcca agtcttcctg accaccttgc actattggac tttggaagga ggtgcctata       360
gaaaacgatt ttgaacatac ttcatcgcag tggactgtgt cctcggtgca gaaactacca       420
gatttgaggg acgaggtcaa ggagatatga taggcccgga agttgctgtg ccccatcagc       480
agcttgacgc gtggtcacag gacgattttc actgacactg cgaactctca ggactaccgt       540
taccaagagg ttaggtgaag tggttttaaac caaacggaac tcttcatctt aaactacacg       600
ttgaaaatca acccaataat tctgtattaa ctgaattctg aacttttcag gaggtactgt       660
```

```
gaggaagagc aggcaccacc agcagaatgg ggaatggaga ggtgggcagg ggttccagct      720 tcccttttgat ttttttg                                                     736
```

<210> SEQ ID NO 156
<211> LENGTH: 1117
<212> TYPE: DNA
<213> ORGANISM: Homo sapiens
<220> FEATURE:
<221> NAME/KEY: misc_feature
<222> LOCATION: (1)..(1117)
<223> OTHER INFORMATION: where n may be either a or g or c or t/u,
      unknown or other

<400> SEQUENCE: 156

```
ggatccgccc gccttggcct cccaaagtgc tgggattaca ggcatgagcc accgctcctg       60
gctgagtctg cgatttcttg ccagctctac ccagttgtgt catcttaagc aagtcactga      120
acttctctgg attcccttct cctnnwgtaa aataagnatg ttatctgncc nncctgcctt      180
gggcattgtg ataaggataa gatgacatta tagaatntng caaaattaaa agcgctagac      240
aaatgatttt atgaaaatat aaagattagn ttgagtttgg gccagcatag aaaaaggaat      300
gttgagaaca ttccnttaag gattactcaa gcyccccttt tgstgknwaa tcaganngtc      360
atnnamntat cntntgtggg ytgaaaatgt ttggttgtct caggcggttc ctacttattg      420
ctaaagagtc ctaccttgag cttatagtaa atttgtcagt tagttgaaag tcgtgacaaa      480
ttaatacatt cctggtttac aaattggtct tataagtatt tgattggtnt aaatgnattt      540
actaggattt aactaacaat ggatgacctg gtgaaatcct atttcagacc taatctggga      600
gcctgcaagt gacaacagcc tttgcggtcc ttagacagct tggcctggag gagaacacat      660
gaaagammgg tttgwntctg nttawtgtaa tctatgraag tgtttttwat macagtataa      720
ttgtmtgmac aaagttctgt ttttctttcc ctttncagaa cctcaagagg ctttgttttc      780
tgtgaaacag tatttctata cagntgctcc aatgacagag tnacctgcac cgttgtccta      840
cttccagaat gcacagatgt ctgaggacaa ccacctgagc aatactgtac gtagccaggt      900
acagcgtcag tytctnaaac tgcctyygnc agactggatt cacttatcat ctcccctcac      960
ctctgagaaa tgctgagggg gstaggnagg gctttctcta cttnaccaca tttnataatt     1020
attttttggt gaccttcagc tgatcgctgg gagggacaca gggcttnttt aacacatagg     1080
gtgttggata cagnccctcc ctaattcaca tttcanc                              1117
```

<210> SEQ ID NO 157
<211> LENGTH: 540
<212> TYPE: DNA
<213> ORGANISM: Homo sapiens
<220> FEATURE:
<221> NAME/KEY: misc_feature
<222> LOCATION: (1)..(540)
<223> OTHER INFORMATION: where n may be either a or g or c or t/u,
      unknown or other

<400> SEQUENCE: 157

```
ctgcagcttt cctttaaact aggaagactt gttcctatac cccagtaacg atacactgta       60
cactaagcaa atagcagtca aacccaaatg aaatttntac agatgttctg tgtcatttta      120
tnttgtttat gttgtctccc ccacccccac cagttcacct gccatttatt tcatattcat      180
tcaacgtctn nntgtgtaaa aagagacaaa aaacattaaa cttttttcct tcgttaattc      240
ctccctacca cccatttaca agtttagccc atacatttta ttagatgtct tttatgtttt      300
tcttttncta gatttagtgg ctgtttngtg tccgaaaggt ccacttcgta tgctggttga      360
```

```
aacagctcag gagagaaatg aaacgctttt tccagctctc atttactcct gtaagtattt      420
ggagaatgat attgaattag taatcagngt agaatttatc gggaacttga aganatgtna      480
ctatggcaat ttcanggnac ttgtctcatc ttaaatgana gnatccctgg actcctgnag      540
```

<210> SEQ ID NO 158
<211> LENGTH: 509
<212> TYPE: DNA
<213> ORGANISM: Homo sapiens
<220> FEATURE:
<221> NAME/KEY: misc_feature
<222> LOCATION: (1)..(509)
<223> OTHER INFORMATION: where n may be either a or g or c or t/u,
     unknown or other

<400> SEQUENCE: 158

```
ccccgtcnat gcatactttg tgtgtccagt gcttacctgg aatccngtct ttcccaacag       60
caacaatggt gtggttggtg aatatggcag aaggagaccc ggaagctcaa aggagagtat      120
ccaaaaattc caagtataat gcagaaagta ggtaactyyy nttagatamn atcttgattt      180
tncagggtca ctgttataag ctaacagtat agnaatgttt ttatcgtctt tctnkggnca      240
tagactcctn kgagaatctc ttgagaacta tgataatgcc cagtaaatac ncagataagt      300
atttaaggag tncagatact caaancccaa caatacngtc aaagcatcct aggttaagac      360
amcncccatt aaatacagaa taccagcatg gaaaggttca ggctgaggtt atgattgggt      420
ttgggttttg ggnnngtttt ttataagtca tgattttaaa aagaaaaaat aaactctctc      480
caaacatgta aaagtaagaa tctcctaaa                                        509
```

<210> SEQ ID NO 159
<211> LENGTH: 823
<212> TYPE: DNA
<213> ORGANISM: Homo sapiens
<220> FEATURE:
<221> NAME/KEY: misc_feature
<222> LOCATION: (1)..(823)
<223> OTHER INFORMATION: where n may be either a or g or c or t/u,
     unknown or other

<400> SEQUENCE: 159

```
caggagtgga ctaggtaaat gnaagntgtt ttaaagagag atgnggncng ggacatagtg       60
gtacacanct gtaatgctca ncactkatgg ggagtactga aggnggnsgg atcacttgng      120
ggtcnggaat ntgagancag cctgggcaan atggcgaaac cctgtctcta ctaaaaatag      180
ccanaawnwa gcctagcgtg gtggcgcrca cgcgtggttc cacctactca ggaggcntaa      240
gcacgagnan tncttgaacc caggaggcag aggntgtggt garctgagat cgtgccactg      300
cactccagtc tgggcgacma agtgagaccc tgtctccnnn aagaaaaaaa aaatctgtac      360
tttttaaggg ttgtgggacc tgttaattat attgaaatgc ttctyttcta ggtcatccat      420
gcctggctta ttatatcatc tctattgttg ctgctctttt ttacattcat ttacttgggg      480
taagttgtga aatttggggt ctgtctttca gaattaacta cctnngtgct gtgtagctat      540
catttaaagc catgtacttt gntgatgaat tactctgaag ttttaattgt ntccacatat      600
aggtcatact tggtatataa aagactagnc agtattacta attgagacat tcttctgtng      660
ctcctngctt ataataagta gaactgaaag naacttaaga ctacagttaa ttctaagcct      720
ttggggaagg attatatagc cttctagtag gaagtcttgt gcnatcagaa tgtttntaaa      780
gaaagggtnt caaggaatng tataaanacc aaaaataatt gat                        823
```

<210> SEQ ID NO 160
<211> LENGTH: 945
<212> TYPE: DNA
<213> ORGANISM: Homo sapiens
<220> FEATURE:
<221> NAME/KEY: misc_feature
<222> LOCATION: (1)..(945)
<223> OTHER INFORMATION: where n may be either a or g or c or t/u, unknown or other

<400> SEQUENCE: 160

```
gttntccnaa ccaacttagg agnttggacc tgggraagac cnacntgatc tccgggaggn      60
aaagactnca gttgagccgt gattgcaccc actttactcc aagcctgggc aaccaaaatg     120
agacactggc tccaaacaca aaacaaaaa caaaaaaga gtaaattaat ttanagggaa      180
gnattaaata aataatagca cagttgatat aggttatggt aaaattataa aggtgggana     240
ttaatatcta atgtttggga gccatcacat tattctaaat aatgttttgg tggaaattat     300
tgtacatctt ttaaaatctg tgtaattttt tttcagggaa gtgtttaaaa cctataacgt     360
tgctgtggac tacattactg ttncactcct gatctgaat tttggtgtgg tgggaatgat      420
ttccattcac tggaaaggtc cacttcgact ccagcaggca tatctcatta tgattagtgc     480
cctcatgncc ctgktgttta tcaagtacct ccctgaatgg actgngtggc tcatcttggc     540
tgtgatttca gtatatggta aaacccaaga ctgataattt gtttgtcaca ggaatgcccc     600
actggagtgt tttctttcct catctcttta tcttgattta gagaaatgg taacgtgtac      660
atcccataac tcttcagtaa atcattaatt agctatagta acttttttcat ttgaagattt    720
cggctgggca tggtagctca tgcctgtaat cttagcactt tgggaggctg aggcgggcag     780
atcacctaag cccagagttc aagaccagcc tgggcaacat ggcaaaacct cgtatctaca     840
gaaaatacaa aaattagccg ggcatggtgg tgcacacctg tagttccagc tacttaggag     900
gctgaggtgg gaggatcgat tgatcccagg aggtcaagnc tgcag                     945
```

<210> SEQ ID NO 161
<211> LENGTH: 4
<212> TYPE: PRT
<213> ORGANISM: Homo sapiens

<400> SEQUENCE: 161

Tyr Pro Thr Phe
1

<210> SEQ ID NO 162
<211> LENGTH: 4
<212> TYPE: PRT
<213> ORGANISM: Homo sapiens

<400> SEQUENCE: 162

Ser Thr Pro Glu
1

<210> SEQ ID NO 163
<211> LENGTH: 19
<212> TYPE: DNA
<213> ORGANISM: Artificial Sequence
<220> FEATURE:
<223> OTHER INFORMATION: primer

<400> SEQUENCE: 163
cattcactga ggacacacc         19

```
<210> SEQ ID NO 164
<211> LENGTH: 18
<212> TYPE: DNA
<213> ORGANISM: Artificial Sequence
<220> FEATURE:
<223> OTHER INFORMATION: primer

<400> SEQUENCE: 164
tgtagagcac caccaaga                                                 18

<210> SEQ ID NO 165
<211> LENGTH: 18
<212> TYPE: DNA
<213> ORGANISM: Artificial Sequence
<220> FEATURE:
<223> OTHER INFORMATION: primer

<400> SEQUENCE: 165
gcatggtgtg catccact                                                 18

<210> SEQ ID NO 166
<211> LENGTH: 18
<212> TYPE: DNA
<213> ORGANISM: Artificial Sequence
<220> FEATURE:
<223> OTHER INFORMATION: primer

<400> SEQUENCE: 166
ggaccactct gggaggta                                                 18

<210> SEQ ID NO 167
<211> LENGTH: 18
<212> TYPE: DNA
<213> ORGANISM: Artificial Sequence
<220> FEATURE:
<223> OTHER INFORMATION: primer

<400> SEQUENCE: 167
aaacttggat tgggagat                                                 18

<210> SEQ ID NO 168
<211> LENGTH: 15
<212> TYPE: PRT
<213> ORGANISM: Homo sapiens

<400> SEQUENCE: 168

Asn Asp Asn Arg Glu Arg Gln Glu His Asn Asp Arg Arg Ser Leu
1               5                   10                  15

<210> SEQ ID NO 169
<211> LENGTH: 15
<212> TYPE: PRT
<213> ORGANISM: Homo sapiens

<400> SEQUENCE: 169

Lys Asp Gly Gln Leu Ile Tyr Thr Pro Phe Thr Glu Asp Thr Glu
1               5                   10                  15

<210> SEQ ID NO 170
<211> LENGTH: 15
<212> TYPE: PRT
<213> ORGANISM: Homo sapiens

<400> SEQUENCE: 170

Glu Ala Gln Arg Arg Val Ser Lys Asn Ser Lys Tyr Asn Ala Glu
```

```
1               5               10              15
```

<210> SEQ ID NO 171
<211> LENGTH: 15
<212> TYPE: PRT
<213> ORGANISM: Homo sapiens

<400> SEQUENCE: 171

```
Ser His Leu Gly Pro His Arg Ser Thr Pro Glu Ser Arg Ala Ala
1               5                   10                  15
```

<210> SEQ ID NO 172
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 172
cagaggatgg agagaatac                                                    19

<210> SEQ ID NO 173
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 173
ggctccccaa aactgtcat                                                    19

<210> SEQ ID NO 174
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 174
gccctagtgt tcatcaagta                                                   20

<210> SEQ ID NO 175
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 175
aaagcgggag ccaaagtc                                                     18

<210> SEQ ID NO 176
<211> LENGTH: 20
<212> TYPE: DNA
<213> ORGANISM: Artificial Sequence
<220> FEATURE:
<223> OTHER INFORMATION: PCR primer

<400> SEQUENCE: 176
tcacagaaga taccgagact                                                   20

<210> SEQ ID NO 177
<211> LENGTH: 20
<212> TYPE: DNA
<213> ORGANISM: Artificial Sequence
<220> FEATURE:

<223> OTHER INFORMATION: PCR primer

<400> SEQUENCE: 177
cccaaccata agaagaacag                                                    20

<210> SEQ ID NO 178
<211> LENGTH: 22
<212> TYPE: DNA
<213> ORGANISM: Artificial Sequence
<220> FEATURE:
<223> OTHER INFORMATION: PCR primer

<400> SEQUENCE: 178
tctgtacttt ttaagggttg tg                                                 22

<210> SEQ ID NO 179
<211> LENGTH: 22
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(22)
<223> OTHER INFORMATION: where n may be either a or g or c or t/u,
      unknown or other

<400> SEQUENCE: 179
acttcagagt aattcatcan ca                                                 22

<210> SEQ ID NO 180
<211> LENGTH: 19
<212> TYPE: DNA
<213> ORGANISM: Artificial Sequence
<220> FEATURE:
<223> OTHER INFORMATION: PCR primer

<400> SEQUENCE: 180
gactccagca ggcatatct                                                     19

<210> SEQ ID NO 181
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(20)
<223> OTHER INFORMATION: where n may be either a or g or c or t/u,
      unknown or other

<400> SEQUENCE: 181
gatgagacaa gtnccntgaa                                                    20

<210> SEQ ID NO 182
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(20)
<223> OTHER INFORMATION: where n may be either a or g or c or t/u,
      unknown or other

<400> SEQUENCE: 182

```
ttagtggctg tttngtgtcc                                              20

<210> SEQ ID NO 183
<211> LENGTH: 20
<212> TYPE: DNA
<213> ORGANISM: Artificial Sequence
<220> FEATURE:
<223> OTHER INFORMATION: PCR primer

<400> SEQUENCE: 183
cacccattta caagtttagc                                              20

<210> SEQ ID NO 184
<211> LENGTH: 241
<212> TYPE: DNA
<213> ORGANISM: Homo sapiens
<220> FEATURE:
<221> NAME/KEY: misc_feature
<222> LOCATION: (1)..(241)
<223> OTHER INFORMATION: where n may be either a or g or c or t/u,
      unknown or other

<400> SEQUENCE: 184
cncnnnnnnn nnnnnnnatt tngtctgtgc cgcntaaata ttaattgtcc ctatacanta   60
ataagantgt gtcagagctc ttaatgtcaa aactttgatt acacagtccc tttaaggcag  120
ttctgtttta accccaggtg ggttaaatat tccagctatc tgaggagctt ttngataatt  180
ggacctcacc ttagtagttc tctaccctgg ccacacatta gaatcacttg ggagctttta  240
a                                                                 241

<210> SEQ ID NO 185
<211> LENGTH: 241
<212> TYPE: DNA
<213> ORGANISM: Homo sapiens
<220> FEATURE:
<221> NAME/KEY: misc_feature
<222> LOCATION: (1)..(241)
<223> OTHER INFORMATION: where n may be either a or g or c or t/u,
      unknown or other

<400> SEQUENCE: 185
tcnnnnnnnn nccccntaaa tttctccctg ccccgnaaag gttacaaata tcaaaaagnt   60
ggtcactctt nggtatgatt tcacaattca aaactatcac tgccctactc aaccccacaa  120
tgaatgagag aagtcagtaa atgatataca aaattaggct tcagctgtgt ttnctttctt  180
tnggggtttn ctacaatagg agtnccagat tctatgtgac tgactctgga gtcttaactg  240
t                                                                 241
```